IMAGE

United States Patent
Christopher et al.

(10) Patent No.: US 9,808,457 B2
(45) Date of Patent: Nov. 7, 2017

(54) CGRP RECEPTOR ANTAGONISTS

(71) Applicant: Heptares Therapeutics Limited, Welwyn Garden City, Hertfordshire (GB)

(72) Inventors: John Andrew Christopher, Welwyn Garden City (GB); Miles Stuart Congreve, Welwyn Garden City (GB); Sarah Joanne Bucknell, Welwyn Garden City (GB); Francesca Deflorian, Welwyn Garden City (GB); Mark Pickworth, Welwyn Garden City (GB); Jonathan Stephen Mason, Welwyn Garden City (GB)

(73) Assignee: Heptares Therapeutics Limited, Hertfordshire (GB)

( * ) Notice: Subject to any disclaimer, the term of this patent is extended or adjusted under 35 U.S.C. 154(b) by 0 days.

(21) Appl. No.: 15/336,866

(22) Filed: Oct. 28, 2016

(65) Prior Publication Data

US 2017/0121348 A1    May 4, 2017

(30) Foreign Application Priority Data

Oct. 30, 2015 (GB) .................... 1519196.8

(51) Int. Cl.
| | | |
|---|---|---|
| *A61K 31/496* | (2006.01) | |
| *C07D 241/14* | (2006.01) | |
| *C07D 498/20* | (2006.01) | |
| *C07D 471/04* | (2006.01) | |
| *C07D 401/14* | (2006.01) | |

(52) U.S. Cl.
CPC .......... *A61K 31/496* (2013.01); *C07D 241/14* (2013.01); *C07D 401/14* (2013.01); *C07D 471/04* (2013.01); *C07D 498/20* (2013.01)

(58) Field of Classification Search
CPC .. C07D 498/20; C07D 401/14; C07D 241/04; A61K 31/496
USPC ......................................... 514/230.5, 252.13
See application file for complete search history.

(56) References Cited

U.S. PATENT DOCUMENTS

| | | |
|---|---|---|
| 6,294,534 B1 | 9/2001 | Nargund et al. |
| 6,344,449 B1 | 2/2002 | Rudolf et al. |
| 6,410,548 B2 | 6/2002 | Nargund et al. |
| 7,220,862 B2 | 5/2007 | Chaturvedula et al. |
| 7,314,883 B2 | 1/2008 | Chen et al. |
| 7,452,903 B2 | 11/2008 | Burgey et al. |
| 7,498,325 B2 | 3/2009 | Rudolf et al. |
| 7,534,784 B2 | 5/2009 | Burgey et al. |
| 7,569,578 B2 | 8/2009 | Luo et al. |
| 7,732,438 B2 | 6/2010 | Paone et al. |
| 7,745,427 B2 | 6/2010 | Paone et al. |
| 7,754,732 B2 | 7/2010 | Chaturvedula et al. |
| 7,772,244 B2 | 8/2010 | Degnan et al. |
| 7,807,666 B2 | 10/2010 | Doods et al. |
| 7,834,007 B2 | 11/2010 | Han et al. |
| 7,842,808 B2 | 11/2010 | Chaturvedula et al. |
| 8,039,460 B2 | 10/2011 | Burgey et al. |
| 8,044,043 B2 | 10/2011 | Luo |
| 8,314,117 B2 | 11/2012 | Luo et al. |
| 8,481,546 B2 | 7/2013 | Chaturvedula et al. |
| 2007/0049577 A1 | 3/2007 | Han et al. |
| 2007/0149503 A1 | 6/2007 | Chaturvedula et al. |

FOREIGN PATENT DOCUMENTS

| | | |
|---|---|---|
| WO | WO 1999-64002 A1 | 12/1999 |
| WO | WO 2003-104236 A1 | 12/2003 |
| WO | WO 2005-056550 A2 | 6/2005 |
| WO | WO 2005-065779 A1 | 7/2005 |
| WO | WO 2005-092880 A1 | 10/2005 |

(Continued)

OTHER PUBLICATIONS

Bell et al., "MK-8825: A potent and selective CGRP receptor antagonist with good oral activity in rats", Bioorganic & Medicinal Chemistry Letters, 2012, 22, 3941-3945.
Bell, I.M., "Calcitonin Gene-Related Peptide Receptor Antagonists: New Therpeutic Agents for Migraine", J. Med. Chem, 2014, 57(19), 7838-7858.
Chaturvedula et al., "Discovery of (R)-N-(3-(7-methyl-1H-indazol-5-yl)-1-(4-(1-methylpi-peridin-4-yl)-1-oxopropan-2-yl)-4-(2-oxo-1,2-dihydroquinolin-3-yl)-piperidine-1-carboxamide (BMS-742413): A potent human CGRP antagonist with superior safety profile for the treatment of migraine through intranasal delivery", Bioorganic & Medicinal Chemistry Letters, 2013, 23, 3157-3161.
Cheng et al., "Relationship Between the Inhibition Constant ($K_I$) and the Concentration of Inhibitor Which Causes 50 Per Cent Inhibition ($I_{50}$) of an Enzymatic Reaction", Biochemical Pharmacology, 1973, 22, 3009-3108.

(Continued)

*Primary Examiner* — Kathrien Cruz
*Assistant Examiner* — Janet L Coppins
(74) *Attorney, Agent, or Firm* — Baker Hostetler LLP

(57) ABSTRACT

The disclosures herein relate to novel compounds of formula

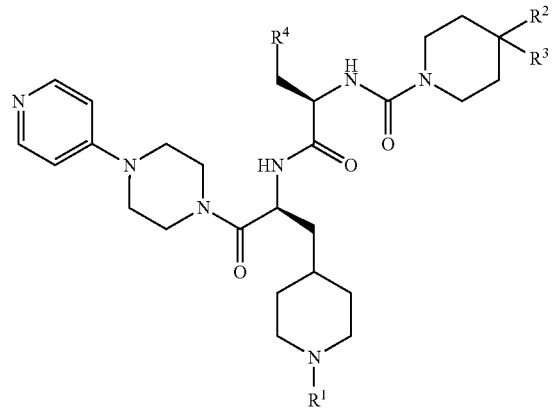

wherein $R^1$, $R^2$, $R^3$ and $R^4$ are as defined herein, and their use in treating, preventing, ameliorating, controlling or reducing cerebrovascular or vascular disorders associated with CGRP receptor function.

17 Claims, No Drawings

(56) References Cited

FOREIGN PATENT DOCUMENTS

| WO | WO 2005-095383 A1 | 10/2005 | |
|----|-------------------|---------|---|
| WO | WO 2005-103037 A2 | 11/2005 | |
| WO | WO 2006-044504 A1 | 4/2006 | |
| WO | WO 2006-100009 A1 | 9/2006 | |
| WO | WO-2011-123232 A1 | 10/2011 | |
| WO | WO 2011123232 A1 * | 10/2011 | ........... C07D 401/14 |
| WO | WO 2013-169348 A1 | 11/2013 | |

OTHER PUBLICATIONS

Copeland, R.A., "The dynamics of drug-target interactions: drug-target residence time and its impact on efficacy and safety", Expert Opinion on Drug Discovery, 2010, 5(4), 305-310.

Davis et al., "The Toruous Road to an Ideal CGRP Function Blocker for the Treatment of Migraine", Current Topics in Medicinal Chemistry, 2008, 8, 1468-1479.

Degnan et al., "Discovery of (R)-4-(8-Fluoro-2-oxo-1,2-dihydroquinazolin-3(4H)-yl)-N-(3-7-methyl-1H-indazol-5-yl)-1-oxo-1-(4-(piperidine-1-1y)piperidin-1-yl)propan-2-y1)piperidine-1-carboxamide (BMS-694153): A Potent Antagonist of the Human Calcitonin Gene-Related Peptide Receptor for Migraine with Rapid and Efficient Intranasal Exposure", J. Med. Chem., 2008, 51, 4858-4861.

Degnan et al., "Carbamates as potent calcitonin gene-related peptide antagonists with improved solution stability", Bioorganic & Medicinal Chemistry Letters, 2009, 19, 3555-3558.

Han et al., "The synthesis and SAR of calcitonin gene-related peptide (CGRP) receptor antagonists derived from tyrosine surrogates. Part 1", Bioorganic & Medicinal Chemistry Letters, 2012, 22, 4723-4727.

Han et al., "The synthesis and SAR of calcitonin gene-related peptide (CGRP) receptor antagonists derived from tyrosine surrogates. Part 2", Bioorganic & Medicinal Chemistry Letters, 2012, 23, 1870-1873.

Ho et al., "Efficacy and tolerability of MK-0974 (telcagepant), a new oral antagonist of calcitonin gene-related peptide receptor, compared with zolmitriptan for acute migraine: a randomised, placebo-controlled, parallel-treatment trial", Lancet, 2008, 372, 2115-2123.

International Patent Application No. PCT/IB2016/056517 filed Oct. 28, 2016, International Search Report dated Dec. 2, 2016, 12 pages.

Luo et al., "Calcitonin gene-related peptide (CGRP) receptor antagonists: Novel aspartates and succinates", Bioorganic & Medicinal Chemistry Letters, 2012, 22, 2912-2916.

Luo et al., "Calcitonin gene-related peptide (CGRP) receptor antagonists: Pyridine as a Replacement for a core amide group", Bioorganic & Medicinal Chemistry Letters, 2012, 22, 2917-2921.

Negro et al., "CGRP receptor antagonists: an expanding drug class for acute migraine?", Expert Opinion on Investigational Drugs, 2012, 21(6), 807-818.

Olesen et al., "Clinical Proof of Concept Study Group Calcitonin gene-related peptide receptor antagonist BIBN 4096 BS for the acute treatment of migraine", The New England Journal of Medicine, 2004, 350(11), 1104-1110.

Paone et al., "Calcitonin gene-related peptide receptor antagonists for the treatment of migraine: a patent review", Expert Opinion on Therapeutic Patents, 2009, 19(12), 1675-1713.

Poyner et al., "CGRP receptor antagonists: design and screening", Expert Opin. Drug Discovery, 2009, 4(12), 1253-1265.

Rich et al., "Biacore analysis with Stabilized G-protein-coupled receptors", Analytical Biochemistry, Feb. 2011, 409(2), 267-272.

Rudolf et al., "Development of Human Calcitonin Gene-Related Peptide (CGRP) Receptor Antagonists. 1. Potent and Selective Small Molecule CGRP Antagonists. 1-[$N^2$-[3,5-Dibromo-N-[[4-(3,4-dihydro-2(1H)-oxoquinazolin-3-yl)-1-piperidinyl]carbonyl]-D-tyrosyl]-L-lysyl]-4-(4-pyridinyl)piperazine: The First CGRP Antagonist for Clinical Trials in Acute Migraine", J. Med. Chem. 2005, 48, 5921-5931.

Salvatore et al., "Pharmacological Properties of MK-3207, a Potent and Orally Active Calcitonin Gene-Related Peptide Receptor Antagonist", The Journal of Pharmacology and Experimental Therapeutics, Apr. 2010, 333(1), 152-160.

Schindler et al., "Binding properties of the novel, non-peptide CGRP receptor antagonist radioligand, [$^3$H)BIBN4096BS", European Journal of Pharmacology, May 2002, 442(3), 187-193.

ter Haar et al., "Crystal Structure of the Ectodomain Complex of the CGRP Receptor, a Class-B GPCR, Reveals the Site of Drug Antagonism", Structure, Sep. 2010, 18(9), 1083-1093.

Tora et al., "Preparation of imidazoles as potent calcitonin gene-related peptide (CGRP) antagonists", Bioorganic & Medicinal Chemistry Letters, 2013, 23, 5684-5688.

Waeber, C., "Emerging Drugs in Migraine Treatment", Expert Opin. Emerging Drugs, 2003, 8(2), 437-456.

Williams et al., "Non-peptide calcitonin gene-related peptide receptor antagonists from a benzodiazepinone lead", Bioorganic & Medicinal Chemistry Letters, 2006, 16, 2595-2598.

Williams et al., "Receptor Antagonists for the Treatment of Migraine", Progress in Medicinal Chemistry, vol. 47, Edited by G. Lawton and D.R. Witty, 2009, 1-35.

Wood et al., "Novel CGRP receptor antagonists through a design strategy of target simplification with addition of molecular flexibility", Bioorganic & Medicinal Chemistry Letters, 2009, 19, 5787-5790.

Zartman et al., "Identification of a novel RAMP-independent CGRP receptor antagonist", Bioorganic & Medicinal Chemistry Letters, 2011, 21, 6705-6708.

* cited by examiner

CGRP RECEPTOR ANTAGONISTS

CROSS REFERENCE TO RELATED APPLICATION

This application claims the benefit of Great Britain Patent Application No. 1519196.8, filed Oct. 30, 2015, the entirety of which is incorporated by reference herein.

TECHNICAL FIELD

This application relates to novel compounds and their use as CGRP receptor antagonists. Compounds described herein may be useful in the treatment or prevention of cerebrovascular or vascular disorders such as migraine. The application is also directed to pharmaceutical compositions comprising these compounds and the manufacture and use of these compounds and compositions in the prevention or treatment of such cerebrovascular or vascular disorders.

BACKGROUND OF THE INVENTION

Migraine is a highly disabling neurovascular disorder characterized by attacks of moderate to severe headache that are often associated with nausea, vomiting, photophobia, and phonophobia. The attacks can last from 4 to 72 h, and the average attack frequency is 1 or 2 per month. About 20-30% of migraine patients experience transient focal neurologic symptoms known as aura, which are usually visual and can precede or accompany the headache. Migraine afflicts about 11% of adults worldwide and results in a significant socioeconomic burden, in terms of both quality of life and lost productivity.

Whilst the pathomechanism of migraine is still unclear, one of the leading hypotheses is based on activation of the trigeminovascular system (TS). Several neuropeptides participate in this activation, calcitonin gene-related peptide (CGRP) playing a crucial role among them. CGRP exerts various biological effects through the peripheral and central nervous system (CNS). The functional CGRP-receptor (CGRP-R) complex has been well characterized, and novel therapeutic approaches target CGRP itself and its receptors. This invention relates to the development of CGRP receptor antagonists (CGRP-RA).

CGRP, a 37-amino acid neuropeptide derived from the gene encoding calcitonin, is formed from the alternative splicing of the calcitonin/CGRP gene located on chromosome 11. In humans, CGRP has two isoforms: $\alpha$- and $\beta$-CGRP. The $\beta$-isoform differs from the $\alpha$-isoform in the amino acids located at positions 3, 22 and 25. The chemical structure of CGRP involves a disulphide bridge between residues 2 and 7 and an amidated C-terminus. The cyclic cysteine2-cysteine7 motif has a basic role in receptor activation. In the human trigeminal ganglia (TRIG), CGRP-immunoreactive neurons account for up to 50% of all neurons. It has been demonstrated through an in situ hybridization technique that 40% of all nerve cell bodies contain CGRP mRNA and CGRP. Double immunostaining has shown that in the human TRIG CGRP is co-localized with nitric oxide synthase, substance P (SP), pituitary adenylate cyclase activating peptide (PACAP) and nociceptin, which may play a role in the pathomechanism of migraine.

The functional CGRP-R consists of three proteins: i) Calcitonin Receptor Like Receptor (known as CRLR, CAL-CRL or CLR) is a seven-transmembrane spanning protein, which forms the ligand binding site with; ii) RAMP1, determining the specificity of the receptor; and iii) the CGRP-R component protein (RCP) couples the receptor to intracellular signal transduction pathways and to adenylyl cyclase.

It is thought that the C-terminal region of CGRP initially binds to the large N-terminal extracellular domain (ECD) of the receptor, likely making interactions with both CLR and RAMP1. This initial binding event greatly increases the local concentration of the N-terminal region of CGRP in the vicinity of the juxtamembrane portion of CLR, allowing their relatively weak interaction to occur and resulting in receptor activation. Since mutagenesis experiments indicated that most small molecule antagonists interacted with the ECD of CLR/RAMP1, it was hypothesized that they bind to this region of the receptor and prevent the initial binding of CGRP to the receptor. A notable exception to this model of peptide binding and small molecule receptor antagonism is the hydroxypyridine class of antagonists, which apparently interact with transmembrane domain 7 (TM7) in CLR and not with the extracellular domain (Bell I M, J. Med. Chem., 2014, 57(19), 7838-58).

The first clinically tested CGRP-RA, olcegepant, was based on a dipeptide backbone, had high molecular weight, and was not orally bioavailable. Nonetheless, when dosed intravenously, olcegepant proved to be an effective antimigraine agent, and this proof-of-concept study greatly increased interest in the field. Following the success of olcegepant, a number of orally acting CGRP-RAs were advanced to clinical trials. Telcagepant and compounds BI 44370, MK-3207, and BMS-927711 have all been used for acute treatment of migraine as oral agents. Taken together, the results from these clinical studies demonstrate that CGRP-RAs can exhibit similar antimigraine efficacy to the gold standard triptan drugs but with a significantly lower incidence of adverse events than is typically observed with a triptan. It is worth noting that the available data indicate that these CGRP blockers do not cause vasoconstriction and suggest that they may have a superior cardiovascular safety profile to the triptans. One potential concern that has been reported with some CGRP-RAs is the observation of elevated levels of liver transaminases in some patients, and this reportedly led to the discontinuation of MK-3207. Although elevated liver enzymes were also found in a small number of subjects after dosing with telcagepant for an extended period, it is not clear if these findings are in some way mechanism-based or specific to these two compounds. In clinical trials for acute migraine therapy, the CGRP-RAs displayed favourable effects, but their frequent administration was associated with liver toxicity (the elevation of liver transaminases), which limited their clinical use. Hence, there is a need to develop new CGRP-RAs which do not induce liver injury.

SUMMARY OF THE INVENTION

One possibility to address the risk of liver injury is to target a non-oral route of delivery for a small molecule which will place a lower burden on the liver through first-pass exposure. The compounds of the invention can be used for sub-cutaneous, intravenous and/or intranasal routes of administration. The molecular profile for a CGRP-RA intended for such routes of administration differs from the profile required for an oral molecule: extremely high affinity and functional potency, coupled with extremely high solubility is required. Disclosed herein are novel compounds, and the first medical use of said compounds as CGRP receptor antagonists.

Compounds of the invention include compounds of formula (I)

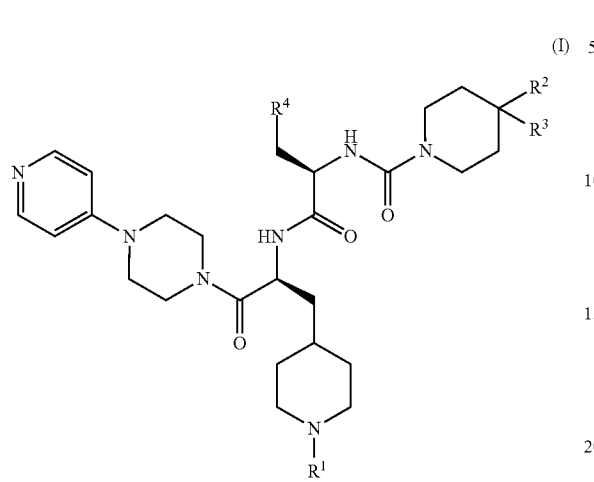

(I)

or salts thereof, wherein $R^1$ is selected from H or Q-($C_1$-$C_6$)alkyl; where Q is a bond, C(O) or C(O)O and where the ($C_1$-$C_6$)alkyl can be optionally substituted by N($C_1$-$C_3$alkyl)$_2$ or $CO_2H$; $R^2$ is H or forms a spirocyclic heterocyclic ring with $R^3$;

$R^3$ forms a spirocyclic heterocyclic ring with $R^2$ or is a heterocyclic ring if $R^2$ is H; and $R^4$ is an optionally substituted aryl group which may be monocyclic or fused to a further ring.

DETAILED DESCRIPTION OF THE INVENTION

The invention relates to novel compounds. The invention also relates to the use of novel compounds as CGRP receptor antagonists. The invention further relates to the use of compounds in the manufacture of medicaments for use as CGRP receptor antagonists. The invention further relates to compounds, compositions and medicaments for the treatment of cerebrovascular or vascular disorders such as migraine (including subtypes such as: migraine without aura, chronic migraine, pure menstrual migraine, menstrually-related migraine, migraine with aura, familial hemiplegic migraine, sporadic hemiplegic migraine, basilar-type migraine, cyclical vomiting, abdominal migraine, benign paroxysmal vertigo of childhood, retinal migraine), status migrainosus, cluster headache, dialysis headache, paroxysmal hemicrania, osteoarthritis, hot flashes associated with menopause or medically induced menopause due to surgery or drug treatment, hemicrania continua, cyclic vomiting syndrome, allergic rhinitis, or rosacea. The invention further relates to compounds, compositions and medicaments for the treatment of broader pain states and diseases involving neurogenic inflammation including dental pain, earache, middle ear inflammation, sunburn, joint pain associated with osteoarthritis and rheumatoid arthritis, cancer pain, fibromyalgia, diabetic neuropathy, pain associated with inflammatory bowel disease—Crohn's disease, gout, complex regional pain syndrome, Behçet's disease, endometriosis pain, back pain or cough.

Compounds exemplified herein are based around the structure:

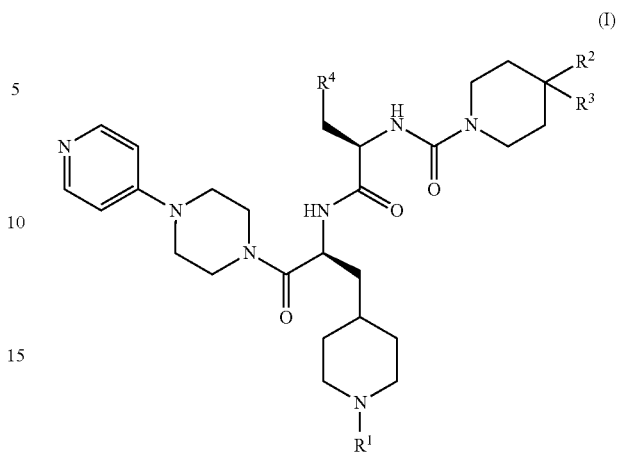

(I)

wherein $R^1$ is selected from H or Q-($C_1$-$C_6$)alkyl; where Q is a bond, C(O) or C(O)O and where the ($C_1$-$C_6$)alkyl can be optionally substituted by N($C_1$-$C_3$alkyl)$_2$ or $CO_2H$;

$R^2$ is H or forms a spirocyclic heterocyclic ring with $R^3$;

$R^3$ forms a spirocyclic heterocyclic ring with $R^2$ or is a heterocyclic ring if $R^2$ is H; and $R^4$ is an optionally substituted aryl group which may be monocyclic or fused to a further ring.

The optional substituents for $R^4$ may be selected from halo, hydroxyl or methyl. More particularly, the substituent for $R^4$ is a substituted phenyl group wherein the substituents are selected from halo or hydroxyl. In a particular embodiment, $R^4$ is a moiety according to formula II

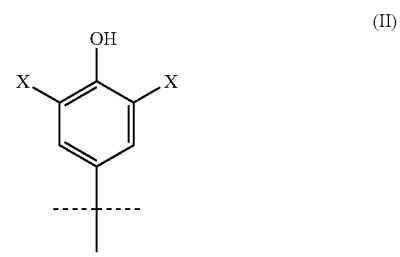

(II)

wherein X is halo.

In a more particular embodiment, X is Br.

In a particular embodiment, the substituent for $R^4$ is

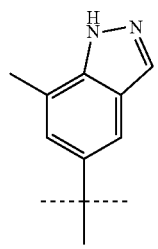

In a particular embodiment, the substituent for $R^2$ is H and $R^3$ is selected from:

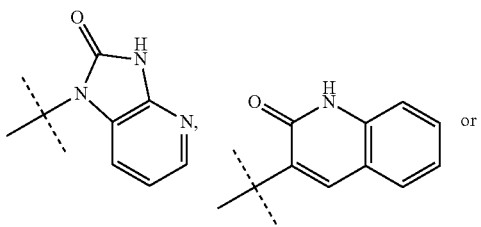

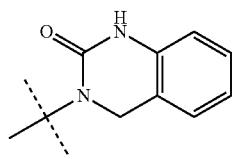

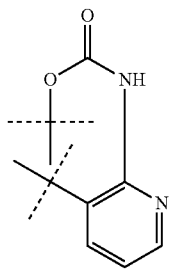

In a particular embodiment, R² forms a spirocyclic heterocyclic ring with R³ to form:

In a particular embodiment, the substituent for R¹ is H, CO₂ᵗBu, CH₂CH₃, CH₂CH₂CH₃, COCH₂CH₂CH₂CH₃, CH₂CH₂N(CH₃)₂ or COCH₂CO₂H. In a more particular embodiment, the substituent for R¹ is H.

Compounds of the invention include those of formula (I)

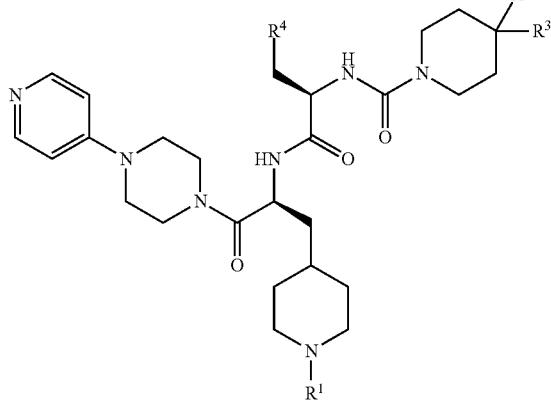

(I)

wherein R¹ is selected from H or Q-(C₁-C₆)alkyl; where Q is a bond, C(O) or C(O)O and where the (C₁-C₆)alkyl can be optionally substituted by N(C₁-C₃alkyl)₂ or CO₂H;

R² is H or forms a spirocyclic heterocyclic ring with R³ to form:

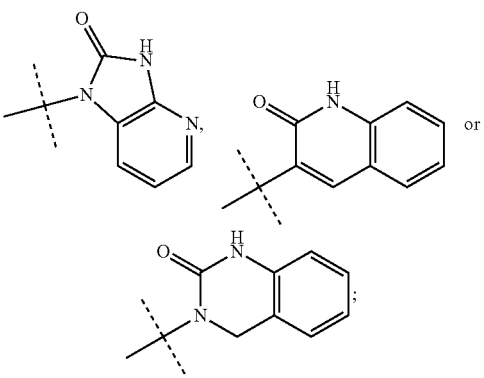

and wherein when R² is H, R³ is selected from:

and
R⁴ is selected from

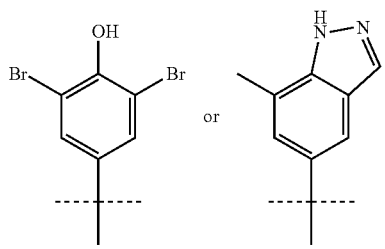

In a more particular embodiment, the substituent for R¹ is H.

Further embodiments of the invention include methods of treatment comprising administering a compound of formulas (I) as a CGRP receptor antagonist. The treatment using a compound of formulas (I) may be in the treatment of cerebrovascular or vascular disorders such as migraine (including subtypes such as: migraine without aura, chronic migraine, pure menstrual migraine, menstrually-related migraine, migraine with aura, familial hemiplegic migraine, sporadic hemiplegic migraine, basilar-type migraine, cyclical vomiting, abdominal migraine, benign paroxysmal vertigo of childhood, retinal migraine), status migrainosus, cluster headache, dialysis headache, paroxysmal hemicrania, osteoarthritis, hot flashes associated with menopause or medically induced menopause due to surgery or drug treatment, hemicrania continua, cyclic vomiting syndrome, allergic rhinitis, or rosacea. The invention further relates to compounds, compositions and medicaments for the treatment of broader pain states and diseases involving neurogenic inflammation including dental pain, earache, middle ear inflammation, sunburn, joint pain associated with osteoarthritis and rheumatoid arthritis, cancer pain, fibromyalgia, diabetic neuropathy, pain associated with inflammatory bowel disease—Crohn's disease, gout, complex regional pain syndrome, Behçet's disease, endometriosis pain, back pain or cough.

Certain novel compounds of the invention show particularly high activities as CGRP receptor antagonists.

Exemplary compounds include:

(1)

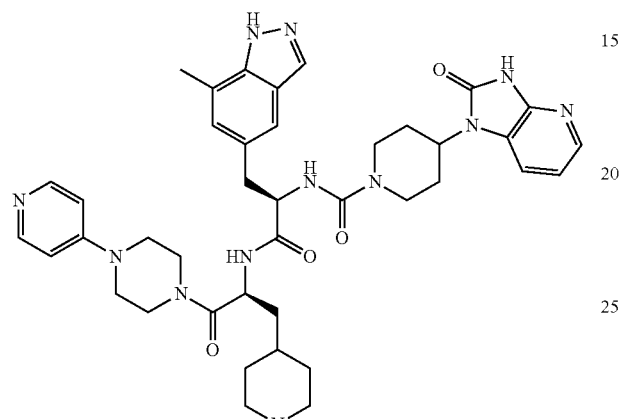

(2)

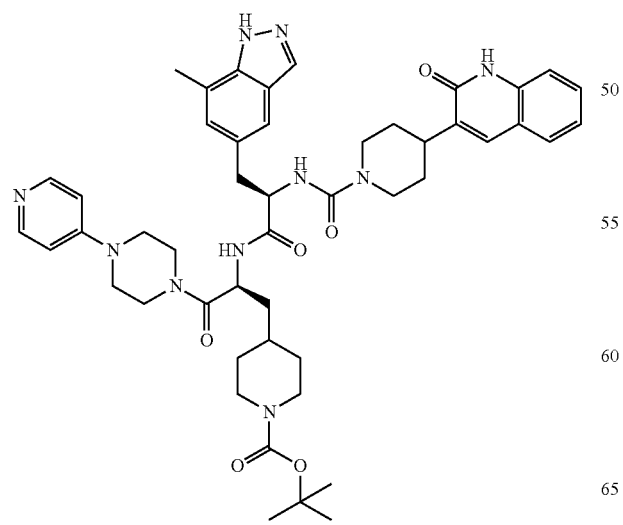

(3)

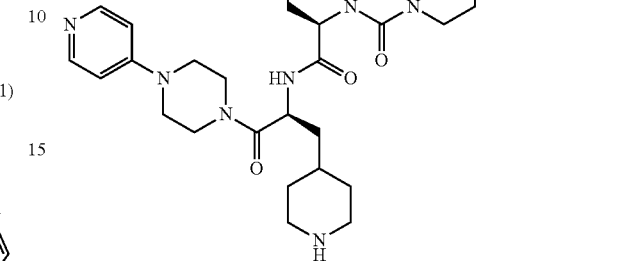

(4)

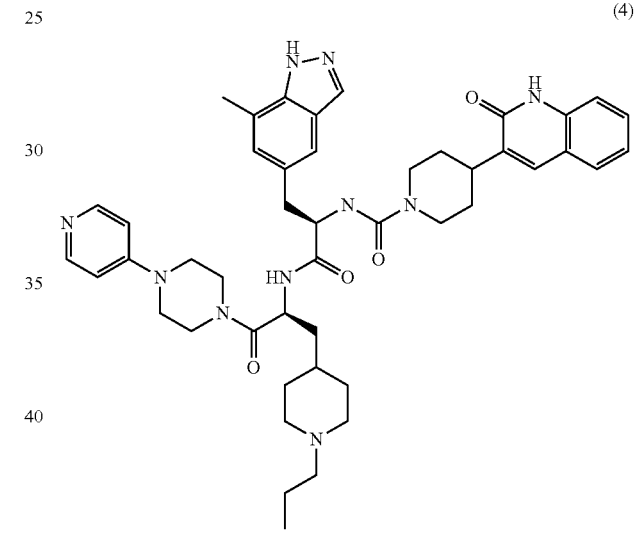

(5)

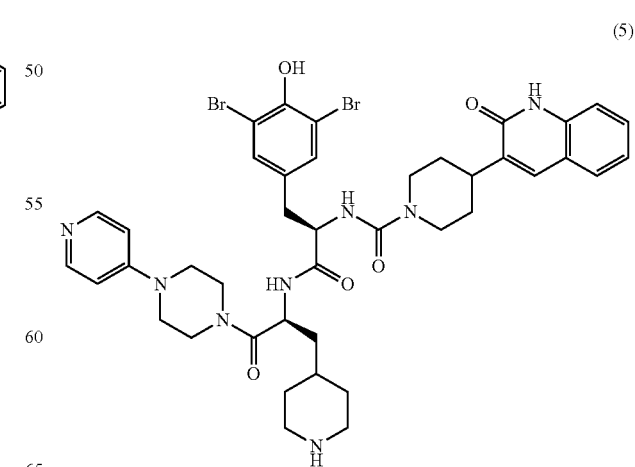

(6)
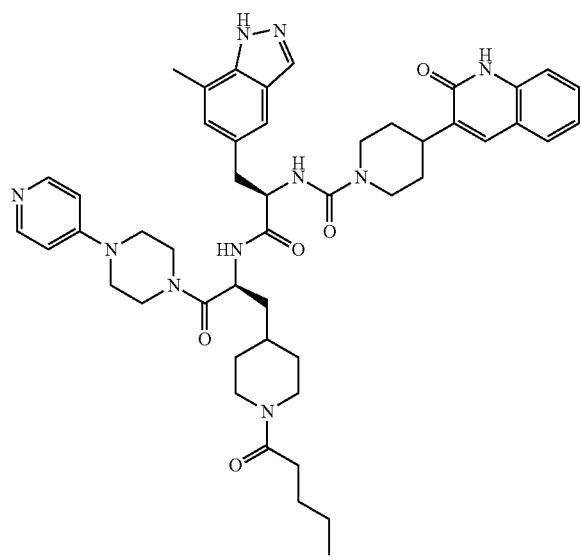
(7)
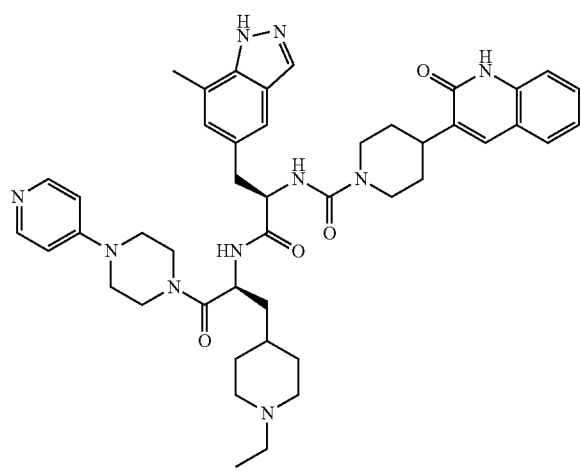
(8)
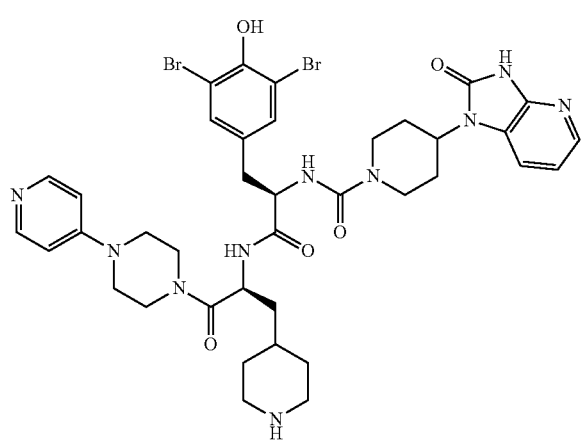
(9)
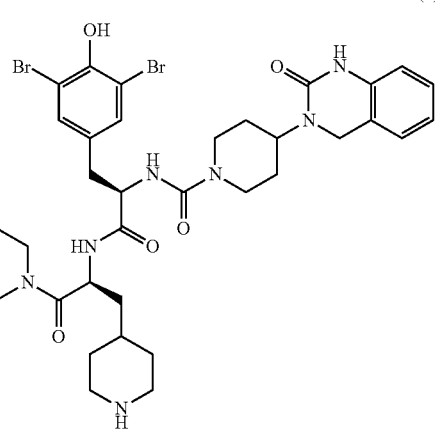
(10)
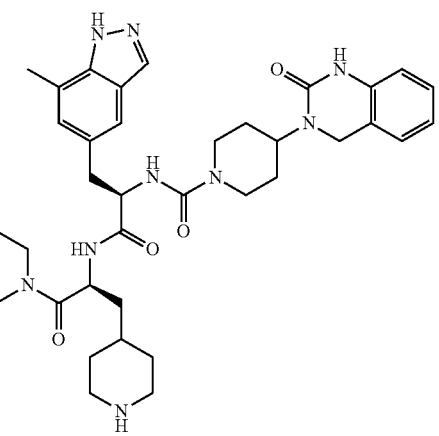
(11)
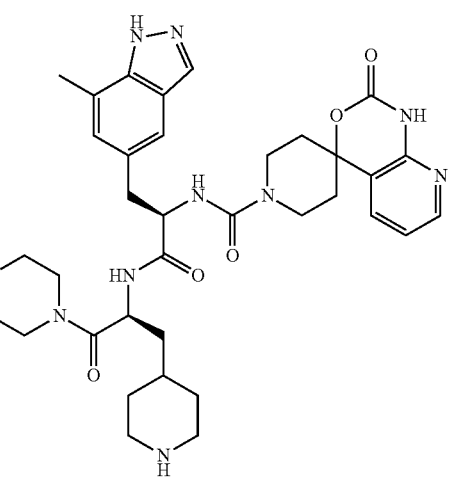

-continued (12)

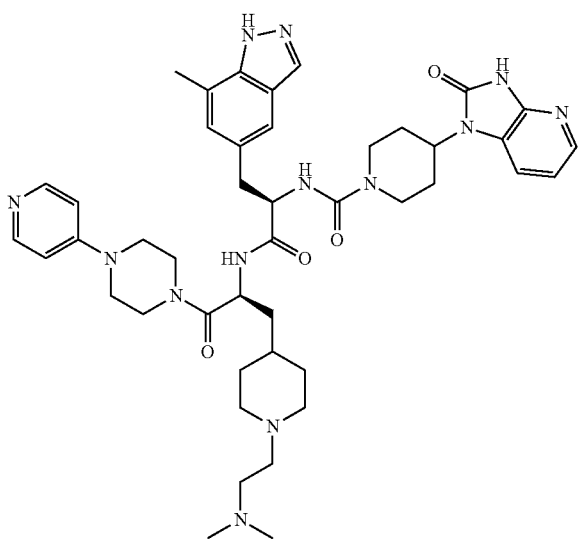

(13)

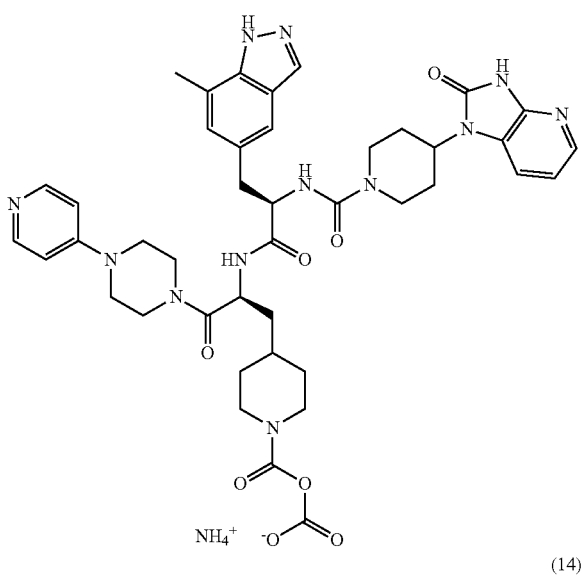

(14)

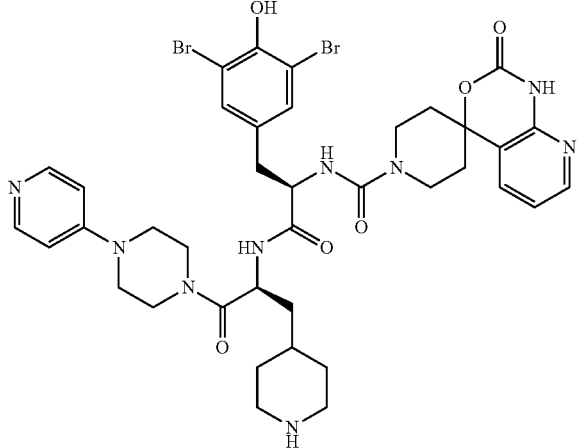

The NMR and LCMS properties as well as the biological activities of these compounds are set out in Tables 2 and 3.

To the extent that any of the compounds described have chiral centres, the present invention extends to all optical isomers of such compounds, whether in the form of racemates or resolved enantiomers. The invention described herein relates to all crystal forms, solvates and hydrates of any of the disclosed compounds however so prepared. To the extent that any of the compounds and intermediates disclosed herein have acid or basic centres such as carboxylates or amino groups, then all salt forms of said compounds are included herein. In the case of pharmaceutical uses, the salt should be seen as being a pharmaceutically acceptable salt.

Pharmaceutically acceptable salts that may be mentioned include acid addition salts and base addition salts. Such salts may be formed by conventional means, for example by reaction of a free acid or a free base form of a compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound in the form of a salt with another counter-ion, for example using a suitable ion exchange resin.

Examples of pharmaceutically acceptable salts include acid addition salts derived from mineral acids and organic acids, and salts derived from metals such as sodium, magnesium, or preferably, potassium and calcium.

Examples of acid addition salts include acid addition salts formed with acetic, 2,2-dichloroacetic, adipic, alginic, aryl sulfonic acids (e.g. benzenesulfonic, naphthalene-2-sulfonic, naphthalene-1,5-disulfonic and p-toluenesulfonic), ascorbic (e.g. L-ascorbic), L-aspartic, benzoic, 4-acetamidobenzoic, butanoic, (+)-camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic (e.g. (−)-L-malic), malonic, (±)-DL-mandelic, metaphosphoric, methanesulfonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulfuric, tannic, tartaric (e.g. (+)-L-tartaric), thiocyanic, undecylenic and valeric acids.

Particular examples of salts are salts derived from mineral acids such as hydrochloric, hydrobromic, phosphoric, metaphosphoric, nitric and sulfuric acids; from organic acids, such as tartaric, acetic, citric, malic, lactic, fumaric, benzoic, glycolic, gluconic, succinic, arylsulfonic, pamoic acids; and from metals such as sodium, magnesium, or preferably, potassium and calcium.

Also encompassed are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

"Pharmaceutically functional derivatives" of compounds as defined herein includes ester derivatives and/or derivatives that have, or provide for, the same biological function and/or activity as any relevant compound of the invention. Thus, for the purposes of this invention, the term also includes prodrugs of compounds as defined herein.

The term "prodrug" of a relevant compound includes any compound that, following oral or parenteral administration, is metabolised in vivo to form that compound in an experimentally-detectable amount, and within a predetermined time (e.g. within a dosing interval of between 6 and 24 hours (i.e. once to four times daily)).

Prodrugs of compounds may be prepared by modifying functional groups present on the compound in such a way that the modifications are cleaved, in vivo when such prodrug is administered to a mammalian subject. The modifications typically are achieved by synthesizing the parent compound with a prodrug substituent. Prodrugs include compounds wherein a hydroxyl, amino, sulfhydryl, carboxyl or carbonyl group in a compound is bonded to any group that may be cleaved in vivo to regenerate the free hydroxyl, amino, sulfhydryl, carboxyl or carbonyl group, respectively.

Examples of prodrugs include, but are not limited to, esters and carbamates of hydroxyl functional groups, ester groups of carboxyl functional groups, N-acyl derivatives and N-Mannich bases. General information on prodrugs may be found e.g. in Bundegaard, H. "Design of Prodrugs" p. 1-92, Elsevier, New York-Oxford (1985).

Definitions $C_1$-$C_6$ Alkyl

Alkyl means an aliphatic hydrocarbon group. The alkyl group may be straight or branched. "Branched" means that at least one carbon branch point is present in the group, for example isopropyl or tertiarybutyl. $C_1$-$C_3$ alkyl groups include methyl, ethyl, n-propyl, i-propyl. The alkyl group may be optionally substituted.

Heterocyclic

Heterocyclic means a cyclic group which may be aromatic in which at least one ring member is other than carbon. For example, at least one ring member (for example one, two or three ring members) may be selected from nitrogen, oxygen and sulphur. The point of attachment of heteroaryl groups may be via any atom of the ring system. Exemplary heteroaryl groups include pyridyl, indazolyl, 1,4-dihydro-2H-pyrido[2,3-d][1,3]oxazin-2-one, 1,3-dihydro-2H-imidazo[4,5-b]pyridin-2-one, 3,4-dihydroquinazolin-2(1H)-one, quinolin-2(1H)-one, piperidinyl, piperazinyl, and the like.

Optionally Substituted

"Optionally substituted" as applied to any group means that the said group may if desired be substituted with one or more substituents, which may be the same or different.

The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may take the form, for example, of tablets, dragees, powders, elixirs, syrups, liquid preparations including suspensions, sprays, inhalants, tablets, lozenges, emulsions, solutions, cachets, granules, capsules and suppositories, as well as liquid preparations for injections, including liposome preparations.

The dosages may be varied depending upon the requirements of the patient, the severity of the condition being treated, and the compound being employed. Determination of the proper dosage for a particular situation is within the skill of the art. Generally, treatment is initiated with the smaller dosages which are less than the optimum dose of the compound. Thereafter the dosage is increased by small increments until the optimum effect under the circumstances is reached. For convenience, the total daily dosage may be divided and administered in portions during the day if desired.

The magnitude of an effective dose of a compound will, of course, vary with the nature of the severity of the condition to be treated and with the particular compound and its route of administration. The selection of appropriate dosages is within the ability of one of ordinary skill in this art, without undue burden. In general, the daily dose range may be from about 10 μg to about 30 mg per kg body weight of a human and non-human animal, preferably from about 50 μg to about 30 mg per kg of body weight of a human and non-human animal, for example from about 50 μg to about 10 mg per kg of body weight of a human and non-human animal, for example from about 100 μg to about 30 mg per kg of body weight of a human and non-human animal, for example from about 100 μg to about 10 mg per kg of body weight of a human and non-human animal and most preferably from about 100 μg to about 1 mg per kg of body weight of a human and non-human animal.

Preparation of the Compounds of the Invention

Compounds of the invention may be prepared by procedures including those in Scheme 1. Details of many of the standard transformations such as those in the routes below and others which could be used to perform the same transformations can be found in standard reference textbooks such as "Organic Synthesis", M. B. Smith, McGraw-Hill (1994) or "Advanced Organic Chemistry", 4th edition, J. March, John Wiley & Sons (1992).

Scheme 1
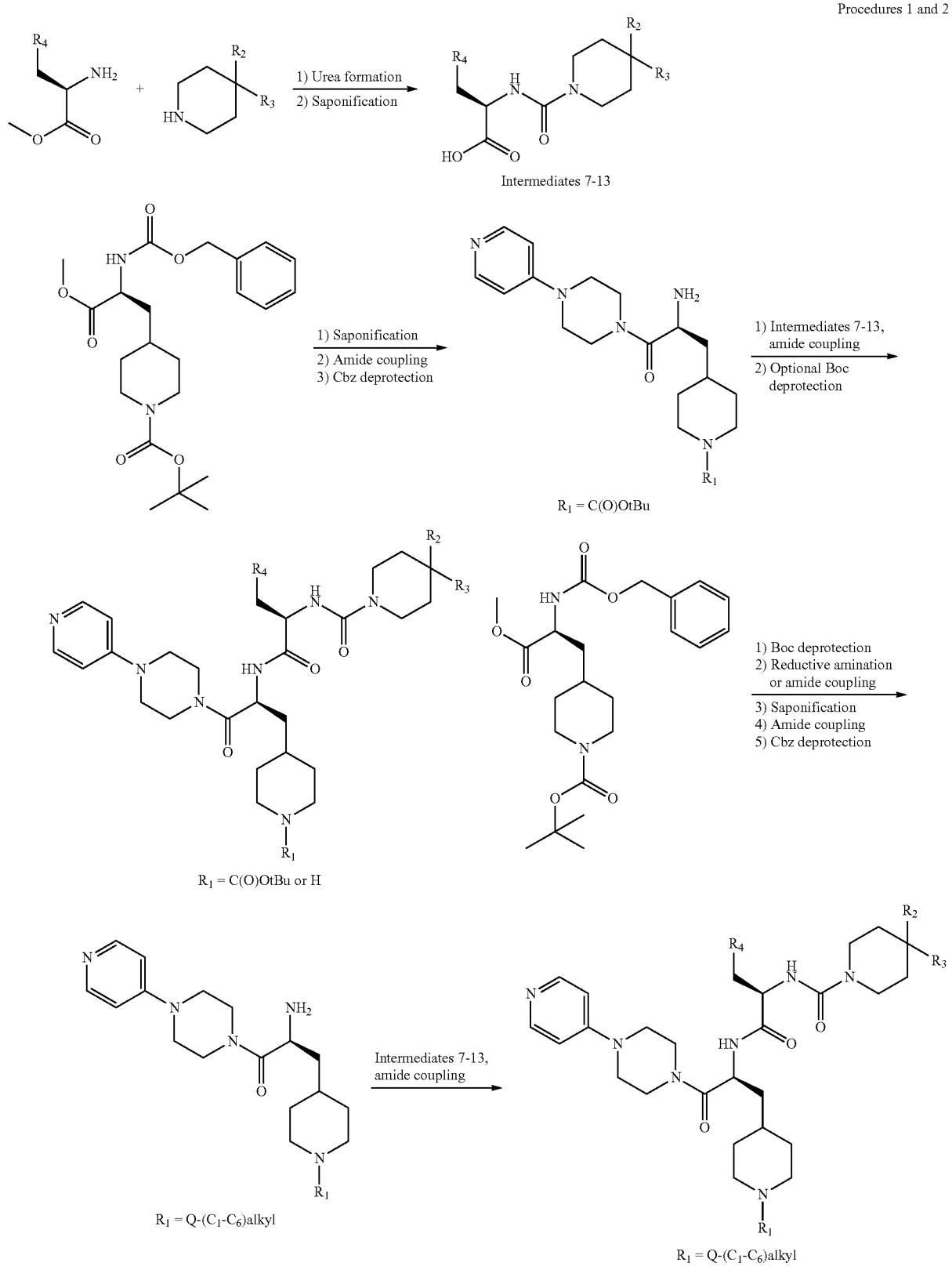
Procedures 1 and 2

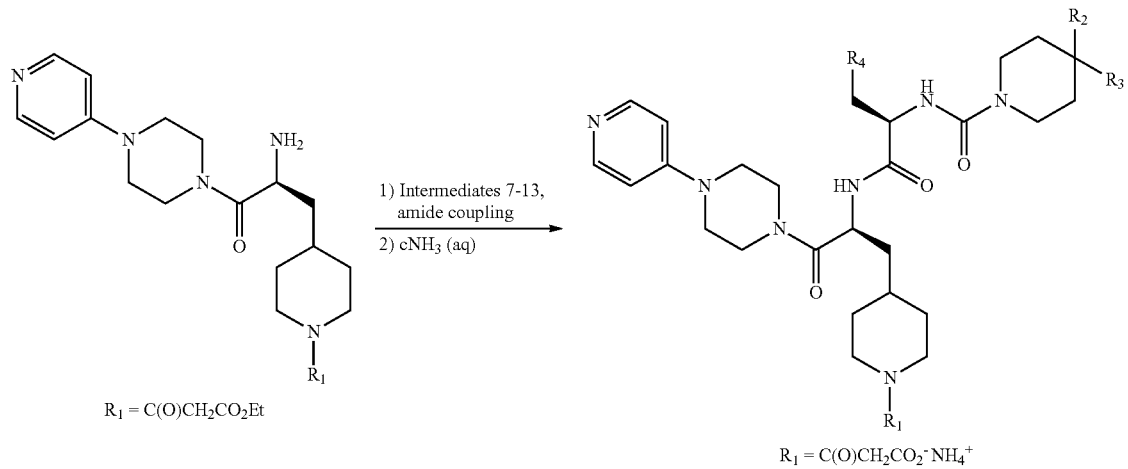

Procedure 3

Urea formations between amino acid intermediates, for example methyl esters of amino acids, and amine intermediates can be formed under conditions using a coupling agent such as DSC or CDI in the presence of a base such as triethylamine or DIPEA in solvents such as DMF and/or DCM. The methyl ester portion of the subsequently formed urea derivatives can be saponified using aqueous bases such as lithium hydroxide or sodium hydroxide in a suitable solvent such as THF, MeOH, 1,4-dioxane, EtOAc or a mixture thereof. The acid intermediates thus formed can be converted into amide examples under standard conditions, for example using a coupling agent such as HATU or HBTU, in the presence of a base such as DIPEA in a suitable solvent such as DMF. Alternatively an acid chloride can be coupled with an amine to yield an amide, in the presence of a base such as $Et_3N$, in a suitable solvent such as DCM. The amine partners for such amide couplings can be prepared using an appropriate combination of standard transformations (for example reductive aminations using an amine, an aldehyde or ketone, and a reducing agent such as sodium triacetoxyborohydride in a solvent such as DCM in the presence of acetic acid; or amide formation under conditions such as those detailed above) and removal of standard protecting groups under conditions which can be found in reference textbooks, for example "Protecting Groups", 3$^{rd}$ edition, P. J. Kocieński, Georg Thieme Verlag (2005). One such transformation is the removal of a tert-butoxycarbonyl group (commonly known as a Boc group) from an amine under acidic conditions such as HCl in a solvent such as 1,4-dioxane, MeOH, EtOH, DCM or combinations thereof. It can be appreciated that Boc deprotection of amine intermediates of the invention which possess additional basic centres may result in hydrochloride salts of different stoichiometries. For example the Boc deprotection of an intermediate with one additional basic centre will result in the formation of a new amine intermediate which is for example the mono-hydrochloride or di-hydrochloride salt, which will often be used without neutralisation of the hydrochloride salt to produce the free base of the intermediate, as it can be appreciated that in the subsequent amide formation an excess of a base such as DIPEA or triethylamine is typically used to neutralise the hydrochloride salt. Amine intermediates of the invention formed by Boc-deprotection which are used without neutralisation to the free base are named herein as the hydrochloride (x HCl), and the present invention extends to all salt forms of the said intermediates. Another such protecting group removal is the deprotection of a carbobenzyloxy-protected amine (commonly known as a Cbz or Z group) using reductive conditions such as catalysis by palladium on carbon in a solvent such as EtOH in the presence of gaseous $H_2$ or by using a commercially available hydrogenation reactor which combines continuous-flow chemistry with in-situ hydrogen generation (for example an H-Cube hydrogenation reactor, ThalesNano Nanotechnology Inc., Budapest, Hungary). Alternative conditions for the removal of a Cbz-protecting group include transfer hydrogenation, for example using a palladium on carbon catalyst in the presence of ammonium formate or cyclohexa-1,4-diene, or both ammonium formate and cyclohexa-1,4-diene, in a solvent such as EtOH or aqueous EtOH at an elevated temperature such as 70° C.

General Procedures

Where no preparative routes are included, the relevant intermediate is commercially available. Commercial reagents were utilized without further purification. Room temperature (rt) refers to approximately 20-27° C. $^1$H NMR spectra were recorded at 400 MHz on Bruker, Varian or JEOL instruments. Chemical shift values are expressed in parts per million (ppm), i.e. (δ)-values. The following abbreviations are used for the multiplicity of the NMR signals: s=singlet, br=broad, d=doublet, t=triplet, q=quartet, quin=quintet, h=heptet, dd=doublet of doublets, dt=double of triplets, m=multiplet. Coupling constants are listed as J values, measured in Hz. NMR and mass spectroscopy results were corrected to account for background peaks. Chromatography refers to column chromatography performed using silica and executed under positive pressure (flash chromatography) conditions. LCMS experiments were carried out using electrospray conditions under the conditions below. LCMS data are given in the format: Mass ion, electrospray mode (positive or negative), retention time (experimental text and Table 1); Mass ion, electrospray mode (positive or negative), retention time, approximate purity (Table 2).

Method A.

Instruments: Hewlett Packard 1100 with G1315A DAD, Micromass ZQ; Column: Waters X-Bridge C-18, 2.5 micron, 2.1×20 mm or Phenomenex Gemini-NX C-18, 3 micron, 2.0×30 mm; Gradient [time (min)/solvent D in C (%)]: 0.00/2, 0.10/2, 8.40/95, 10.00/95; Solvents: solvent C=2.5 L H₂O+2.5 mL 28% ammonia in water solution; solvent D=2.5 L MeCN+135 mL H₂O+2.5 mL 28% ammonia in water solution; Injection volume 1 μL; UV detection 230 to 400 nM; column temperature 45° C.; Flow rate 1.5 mL/min.

Method B.

Instruments: Agilent Technologies 1260 Infinity LC with Chemstation software, Diode Array Detector, Agilent 6120B Single Quadrupole MS with API-ES Source; Column: Phenomenex Gemini-NX C-18, 3 micron, 2.0×30 mm; Gradient [time (min)/solvent D in C (%)]: 0.00/5, 2.00/95, 2.50/95, 2.60/5, 3.00/5; Solvents C and D are as described above in Method A; Injection volume 0.5 μL; UV detection 190 to 400 nM; column temperature 40° C.; Flow rate 1.5 mL/min.

Method C.

As detailed for method A, except with Gradient [time (min)/solvent D in C (%)]: 0.00/2, 0.10/2, 2.50/95, 3.50/95.

Method D.

Instruments: Acquity UPLC coupled with SQD mass spectrometer; Column: Acquity UPLC BEH C18, 1.7 micron, 2.1×50 mm; Gradient [time (min)/solvent B in A (%)]: 0.00/3, 1.50/100, 1.90/100, 2.00/3; Solvents: solvent A=10 mM aqueous solution of NH₄HCO₃ (adjusted to pH 10 with ammonia); solvent B=MeCN; Injection volume 1 μL; UV detection 210 to 350 nM; column temperature 40° C.; Flow rate 0.9 mL/min.

Abbreviations

CDI=1,1'-carbonyldiimidazole
DCM=dichloromethane
DIPEA=N,N-diisopropylethylamine
DMAC=N,N-dimethylacetamide
DMF=dimethylformamide
DSC=N,N'-disuccinimidyl carbonate
DMSO=dimethylsulfoxide
ES=electrospray
EtOAc=ethyl acetate
h=hour(s)
HATU=1-[bis(dimethylamino)methylene]-1H-1,2,3-triazolo[4,5-b]pyridinium 3-oxid hexafluorophosphate
HBTU=N,N,N',N'-tetramethyl-O-(1H-benzotriazol-1-yl) uronium hexafluorophosphate
L=liter
LC=liquid chromatography
LCMS=liquid chromatography mass spectrometry
MeCN=acetonitrile
min=minute(s)
MS=mass spectrometry
NMR=nuclear magnetic resonance
rcf=relative centrifugal force
rpm=revolutions per minute
rt=room temperature
s=second(s)
TFA=trifluoroacetic acid
THF=tetrahydrofuran Prefixes n-, s-, i-, t- and tert- have their usual meanings: normal, secondary, iso, and tertiary.

Synthesis of Intermediates
Preparation of Carboxylic Acid Intermediates

Typical procedure for the preparation of carboxylic acid intermediates via urea formation and subsequent saponification, as exemplified by the preparation of Intermediate 7, (2R)-3-(7-methyl-1H-indazol-5-yl)-2-{[(2'-oxo-1',2'-dihydro-1H-spiro[piperidine-4,4'-pyrido[2,3-d][1,3]oxazin]-1-yl)carbonyl]amino}propanoic acid

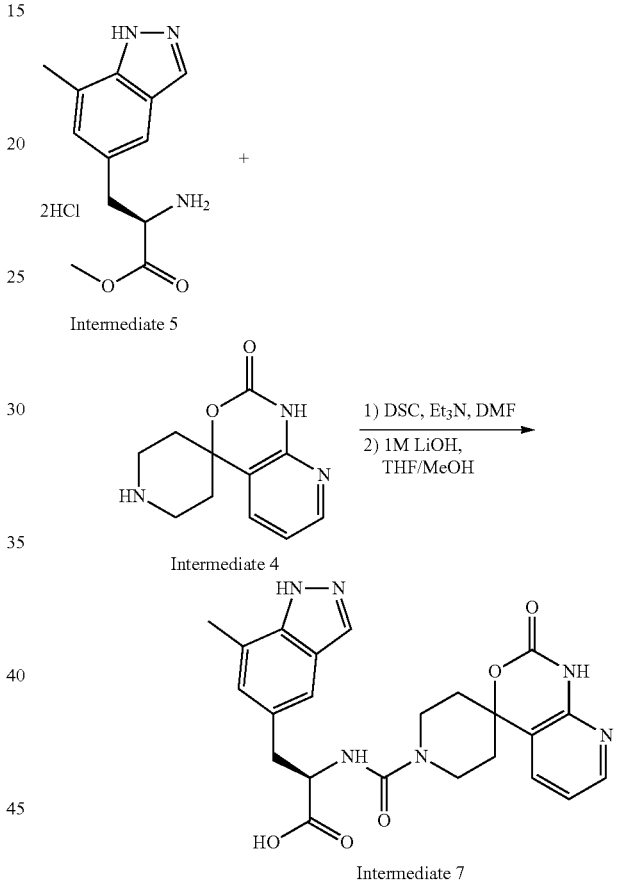

Step 1) Et₃N (2.26 mL, 16.3 mmol) was added to a solution of (R)-methyl 2-amino-3-(7-methyl-1H-indazol-5-yl)propanoate dihydrochloride (Intermediate 5, 995 mg, 3.3 mmol) and DSC (917 mg, 3.6 mmol) in DMF (20 mL) and the mixture stirred at rt for 30 min. Spiro[piperidine-4,4'-[4H]pyrido[2,3-d][1,3]oxazin]-2'(1'H)-one (Intermediate 4, 785 mg, 3.6 mmol) was then added portionwise and the reaction mixture stirred at rt for 18 h before concentration in vacuo. The residue was partitioned between H₂O and MeOH/DCM (1:9), the phases were separated and the aqueous layer was washed with H₂O. Residual solid from the separation step was dissolved in MeOH and the combined organic layers were concentrated in vacuo and purified by flash chromatography, eluting with EtOAc in MeOH (20:1), to yield methyl (2R)-3-(7-methyl-1H-indazol-5-yl)-2-{[(2'-oxo-1',2'-dihydro-1H-spiro[piperidine-4,4'-pyrido[2,3-d][1,3]oxazin]-1-yl)carbonyl]amino}propanoate (1.06 g, 2.22 mmol) as a white solid.

LCMS (Method A): m/z 479.3 (ES+), at 2.61 min, 100%.

$^1$H NMR: (400 MHz, DMSO-$d_6$) δ: 1.59-1.75 (m, 2H), 1.78-1.90 (m, 2H), 2.45 (s, 3H), 2.90-3.08 (m, 4H), 3.59 (s, 3H), 3.86-3.96 (m, 2H), 4.28-4.38 (m, 1H), 6.94-7.06 (m, 3H), 7.32 (dd, J=7.4, 1.2, 1H), 7.39 (s, 1H), 7.95 (s, 1H), 8.18 (dd, J=5.1, 1.6, 1H), 10.79 (s, 1H), 13.04 (s, 1H).

Step 2) Methyl (2R)-3-(7-methyl-1H-indazol-5-yl)-2-{[(2'-oxo-1',2'-dihydro-1H-spiro[piperidine-4,4'-pyrido[2,3-d][1,3]oxazin]-1-yl)carbonyl]amino}propanoate (1.06 g, 2.22 mmol) was dissolved in THF (15 mL) and MeOH (3 mL) and an aqueous solution of LiOH (1M, 4.4 mL, 4.4 mmol) was added dropwise. After stirring at rt for 3.5 h further aqueous LiOH (1M, 2.2 mL, 2.2 mmol) was added dropwise and the mixture stirred for 1 h at rt before concentration under a stream of nitrogen. The residue was dissolved in a minimum volume of H$_2$O and cooled to 0° C. Aqueous 1M HCl was added dropwise to adjust the pH to ≤3 and the resulting precipitate was isolated by filtration, washed with cold H$_2$O and Et$_2$O to yield the title compound (877 mg, 1.89 mmol) as a pale yellow solid.

Data in Table 1.

Intermediate 8, (2R)-3-(7-methyl-1H-indazol-5-yl)-2-({[4-(2-oxo-2,3-dihydro-1H-imidazo[4,5-b]pyridin-1-yl)piperidin-1-yl]carbonyl}amino)propanoic acid

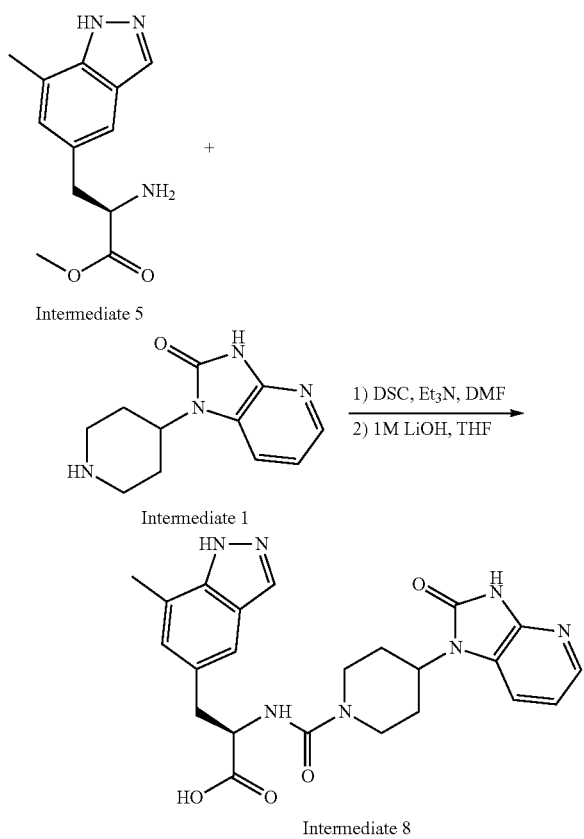

The title compound (1.50 g, 3.2 mmol) was prepared over two steps from (R)-methyl 2-amino-3-(7-methyl-1H-indazol-5-yl)propanoate (Intermediate 5, 1.00 g, 4.3 mmol) and 1-(piperidin-4-yl)-1,3-dihydro-2H-imidazo[4,5-b]pyridin-2-one (Intermediate 1, 1.02 g, 4.7 mmol) using the methods of Intermediate 7.

Data in Table 1.

Intermediate 14, 3,5-dibromo-N-[(2'-oxo-1',2'-dihydro-1H-spiro[piperidine-4,4'-pyrido[2,3-d][1,3]oxazin]-1-yl)carbonyl]-D-tyrosine

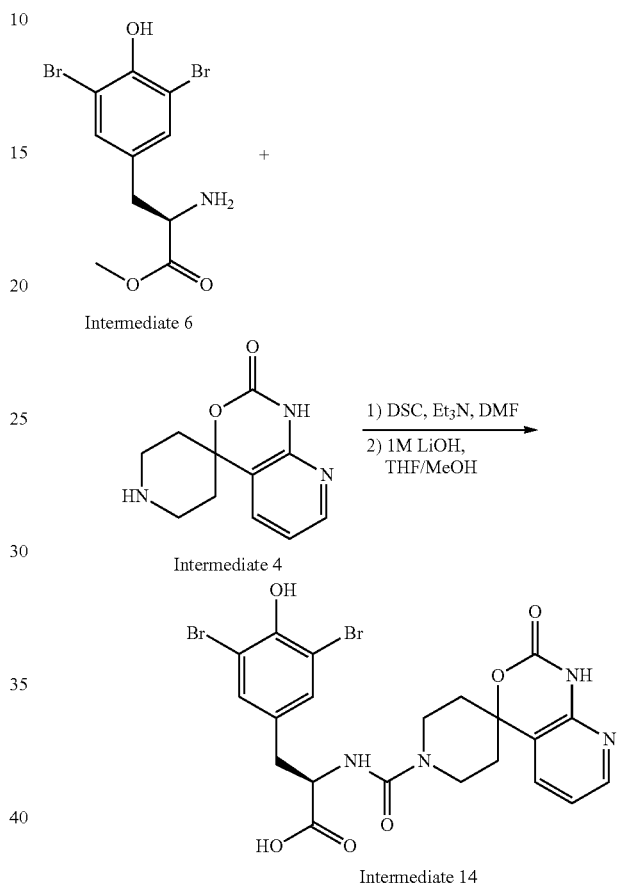

The title compound (561 mg, 1.0 mmol) was prepared over two steps from 3, 5-dibromo-D-tyrosine methyl ester (Intermediate 6, 530 mg, 1.5 mmol) and spiro[piperidine-4,4'-[4H]pyrido[2,3-d][1,3]oxazin]-2'(1'H)-one (Intermediate 4, 362 mg, 1.7 mmol) using the methods of Intermediate 7.

Data in Table 1.

Intermediate 11, 3,5-dibromo-N-{[4-(2-oxo-2,3-dihydro-1H-imidazo[4,5-b]pyridin-1-yl)piperidin-1-yl]carbonyl}-D-tyrosine

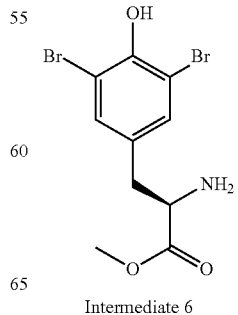

Intermediate 6

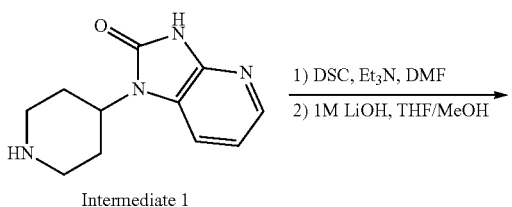

Intermediate 1

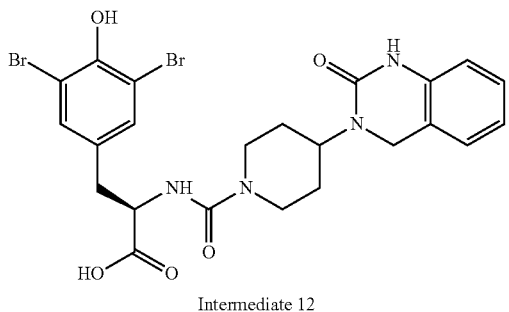

Intermediate 12

The title compound (224 mg, 0.38 mmol) was prepared over two steps from 3,5-dibromo-D-tyrosine methyl ester (Intermediate 6, 353 mg, 1.00 mmol) and 3-(piperidin-4-yl)-3,4-dihydroquinazolin-2(1H)-one (Intermediate 3, 254 mg, 1.10 mmol) using the methods of Intermediate 7.

Data in Table 1.

Intermediate 13, (2R)-3-(7-methyl-1H-indazol-5-yl)-2-({[4-(2-oxo-1,4-dihydroquinazolin-3(2H)-yl)piperidin-1-yl]carbonyl}amino)propanoic acid

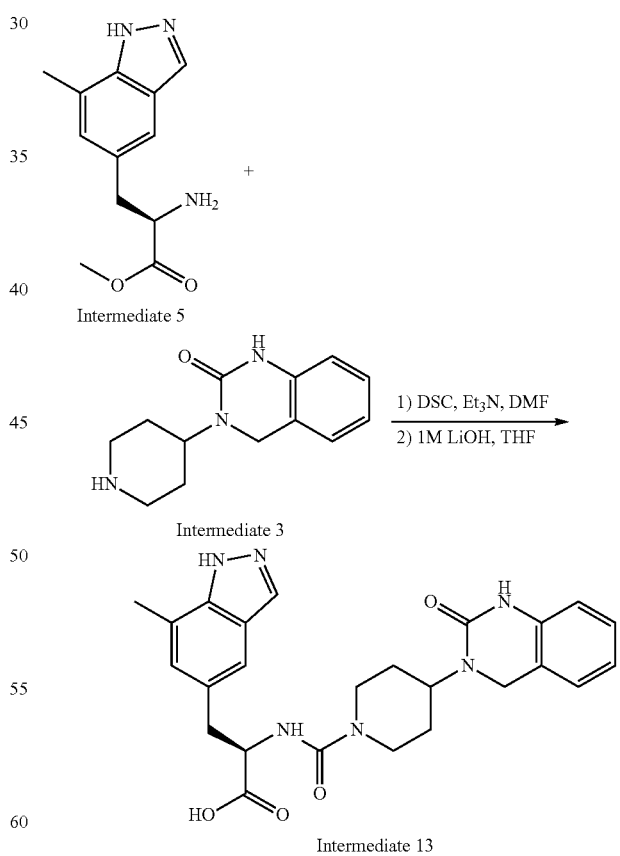

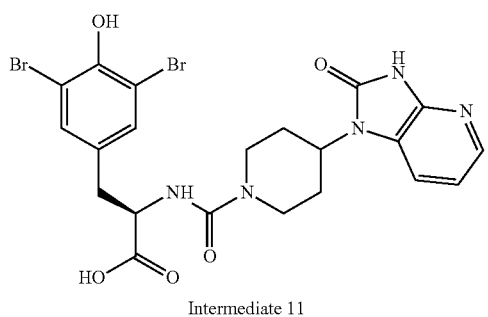

Intermediate 11

The title compound (214 mg, 0.37 mmol) was prepared over two steps from 3,5-dibromo-D-tyrosine methyl ester (Intermediate 6, 357 mg, 1.01 mmol) and 1-(piperidin-4-yl)-1,3-dihydro-2H-imidazo[4,5-b]pyridin-2-one (Intermediate 1, 362 mg, 1.42 mmol) using the methods of Intermediate 7.

Data in Table 1.

Intermediate 12, 3,5-dibromo-N-{[4-(2-oxo-1,4-dihydroquinazolin-3(2H)-yl)piperidin-1-yl]carbonyl}-D-tyrosine

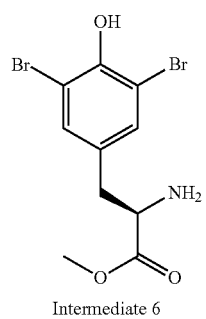

Intermediate 6

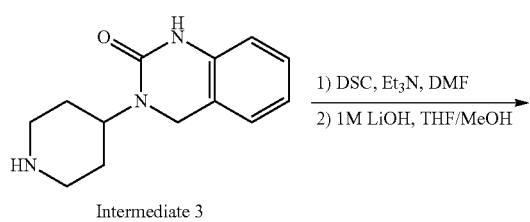

Intermediate 3

The title compound (561 mg, 1.18 mmol) was prepared over two steps from (R)-methyl 2-amino-3-(7-methyl-1H-indazol-5-yl)propanoate (Intermediate 5, 917 mg, 3.93 mmol) and 3-(piperidin-4-yl)-3,4-dihydroquinazolin-2(1H)- one (Intermediate 3, 1.00 g, 4.32 mmol) using the methods of Intermediate 7.
Data in Table 1.

Intermediate 10, 3,5-dibromo-N-{[4-(2-oxo-1,2-dihydroquinolin-3-yl)piperidin-1-yl]carbonyl}-D-tyrosine

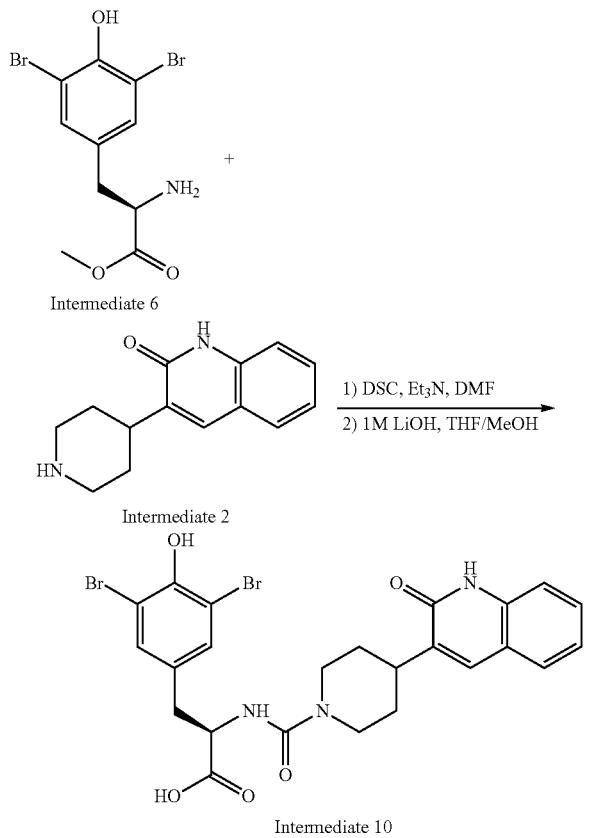

The title compound (77 mg, 0.13 mmol) was prepared over two steps from 3, 5-dibromo-D-tyrosine methyl ester (Intermediate 6, 103 mg, 0.29 mmol) and 3-(piperidin-4-yl)quinolin-2(1H)-one (Intermediate 2, 73 mg, 0.32 mmol) using the methods of Intermediate 7.
Data in Table 1.

Intermediate 9, (2R)-3-(7-methyl-1H-indazol-5-yl)-2-({[4-(2-oxo-1,2-dihydroquinolin-3-yl)piperidin-1-yl]carbonyl}amino)propanoic acid

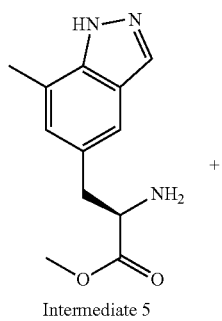

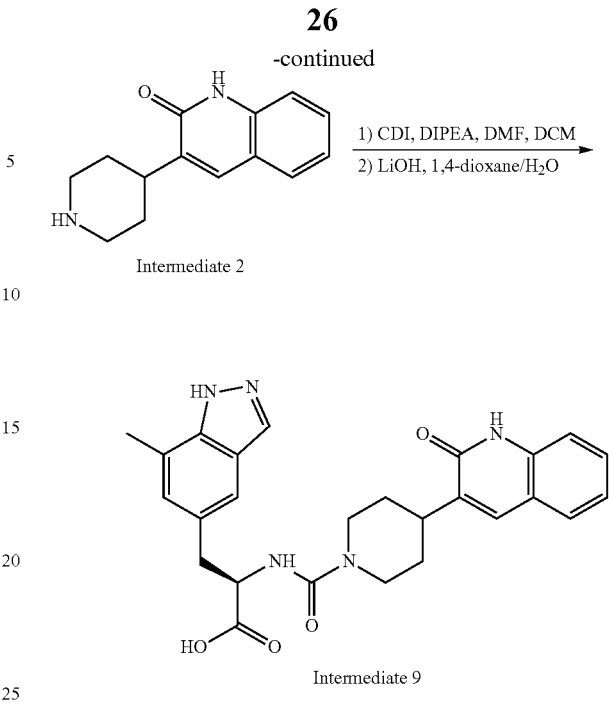

Step 1) To a solution of (R)-methyl 2-amino-3-(7-methyl-1H-indazol-5-yl) propanoate (Intermediate 5, 6.05 g, 25.9 mmol) in DMF (60 mL) under $N_2$ at approximately −20° C. was added CDI (8.40 g, 51.8 mmol) and the mixture was stirred for 15 mins while keeping the temperature below −10° C. A solution of $H_2O$ (2.34 mL) in a few mL of DMF was added and stirring continued for 15 mins while keeping the temperature below −10° C. 3-(Piperidin-4-yl)quinolin-2 (1H)-one (Intermediate 2, 6.99 g, 30.6 mmol), DIPEA (4.93 mL, 28.2 mmol) and DCM (20 mL) were then added in that order and the mixture was heated to 40° C. under $N_2$ for 12 h. After cooling to rt, 2M HCl (aq) (38.7 mL) was added and the mixture was extracted twice with DCM. The combined organic extracts were washed three times with $H_2O$, dried ($Na_2SO_4$) and concentrated in vacuo. Purification by flash chromatography, eluting with MeOH/DCM (5:95), yielded methyl (2R)-3-(7-methyl-1H-indazol-5-yl)-2-({[4-(2-oxo-1,2-dihydroquinolin-3-yl)piperidin-1-yl]carbonyl}amino)propanoate (10.4 g, 21.3 mmol) as a light tan solid.

$^1$H NMR: (400 MHz, $CDCl_3$) δ: 1.40-1.60 (m, 2H), 1.95-1.97 (m, 2H), 2.46 (s, 3H), 2.90-3.00 (m, 2H), 3.11-3.26 (m, 3H), 3.76 (s, 3H), 4.07-4.12 (m, 2H), 4.86-4.91 (m, 1H), 5.18 (d, J=7.6, 1H), 6.93 (s, 1H), 7.17-7.21 (m, 1H), 7.24 (s, 1H), 7.32 (s, 1H), 7.43-7.54 (m, 3H), 7.95 (s, 1H), 10.70 (s, 2H).

Step 2) To a solution of methyl (2R)-3-(7-methyl-1H-indazol-5-yl)-2-({[4-(2-oxo-1,2-dihydroquinolin-3-yl)piperidin-1-yl]carbonyl}amino)propanoate (9.79 g, 20.1 mmol) in 1,4-dioxane (150 mL) was added a solution of LiOH.$H_2O$ (1.26 g, 30.0 mmol) in $H_2O$ (150 mL) and the mixture was stirred at rt for 2 h. The reaction mixture was concentrated in vacuo to near-dryness and re-dissolved in $H_2O$ before being acidified with aqueous 2M HCl (approximately 15 mL) whilst being rapidly stirred. The resulting thick white precipitate was isolated by filtration and washed with $H_2O$ until the washings were near neutral pH. Drying in vacuo yielded the title compound (8.11 g, 17.1 mmol) as an off-white solid.
Data in Table 1.
Preparation of Amine Intermediates Intermediate 17, tert-butyl 4-{(2S)-2-amino-3-oxo-3-[4-(pyridin-4-yl)piperazin-1-yl]propyl}piperidine-1-carboxylate

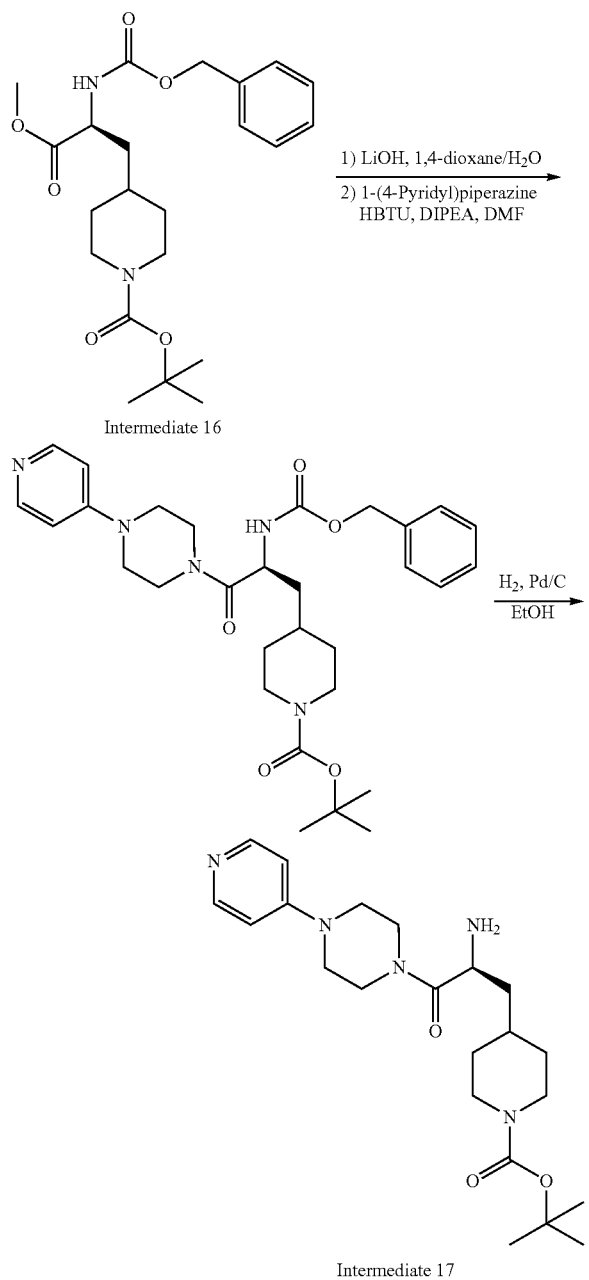

Intermediate 17

Step 1) To a solution of tert-butyl 4-[(2S)-2-{[(benzyloxy)carbonyl]amino}-3-methoxy-3-oxopropyl]piperidine-1-carboxylate (Intermediate 16, 4.29 g, 10.2 mmol) in 1,4-dioxane (50 mL) was added a solution of LiOH.H$_2$O (856 mg, 20.4 mmol) in H$_2$O (50 mL) and the mixture was stirred for 5 h. The reaction mixture was concentrated in vacuo to near-dryness and re-dissolved in H$_2$O before being acidified with 0.5 M NaHSO$_4$ (aq). The resulting thick white precipitate was extracted into EtOAc and the combined organic layers were washed with brine, dried (MgSO$_4$) and concentrated in vacuo to yield N-[(benzyloxy)carbonyl]-3-[1-(tert-butoxycarbonyl)piperidin-4-yl]-L-alanine as a white foam (4.01 g, 9.87 mmol).

$^1$H NMR: (400 MHz, DMSO-d$_6$) δ: 0.85-1.07 (m, 2H), 1.39 (s, 9H), 1.45-1.68 (m, 5H), 2.55-2.71 (m, 2H), 3.86-3.94 (m, 1H), 4.85-4.98 (m, 2H), 5.04 (s, 2H), 7.28-7.39 (m, 5H), 7.53 (d, J=8.3, 1H), 12.5 (br s, 1H).

Step 2) To a solution of N-[(benzyloxy)carbonyl]-3-[1-(tert-butoxycarbonyl)piperidin-4-yl]-L-alanine (4.00 g, 9.84 mmol) in DMF (80 mL) was added HBTU (4.10 g, 10.81 mmol) followed by DIPEA (3.74 mL, 21.47 mmol) and 1-(4-pyridyl)piperazine (Intermediate 15, 1.69 g, 10.35 mmol) and the mixture was stirred at rt for 3 h. The reaction mixture was concentrated in vacuo to near-dryness and the residue dissolved in EtOAc, washed twice with H$_2$O, twice with NaHCO$_3$ (aq) and brine, dried (Na$_2$SO$_4$) and concentrated in vacuo. Purification by flash chromatography, eluting with MeOH/DCM (5:95), yielded tert-butyl 4-{(2S)-2-{[(benzyloxy)carbonyl]amino}-3-oxo-3-[4-(pyridin-4-yl)piperazin-1-yl]propyl}piperidine-1-carboxylate (4.51 g, 8.18 mmol) as an off-white foam.

$^1$H NMR: (400 MHz, CDCl$_3$) δ: 1.07-1.16 (br m, 2H), 1.44 (s, 9H), 1.54-1.60 (br m, 2H), 1.88-1.91 (m, 1H), 2.62-2.65 (br m, 2H), 3.47-3.65 (br m, 6H), 3.81-3.86 (br m, 2H), 4.05 (br m, 2H), 4.26 (br m, 2H), 4.70-4.74 (m, 1H), 5.04-5.12 (m, 2H), 5.70 (d, J=8.8, 1H), 6.82 (d, J=6.0, 2H), 7.26-7.34 (m, 5H), 8.10 (br s, 2H).

Step 3) A solution of tert-butyl 4-{(2S)-2-{[(benzyloxy)carbonyl]amino}-3-oxo-3-[4-(pyridin-4-yl)piperazin-1-yl]propyl}piperidine-1-carboxylate (557 mg, 1.01 mmol) in EtOH (20 mL) was eluted five times through a Pd/C cartridge at 50° C. using a continuous flow hydrogenation reactor (H-Cube, ThalesNano Nanotechnology Inc., Budapest, Hungary) in the presence of H$_2$ (full H$_2$ mode), monitoring conversion to desired product by LCMS. Upon >95% conversion the reaction mixture was concentrated in vacuo to yield the title compound (455 mg, 1.09 mmol) as a yellow glassy solid.
Data in Table 1.

Intermediate 18, methyl N-[(benzyloxy)carbonyl]-3-(1-propylpiperidin-4-yl)-L-alaninate

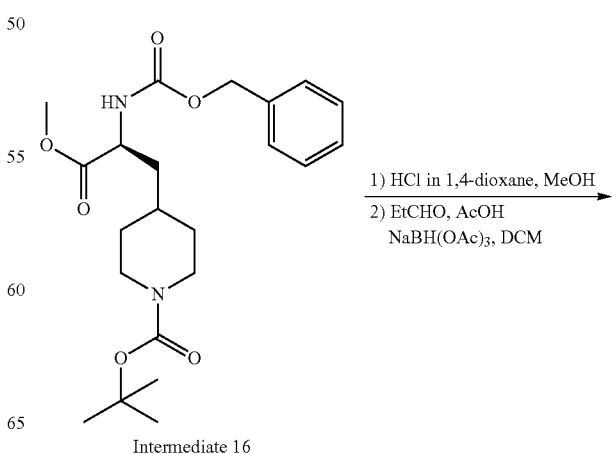

Intermediate 16

-continued

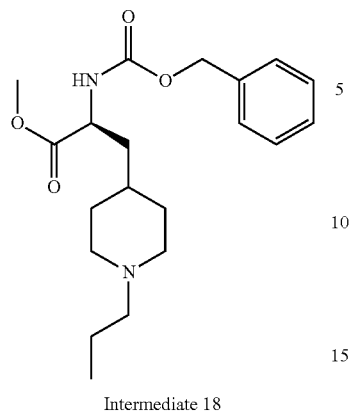

Intermediate 18

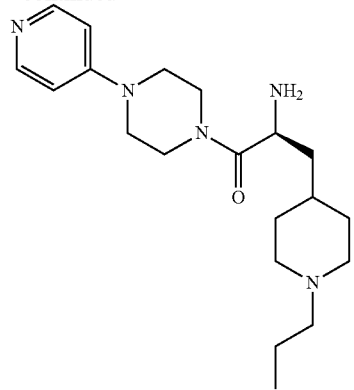

Intermediate 19

Step 1) HCl in 1,4-dioxane (4M, 10 mL, 40 mmol) was added to a solution of tert-butyl 4-[(2S)-2-{[(benzyloxy)carbonyl]amino}-3-methoxy-3-oxopropyl]piperidine-1-carboxylate (Intermediate 16, 1.00 g, 2.38 mmol) in MeOH (10 mL). After stirring at rt for 2 h the reaction mixture was concentrated in vacuo to yield methyl N-[(benzyloxy)carbonyl]-3-piperidin-4-yl-L-alaninate hydrochloride (850 mg) which was used without purification in the subsequent step.

LCMS (Method C): m/z 321.2 (ES$^+$) at 1.66 min.

Step 2) A mixture of methyl N-[(benzyloxy)carbonyl]-3-piperidin-4-yl-L-alaninate hydrochloride (500 mg, 1.40 mmol), propionaldehyde (120 μL, 1.68 mmol) and glacial acetic acid (96 μL, 1.68 mmol) in DCM (10 mL) was stirred at rt for 1 h, before the addition of sodium triacetoxyborohydride (356 mg, 1.68 mmol). After stirring overnight at rt the mixture was concentrated in vacuo and purified by flash column chromatography, eluting with 0-10% MeOH in DCM to yield the title compound (400 mg, 1.10 mmol) as a colourless oil.

Data in Table 1.

Intermediate 19, (2S)-2-amino-3-(1-propylpiperidin-4-yl)-1-[4-(pyridin-4-yl)piperazin-1-yl]propan-1-one

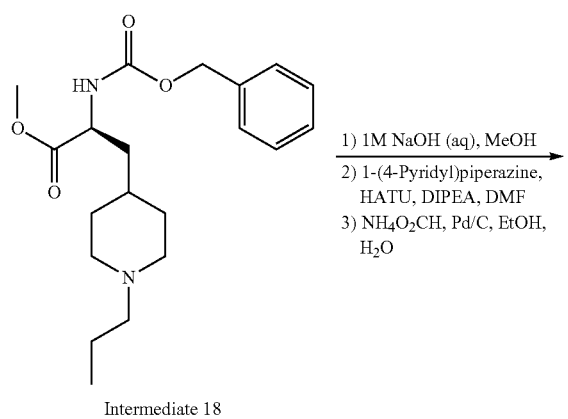

Intermediate 18

1) 1M NaOH (aq), MeOH
2) 1-(4-Pyridyl)piperazine, HATU, DIPEA, DMF
3) NH$_4$O$_2$CH, Pd/C, EtOH, H$_2$O Step 1) Aqueous sodium hydroxide (1M, 5 mL, 5.0 mmol) was added to a solution of methyl N-[(benzyloxy)carbonyl]-3-(1-propylpiperidin-4-yl)-L-alaninate (Intermediate 18, 400 mg, 1.10 mmol) in MeOH (5 mL). After stirring at rt overnight the reaction mixture was partially concentrated in vacuo to remove MeOH and acidified to pH ≤2 with 1M aqueous HCl. Concentration in vacuo yielded crude N-[(benzyloxy)carbonyl]-3-(1-propylpiperidin-4-yl)-L-alanine (385 mg) which was used without purification in the subsequent step.

LCMS (Method B): m/z 349.0 (ES$^+$) at 0.79 min.

Step 2) A mixture of crude N-[(benzyloxy)carbonyl]-3-(1-propylpiperidin-4-yl)-L-alanine (385 mg), 1-(4-pyridyl)piperazine (Intermediate 15, 215 mg, 1.32 mmol), HATU (505 mg, 1.33 mmol) and DIPEA (383 μL, 2.20 mmol) in DMF (5 mL) was stirred at rt for 3 h. Concentration in vacuo yielded benzyl {(2S)-1-oxo-3-(1-propylpiperidin-4-yl)-1-[4-(pyridin-4-yl)piperazin-1-yl]propan-2-yl}carbamate (542 mg) as a pale orange, viscous oil which was used without purification in the subsequent step.

LCMS (Method B): m/z 493.9 (ES$^+$) at 1.45 min.

Step 3) Ammonium formate (643 mg, 11.0 mmol) was added to a solution of benzyl {(2S)-1-oxo-3-(1-propylpiperidin-4-yl)-1-[4-(pyridin-4-yl)piperazin-1-yl]propan-2-yl}carbamate (crude, 542 mg) in EtOH (40 mL) and H$_2$O (10 mL). Palladium on carbon (10%, 10 mg) was added and the mixture was heated at 70° C. under N$_2$ overnight. After cooling to rt the mixture was filtered through celite and the filtrate concentrated in vacuo to yield the title compound as a yellow viscous oil (115 mg) which was used without purification in the formation of Example 4.

Data in Table 1.

Intermediate 20, 1-(4-{(2S)-2-amino-3-oxo-3-[4-(pyridin-4-yl)piperazin-1-yl]propyl}piperidin-1-yl)pentan-1-one

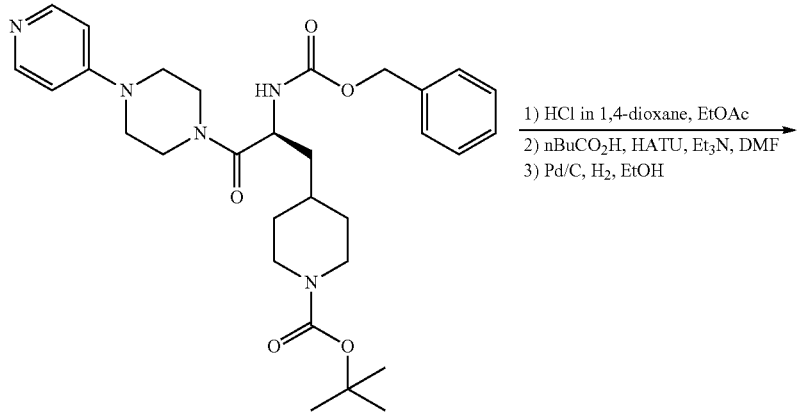

Intermediate 17, Step 2 product

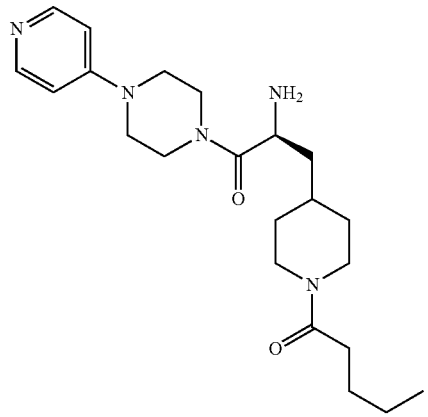

Intermediate 20

Step 1) HCl in 1,4-dioxane (4M, 2.30 mL, 9.20 mmol) was added to a solution of tert-butyl 4-{(2S)-2-{[(benzyloxy)carbonyl]amino}-3-oxo-3-[4-(pyridin-4-yl)piperazin-1-yl]propyl}piperidine-1-carboxylate (Intermediate 17, Step 2 product) (1.30 g, 2.30 mmol) in EtOAc (23 mL) and the mixture was stirred at rt overnight. After concentration in vacuo purification by flash column chromatography eluting with DCM/MeOH/7N NH$_3$ (90:5:5) in MeOH yielded benzyl {(2S)-1-oxo-3-(piperidin-4-yl)-1-[4-(pyridin-4-yl)piperazin-1-yl]propan-2-yl}carbamate (740 mg, 1.64 mmol).

LCMS (Method B): m/z 452.2 (ES$^+$) at 1.30 min.

Step 2) A mixture of pentanoic acid (137 mg, 0.36 mmol), benzyl {(2S)-1-oxo-3-(piperidin-4-yl)-1-[4-(pyridin-4-yl)piperazin-1-yl]propan-2-yl}carbamate (146 mg, 0.32 mmol), triethylamine (209 μL, 1.50 mmol) and HATU (137 mg, 0.36 mmol) in DMF (3 mL) was stirred at rt overnight. 1M aqueous sodium carbonate solution (20 mL) was added, the mixture was concentrated in vacuo and purified by gradient flash column chromatography, eluting with 0-10% (1:1 MeOH/7N NH$_3$ in MeOH) in DCM, to yield benzyl {(2S)-1-oxo-3-(1-pentanoylpiperidin-4-yl)-1-[4-(pyridin-4-yl)piperazin-1-yl]propan-2-yl}carbamate.

LCMS (Method B): m/z 536.2 (ES$^+$) at 1.38 min.

Step 3) A solution of benzyl {(2S)-1-oxo-3-(1-pentanoylpiperidin-4-yl)-1-[4-(pyridin-4-yl)piperazin-1-yl]propan-2-yl}carbamate in EtOH was eluted through a Pd/C cartridge at 50° C. using a continuous flow hydrogenation reactor (H-Cube, ThalesNano Nanotechnology Inc., Budapest, Hungary) in the presence of H$_2$ (full H$_2$ mode), monitoring conversion to desired product by LCMS. Upon >95% conversion the reaction mixture was concentrated in vacuo to yield the title compound which was used in its entirety (assumed to be 0.32 mmol) without purification in the formation of Example 6.

Data in Table 1.

Intermediate 21, (2S)-2-amino-3-(1-ethylpiperidin-4-yl)-1-[4-(pyridin-4-yl)piperazin-1-yl]propan-1-one

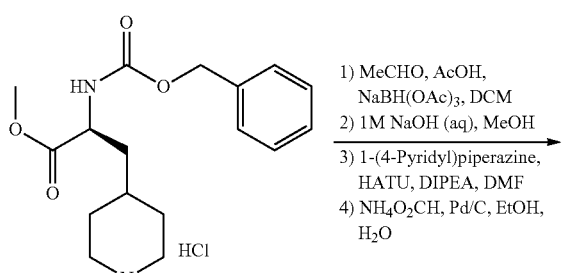

Intermediate 18

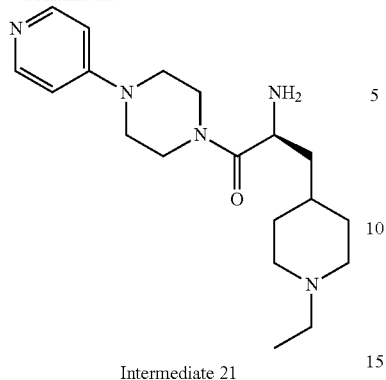

Intermediate 21

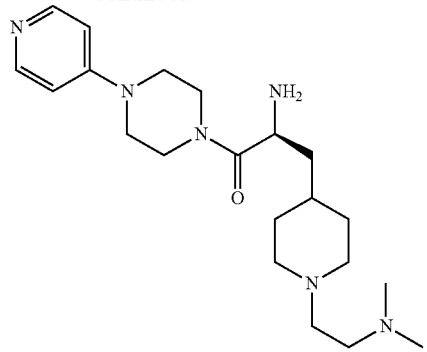

Intermediate 22

The title compound (286 mg, 0.83 mmol) was prepared over four steps from methyl N-[(benzyloxy)carbonyl]-3-piperidin-4-yl-L-alaninate hydrochloride (Intermediate 18, Step 1 product) (320 mg, 0.90 mmol) and acetaldehyde (62 µL, 1.10 mmol) using the methods of Intermediates 18 and 19.

Data in Table 1.

Intermediate 22, (2S)-2-amino-3-{1-[2-(dimethyl-amino)ethyl]piperidin-4-yl}-1-[4-(pyridin-4-yl)piperazin-1-yl]propan-1-one

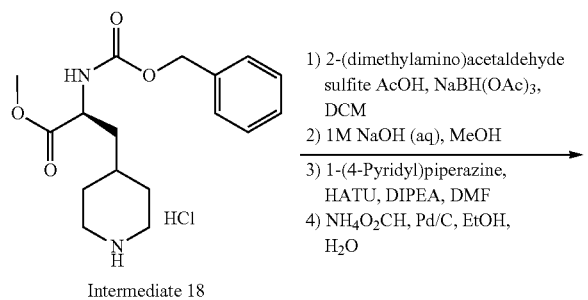

Intermediate 18

1) 2-(dimethylamino)acetaldehyde sulfite AcOH, NaBH(OAc)$_3$, DCM
2) 1M NaOH (aq), MeOH
3) 1-(4-Pyridyl)piperazine, HATU, DIPEA, DMF
4) NH$_4$O$_2$CH, Pd/C, EtOH, H$_2$O The title compound (306 mg, used crude without purification in the formation of Example 12) was prepared over four steps from methyl N-[(benzyloxy)carbonyl]-3-piperidin-4-yl-L-alaninate hydrochloride (Intermediate 18, Step 1 product) (1.0 g, 2.81 mmol) and 2-(dimethylamino)acetaldehyde sulfite (568 mg, 3.36 mmol) using the methods of Intermediates 18 and 19.

Data in Table 1.

Intermediate 23, ethyl 3-(4-{(2S)-2-amino-3-oxo-3-[4-(pyridin-4-yl)piperazin-1-yl]propyl}piperidin-1-yl)-3-oxopropanoate

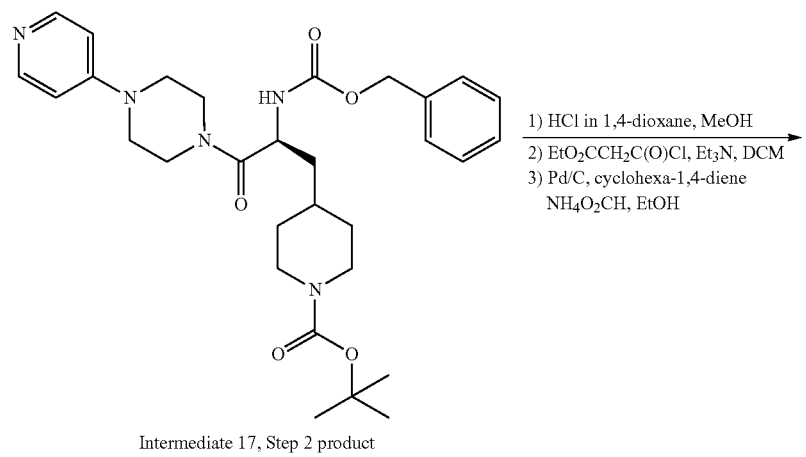

Intermediate 17, Step 2 product

1) HCl in 1,4-dioxane, MeOH
2) EtO$_2$CCH$_2$C(O)Cl, Et$_3$N, DCM
3) Pd/C, cyclohexa-1,4-diene NH$_4$O$_2$CH, EtOH -continued

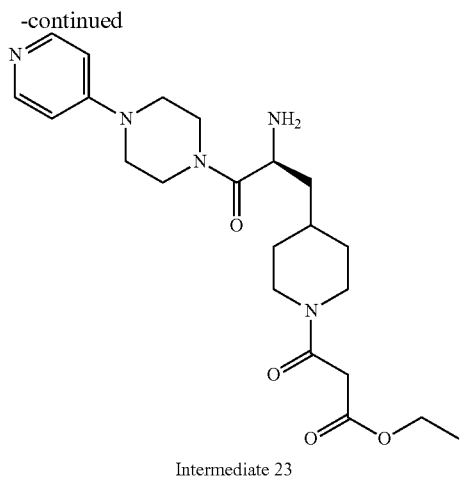

Intermediate 23

Step 1) HCl in 1,4-dioxane (4M, 10.0 mL, 40.0 mmol) was added to a solution of tert-butyl 4-{(2S)-2-{[(benzyloxy)carbonyl]amino}-3-oxo-3-[4-(pyridin-4-yl)piperazin-1-yl]propyl}piperidine-1-carboxylate (Intermediate 17, Step 2 product) (600 mg, 1.09 mmol) in MeOH (10 mL) and the mixture was stirred at rt overnight. Concentration in vacuo yielded benzyl {(2S)-1-oxo-3-(piperidin-4-yl)-1-[4-(pyridin-4-yl)piperazin-1-yl]propan-2-yl}carbamate dihydrochloride (570 mg, 1.09 mmol) as a sticky white solid.

LCMS (Method B): m/z 452.2 (ES+) at 1.72 min.

Step 2) Ethyl 3-chloro-3-oxopropanoate (151 µL, 1.20 mmol) was added to a solution of Et$_3$N (608 µL, 4.36 mmol) and benzyl {(2S)-1-oxo-3-(piperidin-4-yl)-1-[4-(pyridin-4-yl)piperazin-1-yl]propan-2-yl}carbamate dihydrochloride (570 mg, 1.09 mmol) in DCM (20 mL) and the mixture stirred at rt overnight. After concentration in vacuo purification by gradient flash column chromatography, eluting with 0-10% MeOH in DCM yielded the desired material (ethyl 3-(4-{(2S)-2-{[(benzyloxy)carbonyl]amino}-3-oxo-3-[4-(pyridin-4-yl)piperazin-1-yl]propyl}piperidin-1-yl)-3-oxopropanoate, pale yellow sticky solid, 510 mg), as an approximate 2:1 mixture with bis-acylated byproduct (ethyl 3-(4-{(2S)-2-{[(benzyloxy)carbonyl](3-ethoxy-3-oxopropanoyl)amino}-3-oxo-3-[4-(pyridin-4-yl)piperazin-1-yl]propyl}piperidin-1-yl)-3-oxopropanoate). The mixture was used in the following step without further purification.

LCMS (Method B): m/z 566.2 (ES+) at 1.18 min (desired material); m/z 680.2 (ES+) at 0.79 min (bis-acylated byproduct).

Step 3) A mixture of crude ethyl 3-(4-{(2S)-2-{[(benzyloxy)carbonyl]amino}-3-oxo-3-[4-(pyridin-4-yl)piperazin-1-yl]propyl}piperidin-1-yl)-3-oxopropanoate (510 mg) and cyclohexa-1,4-diene (0.85 mL, 9.00 mmol) in EtOH (20 mL) was flushed with N$_2$ before the addition of 10% Pd/C (10 mg). After heating at 70° C. for 1 h, the reaction mixture was cooled to rt and ammonium formate (568 mg, 9.00 mmol) was added. The mixture was heated at 70° C. under N$_2$ overnight before cooling to rt and filtering. The filtrate was concentrated in vacuo to yield the crude title compound (194 mg) which was used without purification in the formation of Example 13.

Data in Table 1.

TABLE 1

| | Intermediates | |
|---|---|---|
| Intermediate | Name | Data |
| 1 | 1-(piperidin-4-yl)-1,3-dihydro-2H-imidazo[4,5-b]pyridin-2-one | Commercially available, CAS No. 185961-99-3 |
| 2 | 3-(piperidin-4-yl)quinolin-2(1H)-one | Commercially available, CAS No. 205058-78-2 |
| 3 | 3-(piperidin-4-yl)-3,4-dihydroquinazolin-2(1H)-one | Commercially available, CAS No. 79098-75-2 |
| 4 | spiro[piperidine-4,4'-[4H]pyrido[2,3-d][1,3]oxazin]-2'(1'H)-one | Commercially available, CAS No. 753440-87-8 |
| 5 | (R)-methyl 2-amino-3-(7-methyl-1H-indazol-5-yl)propanoate | Commercially available, CAS No. 890044-58-3 (free base), CAS No. 1414976-14-9 (dihydrochloride salt) |
| 6 | 3,5-dibromo-D-tyrosine methyl ester | Commercially available, CAS No. 173383-29-4 |
| 7 | (2R)-3-(7-methyl-1H-indazol-5-yl)-2-{[(2'-oxo-1',2'-dihydro-1H-spiro[piperidine-4,4'-pyrido[2,3-d][1,3]oxazin]-1-yl)carbonyl]amino}propanoic acid | LCMS (Method A): m/z 463.5 (ES−), 465.3 (ES+), at 0.10 min. $^1$H NMR (400 MHz, DMSO-d6) δ: 1.53-1.91 (m, 4H), 2.44 (s, 3H), 2.89-3.14 (m, 5H), 3.89 (t, J = 11.5, 2H), 4.23 (br s, 1H), 6.73 (d, J = 7.8, 1H), 6.93-7.06 (m, 2H), 7.31 (d, J = 7.4, 1H), 7.38 (s, 1H), 7.93 (s, 1H), 8.17 (dd, J = 5.1, 1.2, 1H), 10.78 (s, 1H), 13.00 (br s, 1H) |

TABLE 1-continued

Intermediates

| Intermediate | Name | Data |
|---|---|---|
| 8 | (2R)-3-(7-methyl-1H-indazol-5-yl)-2-({[4-(2-oxo-2,3-dihydro-1H-imidazo[4,5-b]pyridin-1-yl)piperidin-1-yl]carbonyl}amino)propanoic acid | LCMS (Method A): m/z 464.1 (ES+), at 1.14 min. $^1$H NMR (400 MHz, DMSO-$d_6$) δ: 1.62-1.67 (m, 2H), 1.87-2.12 (m, 2H), 2.38-2.52 (m, 1H), 2.46 (s, 3H), 2.70-2.80 (m, 2H), 2.98 (dd, J = 13.7, 9.8, 1H), 3.09 (dd, J = 13.7, 4.3, 1H), 4.08 (br d, J = 12.9, 2H), 4.20-4.27 (m, 1H), 4.28-4.38 (m, 1H), 6.75 (d, J = 8.2, 1H), 6.88 (dd, J = 7.8, 5.5, 1H), 7.42 (s, 1H), 7.27 (d, J = 7.8, 1H), 7.42 (s, 1H), 7.88 (dd, J = 5.1, 1.2, 1H), 7.96 (s, 1H), 11.54 (br s, 1H), 12.99 (br s, 1H) |
| 9 | (2R)-3-(7-methyl-1H-indazol-5-yl)-2-({[4-(2-oxo-1,2-dihydroquinolin-3-yl)piperidin-1-yl]carbonyl}amino)propanoic acid | LCMS (Method A): m/z 474.3 (ES+), at 1.82 min. $^1$H NMR (400 MHz, DMSO-$d_6$) δ: 1.25-1.36 (m, 2H), 1.72-1.78 (m, 2H), 2.48 (s, 3H), 2.66-2.78 (m, 2H), 2.88-2.94 (m, 1H), 2.97-3.03 (m, 1H), 3.10 (dd, J = 8.4, 3.4, 1H), 4.08 (d, J = 12.0, 2H), 4.24-4.30 (m, 1H), 6.57 (d, J = 8.0, 1H), 7.04 (s, 1H), 7.15 (dd, J = 12.4, 1.2, 1H), 7.27 (d, J = 8.4, 1H), 7.41-7.45 (m, 2H), 7.54 (s, 1H), 7.62 (dd, J = 6.8, 1.2, 1H), 7.97 (s, 1H), 11.69 (s, 1H), 12.1-13.1 (br s, 2H). |
| 10 | 3,5-dibromo-N-{[4-(2-oxo-1,2-dihydroquinolin-3-yl)piperidin-1-yl]carbonyl}-D-tyrosine | LCMS (Method A): m/z 592.0, 594.0, 596.0 (ES+), at 0.14 min. $^1$H NMR (400 MHz, DMSO-$d_6$) δ: 1.14-1.40 (m, 2H), 1.75-1.77 (m, 2H), 2.68-2.99 (m, 5H), 3.97-4.19 (m, 3H), 6.71 (d, J = 8.2 Hz, 1H), 7.14 (t, J = 7.6 Hz, 1H), 7.26 (t, J = 7.4, 1H), 7.36-7.49 (m, 3H), 7.53-7.70 (m, 2H), 9.74 (s, 1H), 11.77 (s, 1H), 12.54 (br s, 1H) |
| 11 | 3,5-dibromo-N-{[4-(2-oxo-2,3-dihydro-1H-imidazo[4,5-b]pyridin-1-yl)piperidin-1-yl]carbonyl}-D-tyrosine | LCMS (Method A): m/z 580.3, 582.1, 584.0 (ES−), 582.1, 584.1, 586.1 (ES+), at 0.39 min. $^1$H NMR (400 MHz, DMSO-$d_6$) δ: 1.53-1.76 (d, J = 11.3, 2H), 1.91-2.21 (m, 2H), 2.72-2.89 (m, 3H), 2.97 (dd, J = 13.7, 4.3, 1H), 4.10 (d, J = 12.5, 2H), 4.15-4.26 (m, 1H), 4.38 (t, J = 12.3, 1H), 6.82 (d, J = 8.2, 1H), 6.96 (dd, J = 7.8, 5.1, 1H), 7.34 (d, J = 7.8, 1H), 7.47 (s, 2H), 7.89 (d, J = 4.3, 1H), 9.72 (br s, 1H), 11.57 (br s, 1H) (1 exchangeable proton not observed) |
| 12 | 3,5-dibromo-N-{[4-(2-oxo-1,4-dihydroquinazolin-3(2H)-yl)piperidin-1-yl]carbonyl}-D-tyrosine | LCMS (Method A): m/z 593.2, 595.3, 597.1 (ES−), 595.1, 597.1, 599.1 (ES+), at 0.41 min. $^1$H NMR (400 MHz, DMSO-$d_6$) δ: 1.41-1.68 (m, 4H), 2.65 (t, J = 11.7, 1H), 2.70-2.96 (m, 3H), 3.80-3.95 (m, 1H), 4.01 (d, J = 12.9, 1H), 4.23 (s, 2H), 4.24-4.38 (m, 1H), 6.24 (d, J = 4.7, 1H), 6.74 (d, J = 7.8, 1H), 6.84 (t, J = 7.4, 1H), 7.02-7.16 (m, 2H), 7.24 (s, 2H), 9.21 (s, 1H) (2 exchangeable protons not observed) |
| 13 | (2R)-3-(7-methyl-1H-indazol-5-yl)-2-({[4-(2-oxo-1,4-dihydroquinazolin-3(2H)-yl)piperidin-1-yl]carbonyl}amino)propanoic acid | LCMS (Method A): m/z 475.4 (ES−), 477.3 (ES+), at 0.66 min. $^1$H NMR (400 MHz, DMSO-d6) δ: 1.36-1.66 (m, 4H), 2.47 (s, 3H), 2.59-2.78 (m, 2H), 2.92-3.14 (m, 3H), 4.00 (t, J = 16.0, 2H), 4.06-4.20 (m, 2H), 4.20-4.33 (m, 1H), 6.47 (br s, 1H), 6.75 (d, J = 7.8, 1H), 6.86 (t, J = 7.4, 1H), 7.01 (s, 1H), 7.06-7.17 (m, 2H), 7.36 (s, 1H), 7.96 (s, 1H), 9.21 (s, 1H), 12.99 (s, 1H) (1 exchangeable proton not observed) |
| 14 | 3,5-dibromo-N-[(2'-oxo-1',2'-dihydro-1H-spiro[piperidine-4,4'-pyrido[2,3-d][1,3]oxazin]-1-yl)carbonyl]-D-tyrosine | LCMS (Method A): m/z 583.3, 585.0, 587.0 (ES+), at 0.13 min. $^1$H NMR (400 MHz, DMSO-$d_6$) δ: 1.63-2.01 (m, 4H), 2.82 (t, J = 10.9, 1H), 2.90-3.14 (m, 3H), 3.95 (t, J = 12.3, 2H), 4.15-4.28 (m, 1H), 6.86 (d, J = 8.2, 1H), 7.08 (dd, J = 7.2, 5.3, 1H), 7.45 (s, 2H), 7.55 (d, J = 7.4, 1H), 8.20 (d, J = 4.7, 1H), 9.75 (br s, 1H), 10.83 (s, 1H) (1 exchangeable proton not observed) |
| 15 | 1-(4-pyridinyl)piperazine | Commercially available, CAS No. 1008-91-9 |
| 16 | tert-butyl 4-[(2S)-2-{[(benzyloxy)carbonyl]amino}-3-methoxy-3-oxopropyl]piperidine-1-carboxylate | Commercially available, CAS No. 195877-54-4 |
| 17 | tert-butyl 4-{(2S)-2-amino-3-oxo-3-[4-(pyridin-4-yl)piperazin-1-yl]propyl}piperidine-1-carboxylate | LCMS (Method A): m/z 318.3, 362.2, 418.3 (ES+), at 2.70 min. $^1$H NMR (400 MHz, DMSO-$d_6$) δ: 0.89-1.09 (m, 2H), 1.38 (s, 9H), 1.43-1.69 (m, 5H), 1.80 (d, J = 10.9, 1H), 2.67 (br s, 2H), 3.42-3.79 (m, 7H), 3.84-4.00 (m, 2H), 4.11-4.25 (m, 1H), 4.34 (br s, 2H), 6.84 (d, J = 6.6, 2H), 8.19 (d, J = 6.2, 2H) |

TABLE 1-continued

Intermediates

| Intermediate | Name | Data |
|---|---|---|
| 18 | methyl N-[(benzyloxy)carbonyl]-3-(1-propylpiperidin-4-yl)-L-alaninate | LCMS (Method B): m/z 363.0 (ES+), at 1.57 min. $^1$H NMR (400 MHz, CDCl$_3$) δ: ppm 0.95 (t, J = 7.4, 3H), 1.47-1.62 (m, 2H), 1.70-1.80 (m, 6H), 2.01-2.07 (m, 1H), 2.36-2.46 (m, 2H), 2.69-2.76 (m, 2H), 3.36-3.43 (m, 2H), 3.73 (s, 3H), 4.33-4.43 (m, 1H), 5.09-5.12 (m, 2H), 5.31-5.33 (m, 1H), 7.30-7.38 (m, 5H) |
| 19 | (2S)-2-amino-3-(1-propylpiperidin-4-yl)-1-[4-(pyridin-4-yl)piperazin-1-yl]propan-1-one | LCMS (Method B): m/z 360.2 (ES+), at 0.97 min. |
| 20 | 1-(4-{(2S)-2-amino-3-oxo-3-[4-(pyridin-4-yl)piperazin-1-yl]propyl}piperidin-1-yl)pentan-1-one | LCMS (Method B): m/z 402.2 (ES+), at 1.04 min. |
| 21 | (2S)-2-amino-3-(1-ethylpiperidin-4-yl)-1-[4-(pyridin-4-yl)piperazin-1-yl]propan-1-one | LCMS (Method B): m/z 346.2 (ES+), at 1.03 min. |
| 22 | (2S)-2-amino-3-{1-[2-(dimethylamino)ethyl]piperidin-4-yl}-1-[4-(pyridin-4-yl)piperazin-1-yl]propan-1-one | LCMS (Method B): m/z 389.2 (ES+), at 0.81 min. |
| 23 | ethyl 3-(4-{(2S)-2-amino-3-oxo-3-[4-(pyridin-4-yl)piperazin-1-yl]propyl}piperidin-1-yl)-3-oxopropanoate | LCMS (Method B): m/z 432.2 (ES+), at 0.85 min. |

SYNTHESIS OF EXAMPLES

Typical procedures for the preparation of examples via amide coupling, and where appropriate, deprotection, as exemplified by the preparation of the below examples.

Procedure 1:

Example 11, N-[(2R)-3-(7-methyl-1H-indazol-5-yl)-1-oxo-1-({(2S)-1-oxo-3-(piperidin-4-yl)-1-[4-(pyridin-4-yl)piperazin-1-yl]propan-2-yl}amino)propan-2-yl]-2'-oxo-1',2'-dihydro-1H-spiro[piperidine-4,4'-pyrido[2,3-d][1,3]oxazine]-1-carboxamide

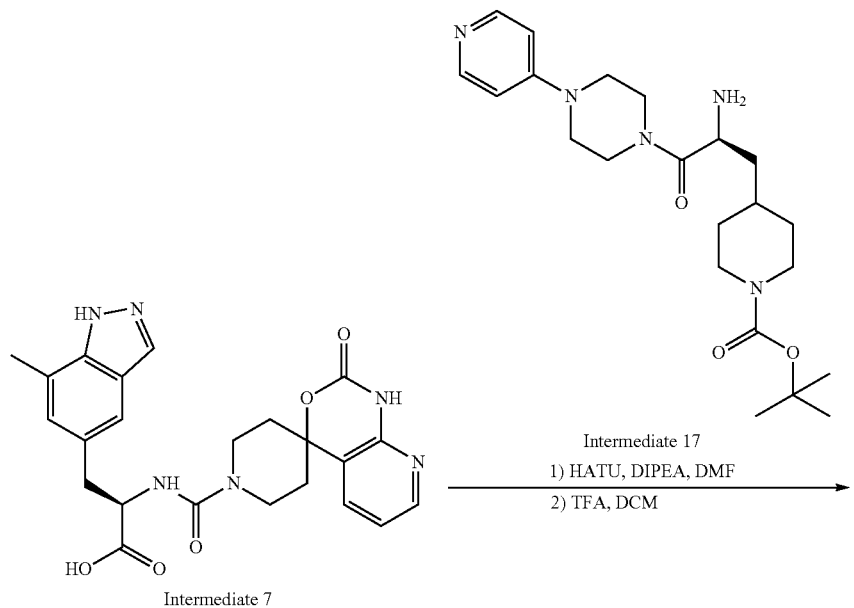

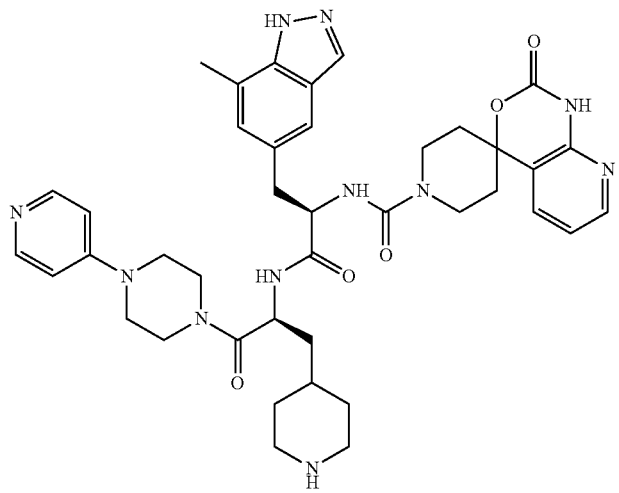

Example 11

Step 1: HATU (4.57 g, 12.0 mmol) was added to a solution of (2R)-3-(7-methyl-1H-indazol-5-yl)-2-{[(2'-oxo-1',2'-dihydro-1H-spiro[piperidine-4,4'-pyrido[2,3-d][1,3]oxazin]-1-yl)carbonyl]amino}propanoic acid (Intermediate 7, 4.65 g, 10.0 mmol) in DMF (150 mL), followed after 15 min by the addition of tert-butyl 4-{(2S)-2-amino-3-oxo-3-[4-(pyridin-4-yl)piperazin-1-yl]propyl}piperidine-1-carboxylate (Intermediate 17, 4.60 g, 11.0 mmol) and DIPEA (6.86 mL, 40.1 mmol). The mixture was stirred at rt for 17 h before the addition of H$_2$O (600 mL). The resulting precipitate was isolated by filtration, washed with H$_2$O, and dissolved in a small amount of MeOH. Co-evaporation twice with toluene yielded crude tert-butyl 4-{(2S)-2-{[(2R)-3-(7-methyl-1H-indazol-5-yl)-2-{[(2'-oxo-1',2'-dihydro-1H-spiro[piperidine-4,4'-pyrido[2,3-d][1,3]oxazin]-1-yl)carbonyl]amino}propanoyl]amino}-3-oxo-3-[4-(pyridin-4-yl)piperazin-1-yl]propyl}piperidine-1-carboxylate (7.82 g) which was used in the next step without further purification. A second batch of material (3.53 g) was prepared using this method.

LCMS (Method D): m/z 864.7 (ES$^+$) at 0.88 min.

Step 2: TFA (31 mL) was added to a solution of tert-butyl 4-{(2S)-2-{[(2R)-3-(7-methyl-1H-indazol-5-yl)-2-{[(2'-oxo-1',2'-dihydro-1H-spiro[piperidine-4,4'-pyrido[2,3-d][1,3]oxazin]-1-yl)carbonyl]amino}propanoyl]amino}-3-oxo-3-[4-(pyridin-4-yl)piperazin-1-yl]propyl}piperidine-1-carboxylate (Step 1, Batch 1, 7.82 g) in DCM (150 mL) and the solution stirred at rt for 1 h. Toluene (50 mL) was added and the mixture was concentrated in vacuo. DCM (200 mL) and H$_2$O (50 mL) were added and the pH adjusted to approximately 12 with 2M (aq) NaOH solution. The phases were separated and the aqueous layer extracted with DCM/isopropanol (1:1, 5×200 mL). The combined organic phases were concentrated in vacuo. Purification by gradient flash column chromatography, eluting with 0-100% (DCM/MeOH/7N NH$_3$ in MeOH (4:1:0.4)) in DCM yielded the title compound. A second batch of title compound was prepared using this method from Step 1, Batch 2 material. The purified title compound from both batches was combined, dissolved in a mixture of DCM, MeOH and diisopropyl ether, sonicated and concentrated in vacuo to yield the title compound (5.30 g, 6.94 mmol).

Data in Table 2.

Example 14, 3,5-dibromo-Nα-[(2'-oxo-1',2'-di-hydro-1H-spiro[piperidine-4,4'-pyrido[2,3-d][1,3]oxazin]-1-yl)carbonyl]-N-{(2S)-1-oxo-3-(piperidin-4-yl)-1-[4-(pyridin-4-yl)piperazin-1-yl]propan-2-yl}-D-tyrosinamide

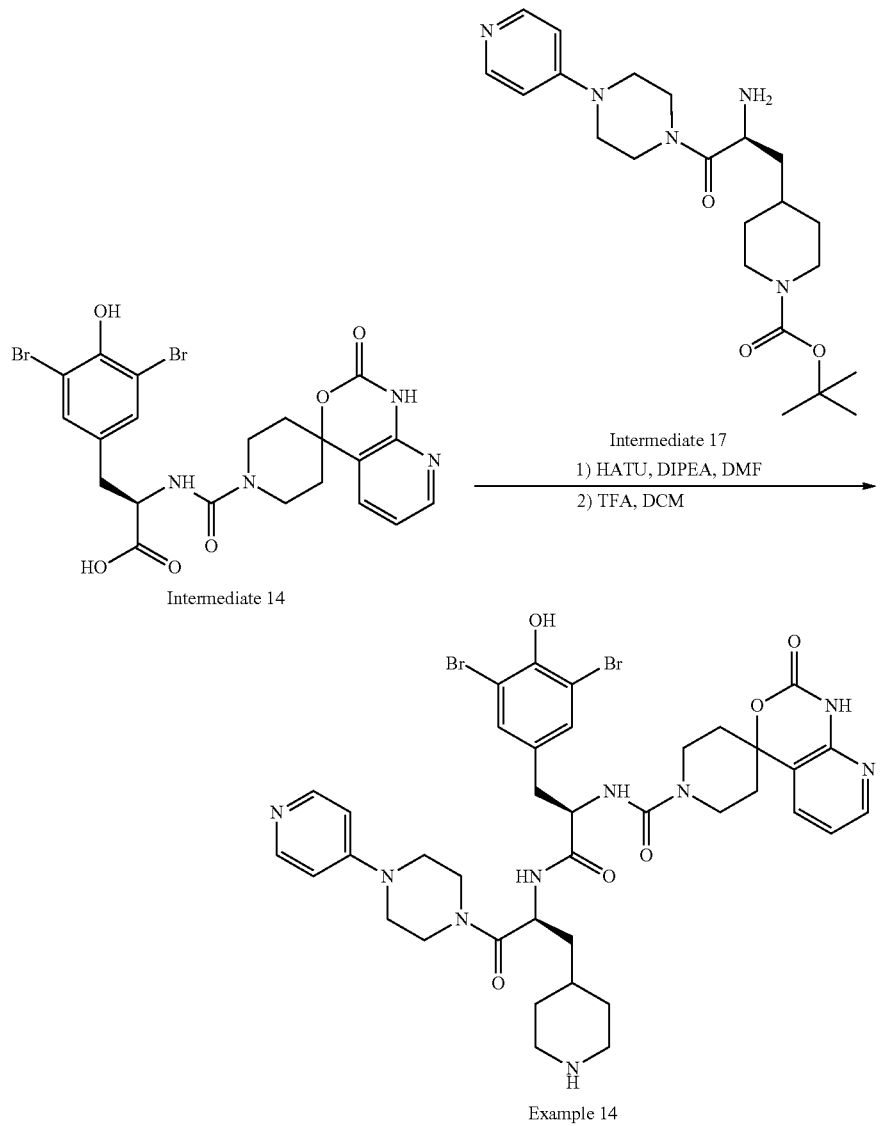

Step 1) A solution of HATU (7.84 g, 20.6 mmol) and 3,5-dibromo-N-[(2'-oxo-1',2'-dihydro-1H-spiro[piperidine-4,4'-pyrido[2,3-d][1,3]oxazin]-1-yl)carbonyl]-D-tyrosine (Intermediate 14, 10.0 g, 17.2 mmol) in DMF (75 mL) was stirred at rt for 30 min before the addition of tert-butyl 4-{(2S)-2-amino-3-oxo-3-[4-(pyridin-4-yl)piperazin-1-yl]propyl}piperidine-1-carboxylate (Intermediate 17, 7.72 g, 18.5 mmol) and DIPEA (11.8 mL, 68.8 mmol). The reaction mixture was stirred at rt overnight before cold H$_2$O (500 mL), saturated aqueous NaHCO$_3$ and DCM (200 mL) were added. The phases were separated and the aqueous phase was extracted with DCM (3×200 mL). The combined organic phases were washed with brine (200 mL), concentrated in vacuo, and co-evaporated with toluene. Purification by gradient flash column chromatography, eluting with 0-100% solvent B in DCM (where solvent B=DCM/MeOH/7N NH$_3$ in MeOH (90:9:1.5) yielded 3,5-dibromo-Nα-{(2S)-3-[1-(tert-butoxycarbonyl)piperidin-4-yl]-1-oxo-1-[4-(pyridin-4-yl)piperazin-1-yl]propan-2-yl}-N-[(2'-oxo-1',2'-dihydro-1H-spiro[piperidine-4,4'-pyrido[2,3-d][1,3]oxazin]-1-yl)carbonyl]-D-tyrosinamide (9.7 g, 9.86 mmol) as a white solid.

LCMS (Method D): m/z 984.5 (ES$^+$) at 0.78 min.

Step 2: 3,5-Dibromo-Nα-{(2S)-3-[1-(tert-butoxycarbonyl)piperidin-4-yl]-1-oxo-1-[4-(pyridin-4-yl)piperazin-1-yl]propan-2-yl}-Nα-[(2'-oxo-1',2'-dihydro-1H-spiro[piperidine-4,4'-pyrido[2,3-d][1,3]oxazin]-1-yl)carbonyl]-D-tyrosinamide (9.7 g, 9.86 mmol) was dissolved in DCM (70 mL), cooled to 0° C., and TFA (15 mL) was added dropwise. The mixture was stirred at rt for 10 min before the addition of toluene (50 mL) and concentration in vacuo. DCM (200 mL) and H$_2$O (100 mL) were added, the pH was adjusted to approximately 10 with 2N aqueous NaOH solution. The resulting precipitate was isolated by filtration, dissolved in DCM/MeOH (1:1, 300 mL), concentrated in vacuo, and co-evaporated several times with MeOH and toluene. Trituration from MeOH/methyl tert-butyl ether yielded the title compound (5.30 g, 6.00 mmol).
Data in Table 2.
Procedure 2:

Example 1, N-[(2R)-3-(7-methyl-1H-indazol-5-yl)-1-oxo-1-({(2S)-1-oxo-3-(piperidin-4-yl)-1-[4-(pyridin-4-yl)piperazin-1-yl]propan-2-yl}amino)propan-2-yl]-4-(2-oxo-2,3-dihydro-1H-imidazo[4,5-b]pyridin-1-yl)piperidine-1-carboxamide 5-b]pyridin-1-yl)piperidin-1-yl]carbonyl}amino)propanoic acid (Intermediate 8, 100 mg, 0.22 mmol) and tert-butyl 4-{(2S)-2-amino-3-oxo-3-[4-(pyridin-4-yl)piperazin-1-yl]propyl}piperidine-1-carboxylate (Intermediate 17, 92 mg, 0.22 mmol) in DMF (2 mL) and the reaction mixture was stirred at rt for 10 d before concentration in vacuo to yield crude tert-butyl 4-{(2S)-2-{[(2R)-3-(7-methyl-1H-indazol-5-yl)-2-({[4-(2-oxo-2,3-dihydro-1H-imidazo[4,5-b]pyridin-1-yl)piperidin-1-yl]carbonyl}amino)propanoyl]amino}-3-oxo-3-[4-(pyridin-4-yl)piperazin-1-yl]propyl}piperidine-1-carboxylate (190 mg, viscous brown oil) which was used without purification in the subsequent step.

LCMS (Method C): m/z 863.5 (ES$^+$) at 1.89 min.

Step 2: Crude tert-butyl 4-{(2S)-2-{[(2R)-3-(7-methyl-1H-indazol-5-yl)-2-({[4-(2-oxo-2,3-dihydro-1H-imidazo[4,5-b]pyridin-1-yl)piperidin-1-yl]carbonyl}amino)propanoyl]amino}-3-oxo-3-[4-(pyridin-4-yl)piperazin-1-yl]

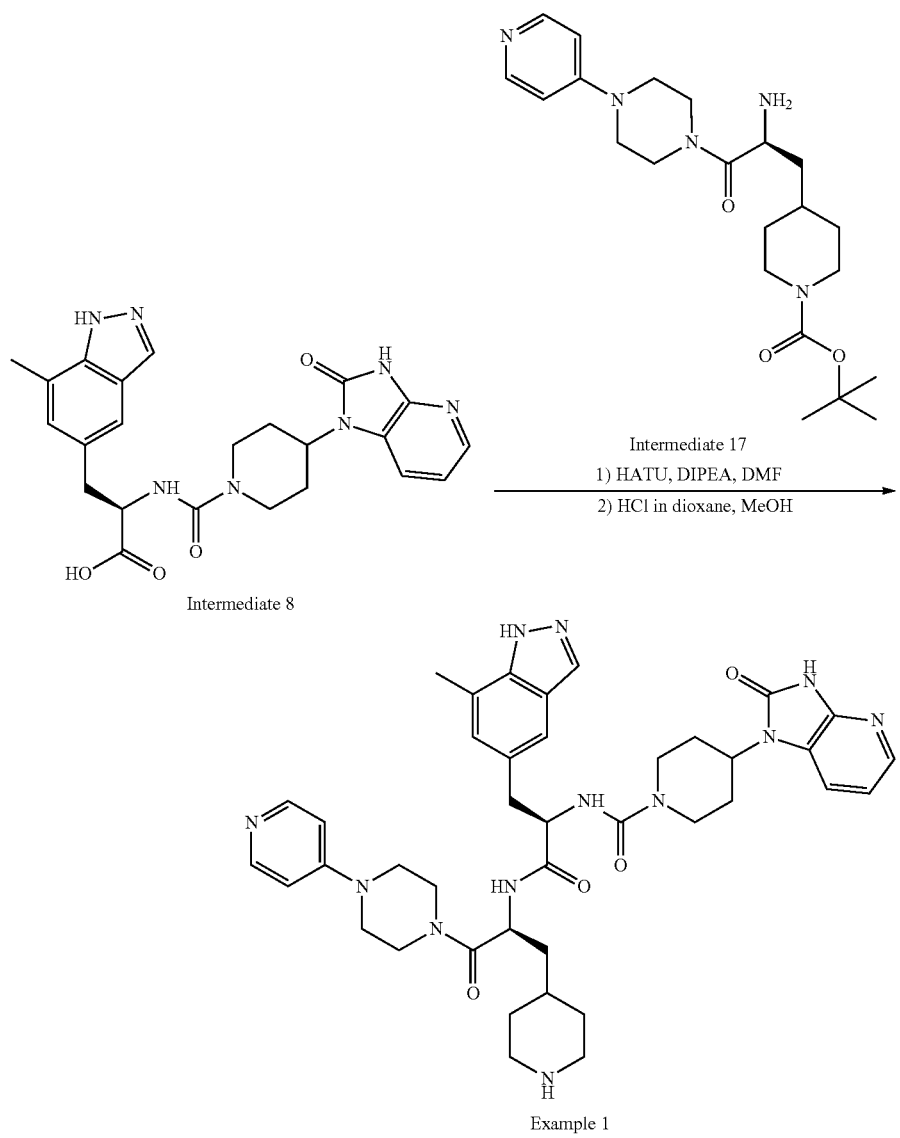

Intermediate 8

Intermediate 17
1) HATU, DIPEA, DMF
2) HCl in dioxane, MeOH

Example 1

Step 1: DIPEA (0.12 mL, 0.66 mmol) was added to a solution of HATU (99 mg, 0.22 mmol), (2R)-3-(7-methyl-1H-indazol-5-yl)-2-({[4-(2-oxo-2,3-dihydro-1H-imidazo[4, propyl}piperidine-1-carboxylate (190 mg) was dissolved in MeOH (5 mL) and HCl in dioxane (4M, 5.0 mL, 20.0 mmol) was added. The reaction mixture was stirred at rt for 2 h before concentration in vacuo. Purification by preparative reversed phase HPLC (Phenomenex Gemini-NX 5 μm C18 column, 100×30 mm, eluting with 15 to 90% MeCN/Solvent B over 26 min at 30 mL/min [where solvent B is 0.2% of (28% NH₃/H₂O) in H₂O] and collecting fractions by monitoring at 205 nm) yielded Example 1 (25 mg, 0.03 mmol) as a beige solid.
Data in Table 2.
Procedure 3:

Example 13, 3-(4-{(2S)-2-{[(2R)-3-(7-methyl-1H-indazol-5-yl)-2-({[4-(2-oxo-2,3-dihydro-1H-imidazo[4,5-b]pyridin-1-yl]piperidin-1-yl]carbonyl}amino) propanoyl]amino}-3-oxo-3-[4-(pyridin-4-yl) piperazin-1-yl]propyl}piperidin-1-yl)-3-oxopropanoic acid, ammonium salt Step 1: A mixture of DIPEA (0.27 mL, 1.52 mmol), HATU (172 mg, 0.45 mmol), (2R)-3-(7-methyl-1H-indazol-5-yl)-2-({[4-(2-oxo-2,3-dihydro-1H-imidazo[4,5-b]pyridin-1-yl)piperidin-1-yl]carbonyl}amino)propanoic acid (Intermediate 8, 176 mg, 0.38 mmol) and ethyl 3-(4-{(2S)-2-amino-3-oxo-3-[4-(pyridin-4-yl)piperazin-1-yl] propyl}piperidin-1-yl)-3-oxopropanoate (Intermediate 23, 194 mg, 0.45 mmol) in DMF (10 mL) was stirred at rt overnight before concentration in vacuo. The crude material was filtered through a short plug of SiO₂, eluting with MeOH, before further purification by preparative HPLC (Phenomenex Gemini-NX 5 μm C18 column, 100×30 mm, eluting with 15 to 35% MeCN/Solvent B over 12.5 min at 30 mL/min [where solvent B is 0.2% of (28% NH₃/H₂O) in H₂O], collecting fractions by monitoring at 205 nm). During the purification, cleavage of the ethyl ester was observed. Carboxylic acid containing fractions were combined and

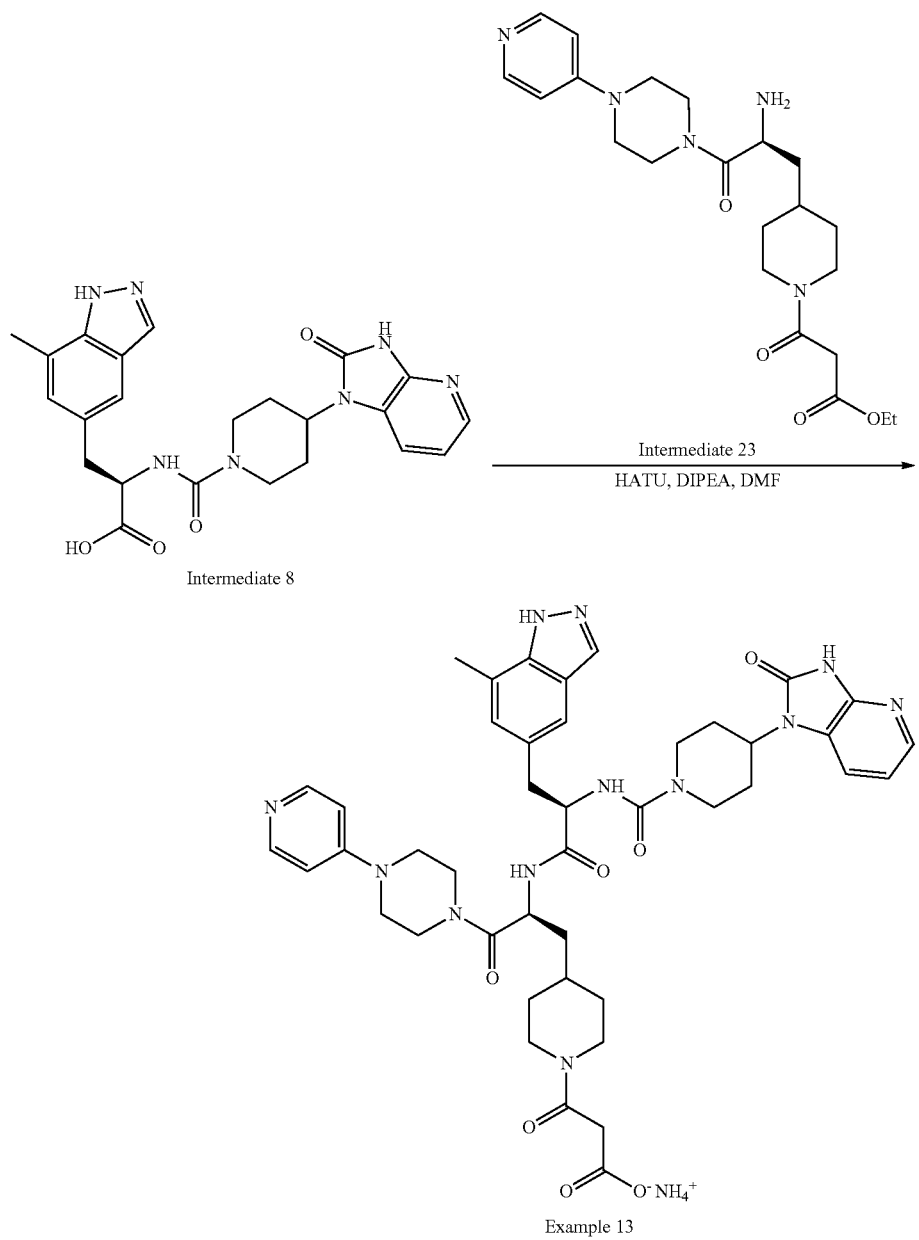

added to 10 mL of concentrated aqueous ammonia, and the mixture was allowed to stand at rt overnight before concentration in vacuo to yield the title compound (10 mg, 0.01 mmol) as a colourless solid.
Data in Table 2.
Further examples prepared by the above procedures are detailed in Table 2.

TABLE 2

| Ex. No. | Name | Intermediates/ Procedure | $^1$H NMR | LCMS data (Method A) |
|---|---|---|---|---|
| 1 | N-[(2R)-3-(7-methyl-1H-indazol-5-yl)-1-oxo-1-({(2S)-1-oxo-3-(piperidin-4-yl)-1-[4-(pyridin-4-yl)piperazin-1-yl]propan-2-yl}amino)propan-2-yl]-4-(2-oxo-2,3-dihydro-1H-imidazo[4,5-b]pyridin-1-yl)piperidine-1-carboxamide | 8, 17 Procedure 2 | (400 MHz, CD$_3$OD) δ: ppm 1.02-1.32 (m, 3H), 1.34-1.61 (m, 3H), 1.66-1.84 (m, 3H), 1.86-1.93 (m, 1H), 1.96-2.10 (m, 1H), 2.17-2.26 (m, 1H), 2.43-2.53 (m, 2H), 2.70-2.73 (m, 1H), 2.80-2.93 (m, 2H), 2.99-3.08 (m, 2H), 3.10-3.24 (m, 2H), 3.25-4.42 (m, 1H), 3.44-3.56 (m, 4H), 3.60-3.80 (m, 3H), 3.84-3.93 (m, 2H), 4.11-4.15 (m, 2H), 4.44-4.36 (m, 1H, 4.54-4.57 (m, 1H), 6.80-6.87 (m, 2H), 6.96 (dd, J = 8.0, 5.3, 1H), 7.16 (s, 1H), 7.31 (d, J = 7.8, 1H), 7.48 (s, 1H), 7.92 (m, 1H), 7.97 (s, 1H), 8.08-8.15 (m, 2H) (5 exchangeable protons not observed) | m/z 763.2 (ES+), at 1.10 min, 95% |
| 2 | tert-butyl 4-{(2S)-2-{[(2R)-3-(7-methyl-1H-indazol-5-yl)-2-({[4-(2-oxo-1,2-dihydroquinolin-3-yl)piperidin-1-yl]carbonyl}amino)propanoyl]amino}-3-oxo-3-[4-(pyridin-4-yl)piperazin-1-yl]propyl}piperidine-1-carboxylate | 9, 17 Procedure 1, Step 1 | (400 MHz, DMSO-d$_6$) δ: ppm 0.73-1.04 (m, 2H), 1.08-1.40 (m, 2H), 1.40-1.54 (m, 9H), 1.55-1.80 (m, 6H), 2.45 (s, 3H), 2.57-2.75 (m, 4H), 2.77-2.93 (m, 2H), 2.93-3.07 (m, 1H), 3.09-3.30 (m, 4H), 3.36-3.59 (m, 4H), 3.61-3.93 (m, 3H), 4.05 (d, J = 12.5, 2H), 4.27-4.49 (m, 1H), 4.82 (q, J = 7.3, 1H), 6.58 (d, J = 8.6, 1H), 6.77 (d, J = 6.2, 2H), 7.13 (t, J = 8.2, 2H), 7.25 (d, J = 8.2, 1H), 7.35-7.53 (m, 3H), 7.60 (d, J = 7.8, 1H), 7.95 (s, 1H), 8.12 (d, J = 5.9, 2H), 8.33 (d, J = 9.0, 1H), 11.75 (s, 1H), 13.00 (s, 1H) | m/z 871.5 (ES−), 873.5 (ES+), at 2.54 min, 96% |
| 3 | N-[(2R)-3-(7-methyl-1H-indazol-5-yl)-1-oxo-1-({(2S)-1-oxo-3-(piperidin-4-yl)-1-[4-(pyridin-4-yl)piperazin-1-yl]propan-2-yl}amino)propan-2-yl]-4-(2-oxo-1,2-dihydroquinolin-3-yl)piperidine-1-carboxamide | 9, 17 Procedure 1 | (400 MHz, DMSO-d$_6$) δ: ppm 1.00-1.32 (m, 4H), 1.32-1.43 (m, 1H), 1.43-1.57 (m, 2H), 1.57-1.78 (m, 3H), 1.84 (d, J = 13.7, 1H), 2.52 (s, 3H), 2.60-2.78 (m, 4H), 2.78-3.07 (m, 3H), 3.07-3.27 (m, 3H), 3.75-3.93 (m, 6H), 3.93-4.14 (m, 2H), 4.17-4.45 (m, 1H), 4.81 (q, J = 7.8, 1H), 6.59 (d, J = 8.2, 1H), 7.00-7.22 (m, 4H), 7.25 (d, J = 7.8, 1H), 7.35-7.55 (m, 3H), 7.59 (d, J = 7.4, 1H), 7.97 (s, 1H), 8.07-8.37 (m, 3H), 8.42 (d, J = 8.6, 2H), 11.75 (s, 1H), 13.40 (br s, 1H) | m/z 771.6 (ES−), 773.5 (ES+), at 2.88 min, 96% |
| 4 | N-[(2R)-3-(7-methyl-1H-indazol-5-yl)-1-oxo-1-({(2S)-1-oxo-3-(1-propylpiperidin-4-yl)-1-[4-(pyridin-4-yl)piperazin-1-yl]propan-2-yl}amino)propan-2-yl]-4-(2-oxo-1,2-dihydroquinolin-3-yl)piperidine-1-carboxamide | 9, 19 Procedure 1, Step 1 | (400 MHz, CD$_3$OD) δ: ppm 0.89 (t, J = 7.4, 3H), 0.98-1.21 (m, 2H), 1.27-1.36 (m, 1H), 1.37-1.52 (m, 5H), 1.57-1.67 (m, 3H), 1.76-1.86 (m, 2H), 2.01 (s, 3H), 2.18-2.22 (m, 2H), 2.46-2.53 (m, 2H), 2.76-2.79 (m, 1H), 2.80-2.90 (m, 2H), 2.98-3.06 (m, 2H), 3.16-3.22 (m, 1H), 3.34 (s, 3H), 3.37-3.40 (m, 1H), 3.43-3.55 (m, 3H), 3.59-3.65 (m, 1H), 3.84-3.91 (m, 2H), 4.07-4.16 (m, 2H), 4.63 (t, J = 7.8, 1H), 6.79-6.81 (m, 2H), 7.14 (s, 1H), 7.21-7.23 (m, 1H), 7.25-7.32 (m, 1H), 7.45-7.48 (m, 2H), 7.55 (s, 1H), 7.62-7.64 (m, 1H), 7.97 (s, 1H), 8.08-8.10 (m, 2H) (4 exchangeable protons not observed) | m/z 815.6 (ES+), at 3.32 min, 95% |

TABLE 2-continued

| Ex. No. | Name | Intermediates/ Procedure | $^1$H NMR | LCMS data (Method A) |
|---|---|---|---|---|
| 5 | 3,5-dibromo-Nα-{[4-(2-oxo-1,2-dihydroquinolin-3-yl)piperidin-1-yl]carbonyl}-N-{(2S)-1-oxo-3-(piperidin-4-yl)-1-[4-(pyridin-4-yl)piperazin-1-yl]propan-2-yl}-D-tyrosinamide | 10, 17 Procedure 1 | (400 MHz, MeOD) δ: ppm 1.25-1.54 (m, 5H), 1.54-1.69 (m, 2H), 1.80-1.93 (m, 3H), 2.04 (d, J = 13.3, 1H), 2.76-3.09 (m, 7H), 3.34-3.43 (m, 3H), 3.52-3.63 (m, 1H), 3.63-3.79 (m, 3H), 3.80-4.04 (m, 4H), 4.04-4.21 (m, 2H), 4.43 (t, J = 7.8, 1H), 7.14 (d, J = 7.4, 2H), 7.25 (t, J = 7.6, 1H), 7.32 (d, J = 8.2, 1H), 7.44 (s, 2H), 7.50 (t, J = 7.4, 1H), 7.64-7.79 (m, 2H), 8.14 (d, J = 7.4, 2H) (5 exchangeable protons not observed) | m/z 891.4, 893.2, 895.3 (ES$^+$), at 2.20 and 2.44 min, 100% |
| 6 | N-[(2R)-3-(7-methyl-1H-indazol-5-yl)-1-oxo-1-({(2S)-1-oxo-3-(1-pentanoylpiperidin-4-yl)-1-[4-(pyridin-4-yl)piperazin-1-yl]propan-2-yl}amino)propan-2-yl]-4-(2-oxo-1,2-dihydroquinolin-3-yl)piperidine-1-carboxamide | 9, 20 Procedure 1, Step 1 | (400 MHz, DMSO-d$_6$) δ: 0.78-1.11 (m, 6H), 1.14-1.61 (m, 13H), 1.63-1.82 (m, 3H), 2.12-2.34 (m, 3H), 2.63-3.10 (m, 7H), 3.35-3.85 (m, 7H), 3.90-4.48 (m, 4H), 4.70-4.91 (m, 1H), 6.52-6.91 (m, 3H), 7.06-7.33 (m, 3H), 7.36-7.69 (m, 4H), 7.95 (s, 1H), 8.09-8.15 (m, 2H), 8.34 (d, J = 8.9, 1H), 11.58-11.94 (m, 1H), 12.81-13.16 (m, 1H) | m/z 857.7 (ES$^+$), at 1.76 min, 100% |
| 7 | N-[(2R)-1-({(2S)-3-(1-ethylpiperidin-4-yl)-1-oxo-1-[4-(pyridin-4-yl)piperazin-1-yl]propan-2-yl}amino)-3-(7-methyl-1H-indazol-5-yl)-1-oxopropan-2-yl]-4-(2-oxo-1,2-dihydroquinolin-3-yl)piperidine-1-carboxamide | 9, 21 Procedure 1, Step 1 | (400 MHz, CD$_3$OD) δ: ppm 1.00-1.22 (m, 5H), 1.23-1.35 (m, 2H), 1.39-1.54 (m, 4H), 1.64-1.91 (m, 5H), 2.38-2.45 (m, 2H), 2.55 (s, 3H), 2.79-3.08 (m, 7H), 3.11-3.25 (m, 2H), 3.35-3.43 (m, 1H), 3.47-3.69 (m, 4H), 3.83-3.91 (m, 2H), 4.04-4.17 (m, 2H), 4.59-4.64 (m, 1H), 6.81-6.83 (m, 2H), 7.14 (s, 1H), 7.22-7.26 (m, 1H), 7.30-7.32 (m, 1H), 7.47-7.51 (m, 2H), 7.57 (s, 1H), 7.63-7.65 (m, 1H), 7.98 (s, 1H), 8.09-8.11 (m, 2H) (4 exchangeable protons not observed) | m/z 801.6 (ES+), at 1.88, 95% |
| 8 | 3,5-dibromo-Nα-{[4-(2-oxo-2,3-dihydro-1H-imidazo[4,5-b]pyridin-1-yl)piperidin-1-yl]carbonyl}-N-{(2S)-1-oxo-3-(piperidin-4-yl)-1-[4-(pyridin-4-yl)piperazin-1-yl]propan-2-yl}-D-tyrosinamide | 11, 17 Procedure 1 | (400 MHz, MeOD) δ: ppm 1.26-1.51 (m, 5H), 1.51-1.72 (m, 2H), 1.72-1.92 (m, 3H), 1.96-2.08 (m, 1H), 2.08-2.38 (m, 2H), 2.79-3.05 (m, 5H), 3.33-3.42 (m, 3H), 3.54-3.64 (m, 1H), 3.64-3.79 (m, 3H), 3.81-4.05 (m, 4H), 4.17 (d, J = 12.9, 2H), 4.35-4.45 (m, 1H), 7.07 (dd, J = 7.8, 5.5, 1H), 7.14 (d, J = 7.4, 2H), 7.42-7.52 (m, 3H), 7.95 (d, J = 4.3, 1H), 8.14 (d, J = 7.4, 2H) | m/z 882.5, 884.2 (ES$^+$), at 2.47 min, 100% |
| 9 | 3,5-dibromo-Nα-{[4-(2-oxo-1,4-dihydroquinazolin-3(2H)-yl)piperidin-1-yl]carbonyl}-N-{(2S)-1-oxo-3-(piperidin-4-yl)-1-[4-(pyridin-4-yl)piperazin-1-yl]propan-2-yl}-D-tyrosinamide | 12, 17 Procedure 1 | (400 MHz, DMSO-d$_6$) δ: ppm 0.68-0.78 (m, 1H), 0.85-1.04 (m, 1H), 1.07-1.18 (m, 1H), 1.21-1.39 (m, 2H), 1.39-1.60 (m, 5H), 1.60-1.79 (m, 2H), 1.86-2.14 (m, 2H), 2.53-2.86 (m, 6H), 2.87-3.12 (m, 4H), 3.55-3.75 (m, 3H), 3.75-3.96 (m, 1H), 3.97-4.10 (m, 2H), 4.11-4.33 (m, 3H), 4.72-4.82 (m, 1H), 6.52 (t, J = 8.6, 1H), 6.78 (td, J = 7.4, 16.8, 4H), 7.00-7.18 (m, 2H), 7.22-7.29 (m, 2H), 7.58-7.65 (m, 1H), 7.88 (d, J = 7.8, 1H), 7.99-8.06 (m, 1H), 8.07-8.25 (m, 2H), 9.16 (s, 1H) | m/z 894.4, 896.5, 898.4 (ES$^+$), at 2.26 and 2.47 min, 100% |

TABLE 2-continued

| Ex. No. | Name | Intermediates/ Procedure | ¹H NMR | LCMS data (Method A) |
|---|---|---|---|---|
| 10 | N-[(2R)-3-(7-methyl-1H-indazol-5-yl)-1-oxo-1-({(2S)-1-oxo-3-(piperidin-4-yl)-1-[4-(pyridin-4-yl)piperazin-1-yl]propan-2-yl}amino)propan-2-yl]-4-(2-oxo-1,4-dihydroquinazolin-3(2H)-yl)piperidine-1-carboxamide | 13, 17 Procedure 1 | (400 MHz, DMSO-d₆) δ: ppm 1.12-1.57 (m, 8H), 1.66 (d, J = 12.5, 1H), 1.85 (d, J = 12.5, 1H), 2.52-2.78 (m, 4H), 2.89 (t, J = 10.9, 1H), 2.95-3.06 (m, 1H), 3.10-3.30 (m, 2H), 3.42-3.54 (m, 1H), 3.61 (d, J = 5.1, 4H), 3.72-3.90 (m, 4H), 3.91-4.13 (m, 4H), 4.14-4.37 (m, 3H), 4.78-4.92 (m, 2H), 6.65 (d, J = 7.8, 1H), 6.74 (d, J = 7.8, 1H), 6.85 (t, J = 7.4, 1H), 7.03 (d, J = 7.0, 1H), 7.08-7.20 (m, 4H), 7.45 (s, 1H), 7.98 (s, 1H), 8.27 (d, J = 5.9, 3H), 8.43 (d, J = 8.6, 1H), 8.55 (d, J = 9.0, 1H), 9.21 (s, 1H), 13.53 (br s, 1H) | m/z 774.7 (ES⁻), 776.6 (ES⁺), at 3.62 min, 100% |
| 11 | N-[(2R)-3-(7-methyl-1H-indazol-5-yl)-1-oxo-1-({(2S)-1-oxo-3-(piperidin-4-yl)-1-[4-(pyridin-4-yl)piperazin-1-yl]propan-2-yl}amino)propan-2-yl]-2'-oxo-1',2'-dihydro-1H-spiro[piperidine-4,4'-pyrido[2,3-d][1,3]oxazine]-1-carboxamide | 7, 17 Procedure 1 | (400 MHz, CD₃OD) δ: ppm 1.06-1.20 (m, 4H), 1.22-1.32 (m, 1H), 1.39-1.58 (m, 5H), 1.76-1.83 (m, 2H), 1.84-1.95 (m, 2H), 2.45-2.56 (m, 2H), 2.53 (s, 3H), 3.02 (dd, J = 13.8, 9.2, 2H), 3.15-3.27 (m, 2H), 3.38-3.42 (m, 1H), 3.48-3.59 (m, 3H), 3.59-3.74 (m, 2H), 3.83-3.99 (m, 4H), 4.63 (dd, J = 9.0, 6.8, 1H), 6.80-6.86 (m, 2H), 7.06 (dd, J = 7.7, 5.0, 1H), 7.12-7.21 (m, 2H), 7.48 (s, 1H), 7.97 (s, 1H), 8.11-8.15 (m, 2H), 8.17-8.20 (m, 1H) (5 exchangeable protons not observed) | m/z 762.8 (ES⁻), 764.7 (ES⁺), at 3.41 min, 100% |
| 12 | N-[(2R)-1-({(2S)-3-{1-[2-(dimethylamino)ethyl]piperidin-4-yl}-1-oxo-1-[4-(pyridin-4-yl)piperazin-1-yl]propan-2-yl}amino)-3-(7-methyl-1H-indazol-5-yl)-1-oxopropan-2-yl]-4-(2-oxo-2,3-dihydro-1H-imidazo[4,5-b]pyridin-1-yl)piperidine-1-carboxamide | 8, 22 Procedure 1, Step 1 | (400 MHz, CD₃OD) δ: ppm 0.98-1.22 (m, 3H), 1.37-1.51 (m, 3H), 1.60-1.77 (m, 6H), 2.00-2.09 (m, 1H), 2.17-2.26 (m, 2H), 2.30 (s, 6H), 2.42-2.54 (m, 7H), 2.78-2.93 (m, 4H), 3.02-3.08 (m, 1H), 3.15-3.20 (m, 1H), 3.31-3.42 (m, 1H), 3.48-3.56 (m, 3H), 3.61-3.65 (m, 1H), 3.86-3.92 (m, 2H), 4.12-4.16 (m, 2H), 4.37-4.44 (m, 1H), 4.60 (t, J = 7.8, 1H), 6.80-6.85 (m, 2H), 6.97 (dd, J = 7.8, 5.1, 1H), 7.16 (s, 1H), 7.34 (dd, J = 7.8, 1.2, 1H), 7.49 (s, 1H), 7.92 (dd, J = 5.1, 1.2, 1H), 7.97 (s, 1H), 8.08-8.19 (m, 2H) (4 exchangeable protons not observed) | m/z 835.7 (ES+), at 3.19, 95% |
| 13 | 3-(4-{(2S)-2-{[(2R)-3-(7-methyl-1H-indazol-5-yl)-2-({[4-(2-oxo-2,3-dihydro-1H-imidazo[4,5-b]pyridin-1-yl)piperidin-1-yl]carbonyl}amino)propanoyl]amino}-3-oxo-3-[4-(pyridin-4-yl)piperazin-1-yl]propyl}piperidin-1-yl)-3-oxopropanoic acid, ammonium salt | 8, 23 Procedure 3 | (400 MHz, CD₃OD) δ: ppm 0.57-0.73 (m, 2H), 0.86-1.10 (m, 4H), 1.21-1.40 (m, 3H), 2.16 (s, 3H), 2.26-2.44 (m, 4H), 2.52-2.67 (m, 2H), 2.74-2.95 (m, 3H), 3.03-3.41 (m, 7H), 3.46-3.62 (m, 6H), 3.79-4.06 (m, 4H), 6.32-6.36 (m, 2H), 6.56-6.59 (m, 1H), 6.68-6.83 (m, 2H), 7.15 (br s, 1H), 7.68 (br s, 1H), 7.69-7.74 (m, 2H), 7.90-7.93 (m, 1H) (8 exchangeable protons not observed) | m/z 849.8 (ES+), at 1.82, 95% |
| 14 | 3,5-dibromo-Nα-[(2'-oxo-1',2'-dihydro-1H-spiro[piperidine-4,4'-pyrido[2,3-d][1,3]oxazin]-1-yl)carbonyl]-N-{(2S)-1-oxo-3-(piperidin-4-yl)-1-[4-(pyridin-4-yl)piperazin-1-yl]propan-2-yl}-D-tyrosinamide | 14, 17 Procedure 1 | (400 MHz, CD₃OD) δ: ppm 0.96-1.20 (m, 5H), 1.23-1.48 (m, 3H), 1.58 (ddd, J = 14.3, 9.6, 4.3, 1H), 1.65-1.74 (m, 1H), 1.80-2.06 (m, 5H), 2.62 (td, J = 12.7, 3.1, 1H), 2.77-2.99 (m, 3H), 3.45-3.64 (m, 4H), 3.81-4.04 (m, 4H), 4.48 (dd, J = 9.4, 7.0, 1H), 6.82-6.85 (m, 2H), 7.08 (dd, J = 7.6, 4.9, 1H), 7.28 (s, 2H), 7.34 (s, 1H), 7.56 (dd, J = 7.6, 1.8, 1H), 8.11-8.20 (m, 3H) (2 protons obscured by solvent peaks, 5 exchangeable protons not observed) | m/z 884.5 (ES⁺), at 2.27 min, 100% |

Biological and Biophysical Methods

Cloning, Baculovirus Generation, Large-Scale Infection of Sf21 Cells and Membrane Preparation.

Human Calcitonin Receptor Like Receptor (CRLR) and human RAMP1 were cloned into Invitrogen's (Thermo-Fisher Scientific, UK) pFastBac dual expression vector. Transposition of CRLR/RAMP1 DNA was performed using Invitrogen's Bac-to-Bac Baculovirus Expression Systems. P0 baculovirus was generated by transfecting SF9 cells with bacmid DNA using Cellfectin® II transfection reagent (ThermoFisher Scientific, UK, catalog number 10362-100). Following P0 generation P1 virus was then generated ready for large scale infection and membrane preparation. Sf21 cells were grown in expression medium ESF921 (Expression Systems, USA, catalog number 96-001-01) supplemented with 10% heat-inactivated FBS and 1% Pen/Strep and were infected at a cell density of $2.5 \times 10^6$ cells/mL and an MOI of 2. Expression was carried out over 48 h in a shaking incubator set at 27° C. The cell culture was centrifuged at 2,500 rcf for 10 min at 4° C. The pellets were resuspended in cold PBS supplemented with Roche's Complete EDTA-free protease inhibitor cocktail tablets (Roche Applied Sciences, catalog number 05056489001), 1 mM PMSF and 1 mM EDTA. The resuspended cell paste was then centrifuged at 3,273 rcf for 12 min at 4° C. The supernatant was discarded and the pellet frozen at −80° C. The cell pellet from a 4 L culture was resuspended in buffer containing 50 mM Hepes pH 7.5, 150 mM NaCl, 8 Roche EDTA-free protease inhibitor cocktail tablets and 1 mM PMSF. The suspension was left stirring at rt for 1 h and then homogenised for 90 s at 9,500 rpm using a VDI 25 (VWR, USA) homogeniser. The cells were then lysed using a Microfluidizer processor M-110L Pneumatic (Microfluidics, USA). After lysis, the mixture was homogenised for 90 s at 9,500 rpm and then centrifuged at 335 rcf for 10 min. The supernatant was then further ultra-centrifuged at 42,000 rpm for 90 min. After ultra-centrifugation, the supernatant was discarded and the pellet was resuspended in 50 mL (25 mL for each 2 L culture) of buffer containing 50 mM Hepes pH 7.5, 150 mM NaCl, 3 Roche EDTA-free protease inhibitor cocktail tablets and 1 mM PMSF. The suspension was then homogenised for 90 s at 9,500 rpm. The resulting membranes were then stored at −80° C.

Radioligand Binding Assay.

Human CGRP receptors expressed (consisting of CRLR and RAMP1) in insect Sf21 cell membrane homogenates were re-suspended in the binding buffer (10 mM HEPES, pH 7.4, 5 mM $MgCl_2$, 0.2% BSA) to a final assay concentration of 0.6 µg protein per well. Saturation isotherms were determined by the addition of various concentrations of $^3$H-telcagepant (Ho et al, *The Lancet,* 2008, 372, 2115) (in a total reaction volume of 250 µL) for 60 min at rt. At the end of the incubation, membranes were filtered onto a unifilter, a 96-well white microplate with bonded GF/B filter pre-incubated with 0.5% PEI, with a Tomtec cell harvester and washed 5 times with distilled water. Non-specific binding (NSB) was measured in the presence of 10 nM MK-3207 hydrochloride (CAS No. 957116-20-0). Radioactivity on the filter was counted (1 min) on a microbeta counter after addition of 50 µL of scintillation fluid. For inhibition experiments, membranes were incubated with 0.5 nM $^3$H-telcagepant and 10 concentrations of the inhibitory compound (0.001-10 µM). $IC_{50}$ values were derived from the inhibition curve and the affinity constant ($K_i$) values were calculated using the Cheng-Prussoff equation (Cheng et al, *Biochem. Pharmacol.* 1973, 22, 3099-3108). The $pK_i$ values (where $pK_i = -\log_{10} K_i$) of certain compounds of the invention are tabulated below.

cAMP Functional Assay.

cAMP production following receptor activation was determined using the Homogeneous Time-Resolved Fluorescence (HTRF) cAMP dynamic-2 assay (Cisbio, France). The human neuroblastoma cell line SK-N-MC endogenously expressing the human CGRP receptor was seeded at a density of 12,500 cells/well in solid walled 96 well half area plates (Costar, Catalog Number 3688, Corning Life Sciences, Germany). After 16 h incubation at 37° C. media was removed and cells were incubated at 37° C. for 30 min in serum free media containing 500 µM IBMX (Tocris, Abingdon, UK, Catalog Number 2845) and increasing concentrations of test antagonist. Following this cells were challenged with an $EC_{80}$ concentration of human CGRP (0.3 nM) for a further 30 min at 37° C. and then cAMP production was determined as manufacturer's instructions before plates were read on a PheraStar fluorescence plate reader (BMG LabTech, Germany). $IC_{50}$ values were derived from the inhibition curve. The $pIC_{50}$ values (where $pIC_{50} = -\log_{10} IC_{50}$) were converted to a functional $pK_b$ value using a modified Cheng-Prussoff equation where $K_d$=agonist $EC_{50}$ and L hot=agonist challenge concentration. The $pK_b$ values of certain compounds of the invention are detailed in Table 3.

TABLE 3

| Ex No. | Name | Structure | pK$_i$ average | pK$_b$ average |
|---|---|---|---|---|
| 1 | N-[(2R)-3-(7-methyl-1H-indazol-5-yl)-1-oxo-1-({(2S)-1-oxo-3-(piperidin-4-yl)-1-[4-(pyridin-4-yl)piperazin-1-yl]propan-2-yl}amino)propan-2-yl]-4-(2-oxo-2,3-dihydro-1H-imidazo[4,5-b]pyridin-1-yl)piperidine-1-carboxamide | 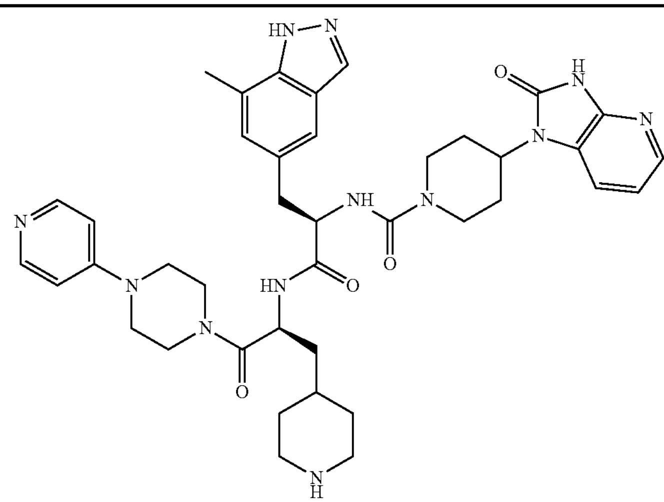 | 10.7 | 11.2 |

TABLE 3-continued

| Ex No. | Name | Structure | pK$_i$ average | pK$_b$ average |
|---|---|---|---|---|
| 2 | tert-butyl 4-{(2S)-2-{[(2R)-3-(7-methyl-1H-indazol-5-yl)-2-({[4-2-oxo-1,2-dihydroquinolin-3-yl)piperidin-1-yl]carbonyl}amino)propanoyl]amino}-3-oxo-3-[4-(pyridin-4-yl)piperazin-1-yl]propyl}piperidine-1-carboxylate | 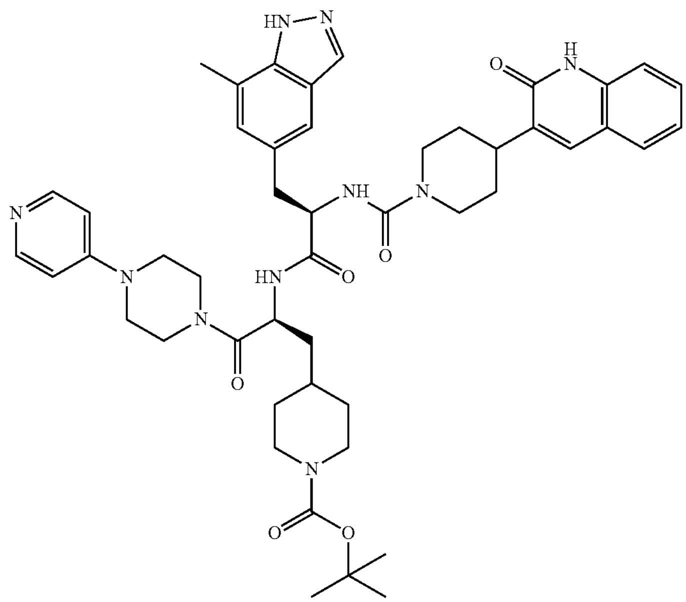 [SMILES: Cc1cc(C[C@@H](NC(=O)N2CCC(c3cc4ccccc4[nH]c3=O)CC2)C(=O)N[C@@H](CC2CCN(C(=O)OC(C)(C)C)CC2)C(=O)N2CCN(c3ccncc3)CC2)cc2cn[nH]c12] | 10.0 | 9.7 |
| 3 | N-[(2R)-3-(7-methyl-1H-indazol-5-yl)-1-oxo-1-({(2S)-1-oxo-3-(piperidin-4-yl)-1-[4-(pyridin-4-yl)piperazin-1-yl]propan-2-yl}amino)propan-2-yl]-4-(2-oxo-1,2-dihydroquinolin-3-yl)piperidine-1-carboxamide | 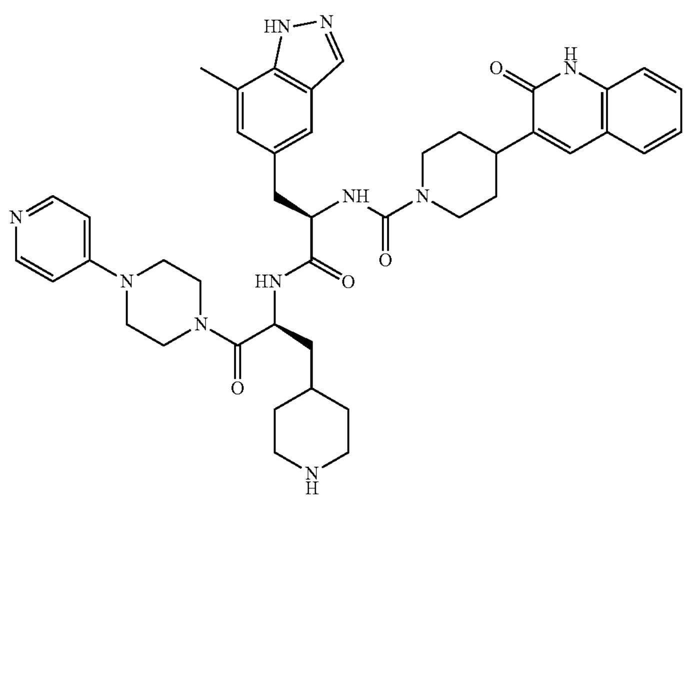 [SMILES: Cc1cc(C[C@@H](NC(=O)N2CCC(c3cc4ccccc4[nH]c3=O)CC2)C(=O)N[C@@H](CC2CCNCC2)C(=O)N2CCN(c3ccncc3)CC2)cc2cn[nH]c12] | 10.1 | 9.8 |

TABLE 3-continued

| Ex No. | Name | Structure | pK_i average | pK_b average |
|---|---|---|---|---|
| 4 | N-[(2R)-3-(7-methyl-1H-indazol-5-yl)-1-oxo-1-({(2S)-1-oxo-3-(1-propylpiperidin-4-yl)-1-[4-(pyridin-4-yl)piperazin-1-yl]propan-2-yl}amino)propan-2-yl]-4-(2-oxo-1,2-dihydroquinolin-3-yl)piperidine-1-carboxamide | 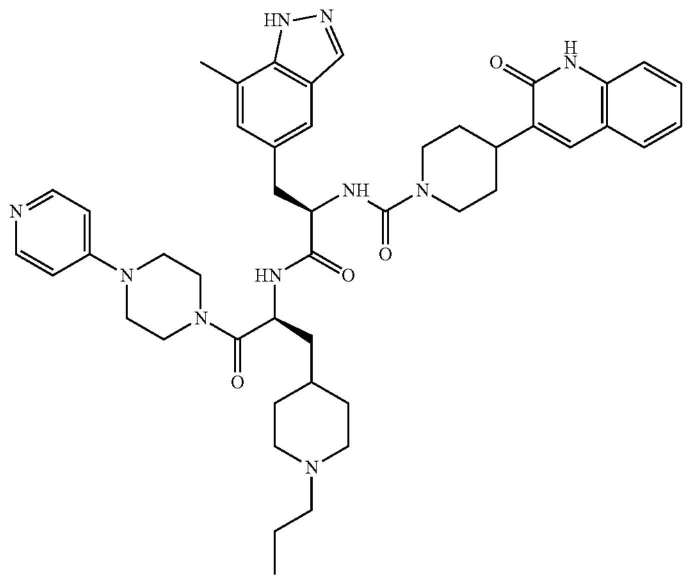 [SMILES: CCCN1CCC(C[C@H](NC(=O)[C@@H](Cc2cc(C)c3[nH]ncc3c2)NC(=O)N2CCC(c3cc4ccccc4[nH]c3=O)CC2)C(=O)N2CCN(c3ccncc3)CC2)CC1] | 10.4 | 10.7 |
| 5 | 3,5-dibromo-Nα-{[4-(2-oxo-1,2-dihydroquinolin-3-yl)piperidin-1-yl]carbonyl}-N-{(2S)-1-oxo-3-(piperidin-4-yl)-1-[4-(pyridin-4-yl)piperazin-1-yl]propan-2-yl}-D-tyrosinamide | 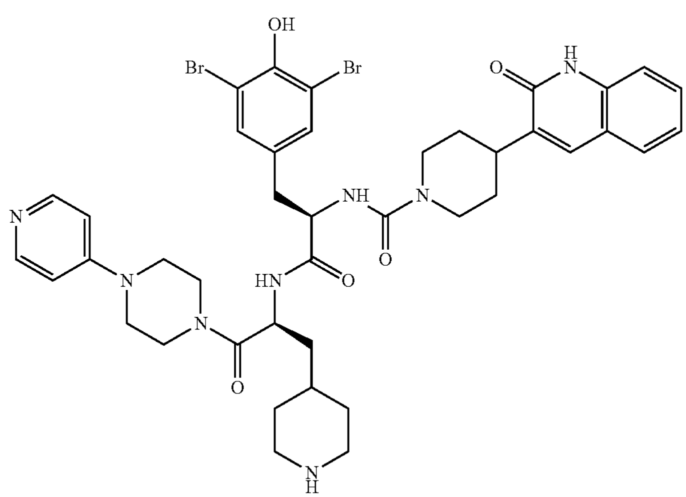 [SMILES: O=C(N[C@@H](CC1CCNCC1)C(=O)N1CCN(c2ccncc2)CC1)[C@@H](Cc1cc(Br)c(O)c(Br)c1)NC(=O)N1CCC(c2cc3ccccc3[nH]c2=O)CC1] | 10.2 | 9.6 |

TABLE 3-continued

| Ex No. | Name | Structure | pK$_i$ average | pK$_b$ average |
|---|---|---|---|---|
| 6 | N-[(2R)-3-(7-methyl-1H-indazol-5-yl)-1-oxo-1-({(2S)-1-oxo-3-(1-pentanoylpiperidin-4-yl)-1-[4-(pyridin-4-yl)piperazin-1-yl]propan-2-yl}amino)propan-2-yl]-4-(2-oxo-1,2-dihydroquinolin-3-yl)piperidine-1-carboxamide | 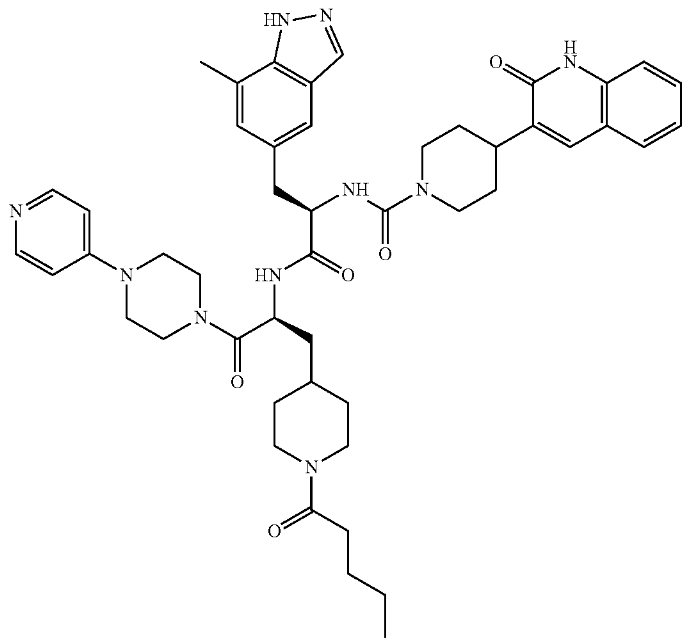 [SMILES: CCCCC(=O)N1CCC(C[C@H](NC(=O)[C@@H](Cc2cc(C)c3[nH]ncc3c2)NC(=O)N2CCC(c3cc4ccccc4[nH]c3=O)CC2)C(=O)N2CCN(c3ccncc3)CC2)CC1] | 10.0 | 10.0 |
| 7 | N-[(2R)-1-({(2S)-3-(1-ethylpiperidin-4-yl)-1-oxo-1-[4-(pyridin-4-yl)piperazin-1-yl]propan-2-yl}amino)-3-(7-methyl-1H-indazol-5-yl)-1-oxopropan-2-yl]-4-(2-oxo-1,2-dihydroquinolin-3-yl)piperidine-1-carboxamide | 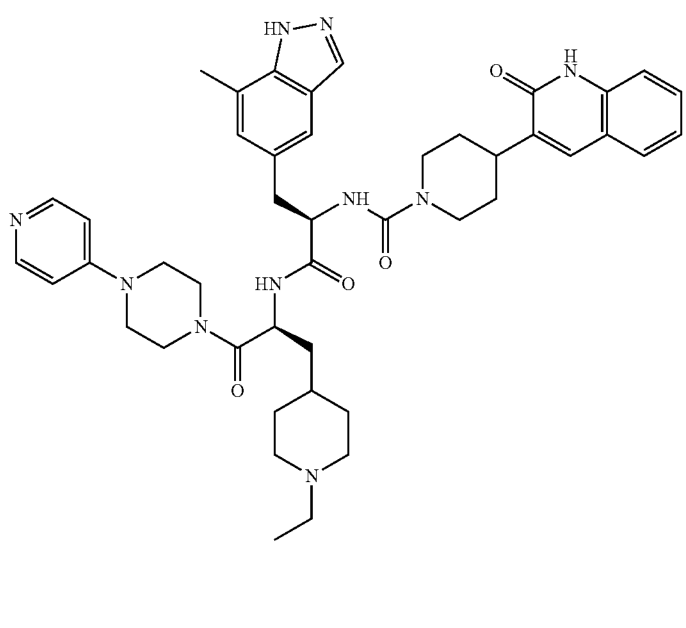 [SMILES: CCN1CCC(C[C@H](NC(=O)[C@@H](Cc2cc(C)c3[nH]ncc3c2)NC(=O)N2CCC(c3cc4ccccc4[nH]c3=O)CC2)C(=O)N2CCN(c3ccncc3)CC2)CC1] | 10.4 | 10.6 |

TABLE 3-continued

| Ex No. | Name | Structure | pK$_i$ average | pK$_b$ average |
| --- | --- | --- | --- | --- |
| 8 | 3,5-dibromo-Nα-{[4-(2-oxo-2,3-dihydro-1H-imidazo[4,5-b]pyridin-1-yl)piperidin-1-yl]carbonyl}-N-{(2S)-1-oxo-3-(piperidin-4-yl)-1-[4-(pyridin-4-yl)piperazin-1-yl]propan-2-yl}-D-tyrosinamide | 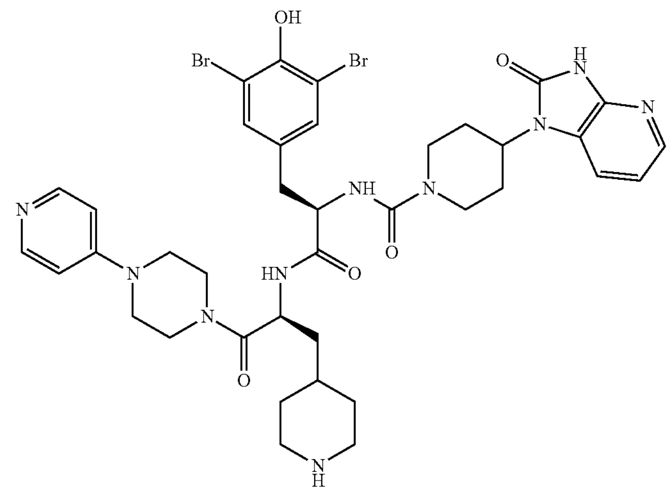 [SMILES: O=C(N[C@@H](CC1CCNCC1)C(=O)N1CCN(c2ccncc2)CC1)[C@@H](Cc1cc(Br)c(O)c(Br)c1)NC(=O)N1CCC(n2c(=O)[nH]c3ncccc32)CC1] | 10.4 | 10.8 |
| 9 | 3,5-dibromo-Nα-{[4-(2-oxo-1,4-dihydroquinazolin-3(2H)-yl)piperidin-1-yl]carbonyl}-N-{(2S)-1-oxo-3-(piperidin-4-yl)-1-[4-(pyridin-4-yl)piperazin-1-yl]propan-2-yl}-D-tyrosinamide | 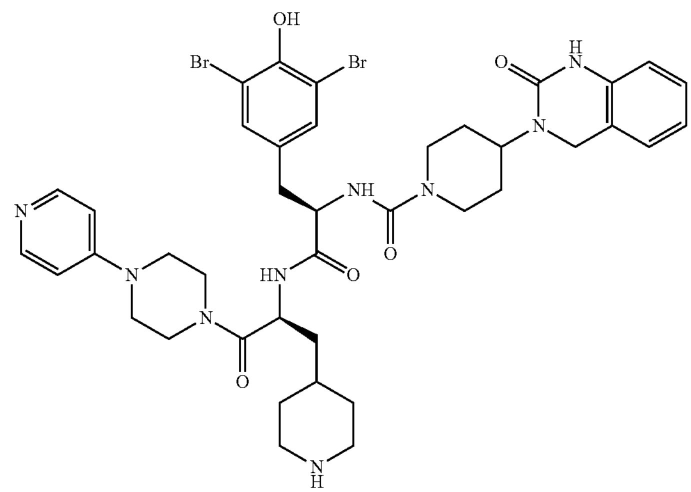 [SMILES: O=C(N[C@@H](CC1CCNCC1)C(=O)N1CCN(c2ccncc2)CC1)[C@@H](Cc1cc(Br)c(O)c(Br)c1)NC(=O)N1CCC(N2Cc3ccccc3NC2=O)CC1] | 10.1 | 11.2 |
| 10 | N-[(2R)-3-(7-methyl-1H-indazol-5-yl)-1-oxo-1-({(2S)-1-oxo-3-(piperidin-4-yl)-1-[4-(pyridin-4-yl)piperazin-1-yl]propan-2-yl}amino)propan-2-yl]-4-(2-oxo-1,4-dihydroquinazolin-3(2H)-yl)piperidine-1-carboxamide | 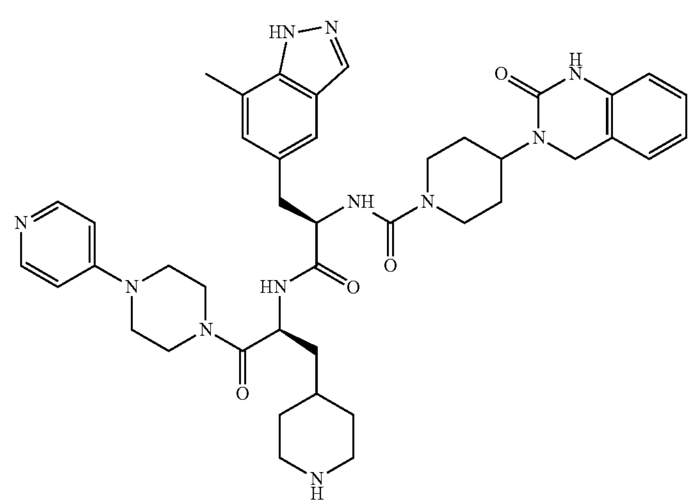 [SMILES: Cc1cc(C[C@@H](NC(=O)N2CCC(N3Cc4ccccc4NC3=O)CC2)C(=O)N[C@@H](CC2CCNCC2)C(=O)N2CCN(c3ccncc3)CC2)cc2cn[nH]c12] | 10.2 | 10.1 |

TABLE 3-continued

| Ex No. | Name | Structure | pK$_i$ average | pK$_b$ average |
|---|---|---|---|---|
| 11 | N-[(2R)-3-(7-methyl-1H-indazol-5-yl)-1-oxo-1-({(2S)-1-oxo-3-(piperidin-4-yl)-1-[4-(pyridin-4-yl)piperazin-1-yl]propan-2-yl}amino)propan-2-yl]-2'-oxo-1',2'-dihydro-1H-spiro[piperidine-4,4'-pyrido[2,3-d][1,3]oxazine]-1-carboxamide | 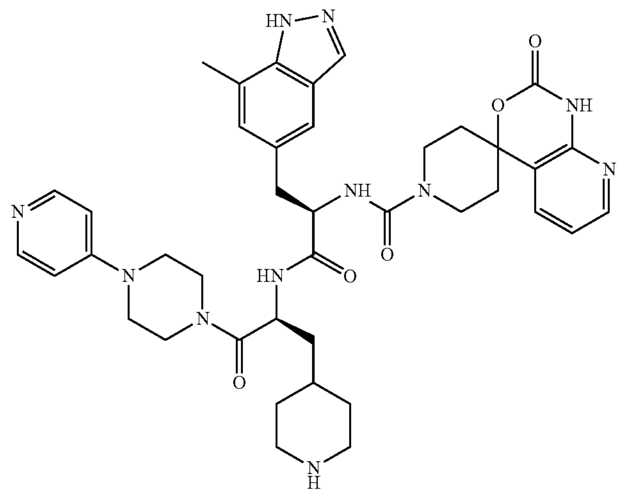 [SMILES: Cc1cc(C[C@@H](NC(=O)N2CCC3(CC2)OC(=O)Nc2ncccc23)C(=O)N[C@@H](CC2CCNCC2)C(=O)N2CCN(c3ccncc3)CC2)cc2cn[nH]c12] | 10.5 | 10.3 |
| 12 | N-[(2R)-1-({(2S)-3-{1-[2-(dimethylamino)ethyl]piperidin-4-yl}-1-oxo-1-[4-(pyridin-4-yl)piperazin-1-yl]propan-2-yl}amino)-3-(7-methyl-1H-indazol-5-yl)-1-oxopropan-2-yl]-4-(2-oxo-2,3-dihydro-1H-imidazo[4,5-b]pyridin-1-yl)piperidine-1-carboxamide | 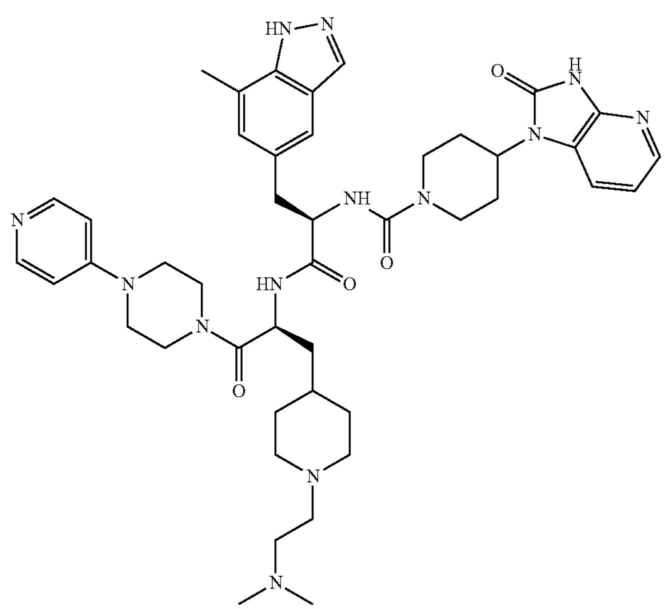 [SMILES: Cc1cc(C[C@@H](NC(=O)N2CCC(n3c(=O)[nH]c4ncccc43)CC2)C(=O)N[C@@H](CC2CCN(CCN(C)C)CC2)C(=O)N2CCN(c3ccncc3)CC2)cc2cn[nH]c12] | 10.6 | 10.6 |

TABLE 3-continued

| Ex No. | Name | Structure | pK$_i$ average | pK$_b$ average |
|---|---|---|---|---|
| 13 | 3-(4-{(2S)-2-{[(2R)-3-(7-methyl-1H-indazol-5-yl)-2-({[4-(2-oxo-2,3-dihydro-1H-imidazo[4,5-b]pyridin-1-yl)piperidin-1-yl]carbonyl}amino)propanoyl]amino}-3-oxo-3-[4-(pyridin-4-yl)piperazin-1-yl]propyl}piperidin-1-yl)-3-oxopropanoic acid, ammonium salt | 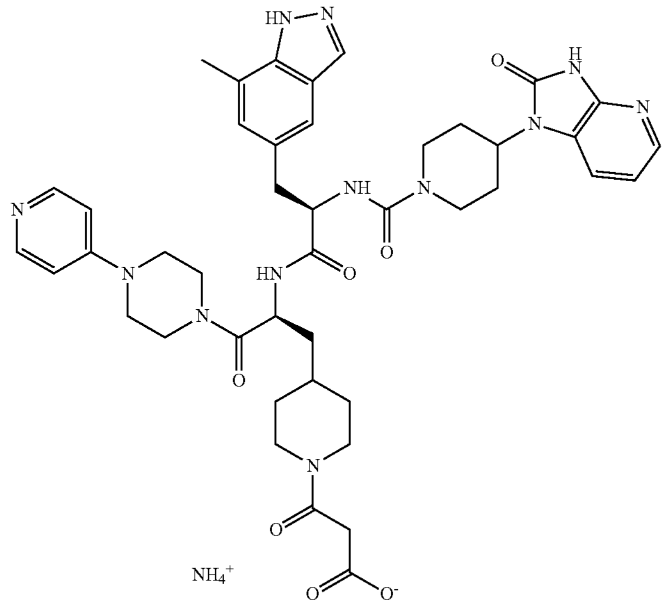 [SMILES: Cc1cc(C[C@@H](NC(=O)N2CCC(n3c(=O)[nH]c4ncccc43)CC2)C(=O)N[C@@H](CC2CCN(C(=O)CC(=O)[O-])CC2)C(=O)N2CCN(c3ccncc3)CC2)cc2cn[nH]c12 ; [NH4+]] | 10.0 | 9.9 |
| 14 | 3,5-dibromo-Nα-[(2'-oxo-1',2'-dihydro-1H-spiro[piperidine-4,4'-pyrido[2,3-d][1,3]oxazin]-1-yl)carbonyl]-N-{(2S)-1-oxo-3-(piperidin-4-yl)-1-[4-(pyridin-4-yl)piperazin-1-yl]propan-2-yl}-D-tyrosinamide | 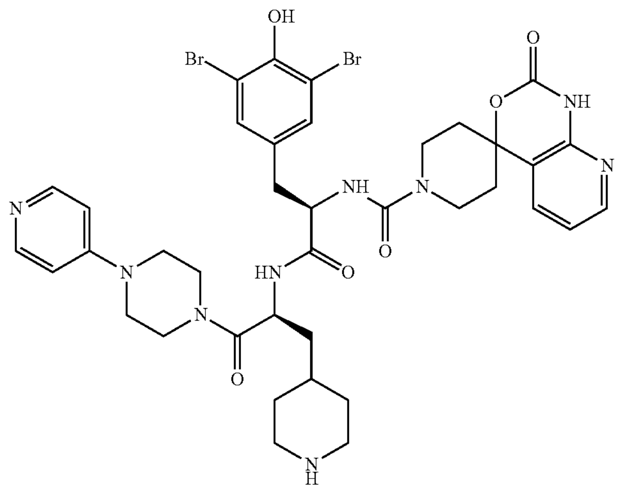 [SMILES: O=C1Nc2ncccc2C2(CCN(C(=O)N[C@H](Cc3cc(Br)c(O)c(Br)c3)C(=O)N[C@@H](CC3CCNCC3)C(=O)N3CCN(c4ccncc4)CC3)CC2)O1] | 10.1 | 10.8 |

Receptor Kinetic Profiling.

It is appreciated that the kinetic profile of a small molecule at the relevant biological target can have an impact upon the pharmacodynamic effect of the molecule in vivo (Copeland, *Expert Opin. Drug Discov.*, 2010, 5, 305). For example, olcegepant has slow kinetics at the CGRP receptor (Schindler, Doods, *Eur. J. Pharmacol.*, 2002, 442, 187), a factor which may contribute to its prolonged efficacy in migraine treatment in humans (47% headache-free rate at 24 h after intravenous infusion of a 2.5 mg dose; Olesen et al, *N. Eng. J. Med.*, 2004, 350, 1104). In a similar way, MK-3207 has also been shown to demonstrate relatively slow dissociation for the CGRP receptor (Salvatore et al, *J. Pharmacol. Exp. Ther.*, 2010, 333, 152). The CGRP receptor kinetics of compounds of the invention and reference CGRP receptor antagonists have been profiled using the surface plasmon resonance technique below, and are detailed in Table 4.

Kinetic analyses were run on a Biacore T200 instrument (GE Healthcare Bio-Sciences AB, Uppsala, Sweden) at 25° C. using 0.05 mM EDTA, PBS (10 mM phosphate buffer, 2.7 mM KCl, 137 mM NaCl) pH 7.4, 0.005% v/v Surfactant P20, 5% DMSO as the running buffer. The purified CGRP receptor ectodomain complex containing a hexa-His tag (Moore et al, *Structure*, 2010, 18, 1083-1093) was immobilised on a sensor chip NTA (GE Healthcare Bio-Sciences AB) by the capture-couple technique (Rich et al, *Anal. Biochem.*, 2011, 409, 267-272). The chip was loaded with $Ni^{2+}$ and carboxyl groups of the dextran matrix were activated by EDC/NHS. The receptor ectodomain complex (100 nM in running buffer) was then injected and immobilised via the His-tag and amino groups. Two fold dilution series of each compound (five concentrations, in the range 25-40 nM) were injected. Blank-subtracted data were fitted to a 1:1 interaction model to obtain kinetic parameters which are expressed in Table 4 as dissociation half-life ($t_{1/2}$=(ln 2/off-rate ($k_d$))/60).

The data presented indicates that each of the examples 2, 4, 6, 7, 8, 9, 11, 12 and 14 have the property of slow receptor dissociation that is comparable or slower in off-rate than olcegepant or MK-3207.

TABLE 4

| Reference Compound/Example | CGRP $t_{1/2}$ (min) |
|---|---|
| olcegepant | 30 |
| MK-3207 | 27 |
| telcagepant | 2 |
| BMS-927711 | 2 |
| Example 1 | 5 |
| Example 2 | 78 |
| Example 3 | 4 |
| Example 4 | 39 |
| Example 5 | 12 |
| Example 6 | 20 |
| Example 7 | 36 |
| Example 8 | 95 |
| Example 9 | 32 |
| Example 10 | 3 |
| Example 11 | 65 |
| Example 12 | 101 |
| Example 13 | Not determined |
| Example 14 | 38 |

Pharmacokinetic Profiling.

The pharmacokinetic profiles of Examples and reference compounds have been assessed in male Sprague Dawley® rats via intravenous (iv), sub-cutaneous (sc) and intranasal (IN) routes of delivery, and in male Cynomolgus Monkeys via iv and sc routes of delivery. Pharmacokinetic data for Examples of the invention and a reference compound, olcegepant, are detailed in Tables 5 and 6.

Methods:

For rat studies, groups of three male Sprague Dawley® rats, typically ranging in weight between 180 and 300 g, were given a single dose of Example or reference compound via one of the following routes: iv, sc or IN, using doses, dose volumes and vehicles specified in Table 5. Prior to IN dosing rats were anaesthetised with an intramuscular dose of 25-30 mg/kg ketamine cocktail (ketamine, xylazine hydrochloride and acepromazine maleate in saline) and the dose is introduced over 20-30 s via a polyethylene PE-10 tube inserted approximately 5 mm into the nasal cavity of the rat.

For cynomolgus monkey studies, groups of three male monkeys, typically ranging in weight between 3.0 and 4.5 kg, were given a single dose of Example or reference compound via one of the following routes: iv or sc, using doses, dose volumes and vehicles specified in Table 5. Following dosing by the routes above blood samples were taken at several time points (typically pre-dose, 0.083, 0.25, 0.5 1, 2, 4, 8 and 24 h) via serial tail vein bleeds (rat) or cephalic or saphenous vein (monkey) from the animal and centrifuged to separate plasma for analysis by LC/MS/MS assay. WinNonlin v6.2 statistics software (Pharsight Corporation, California, USA) was used to generate pharmacokinetic parameters using the non-compartmental model.

TABLE 5

| Rat iv pharmacokinetics | | | | |
|---|---|---|---|---|
| | Dose (mg/kg) | Dose volume (mL/kg) | Vehicle | Clearance (mL/min/kg) |
| olcegepant | 5 | 1 | 10% DMAC + 10% SolutolHS15 + 80% Saline | 18 |
| Example 11 | 2 | 1 | 10% DMAC + 10% SolutolHS15 + 80% Saline | 17 |
| Example 14 | 2 | 1 | 10% DMAC + 10% SolutolHS15 + 80% Saline | 22 |

| Rat sc pharmacokinetics | | | | |
|---|---|---|---|---|
| | Dose (mg/kg) | Dose volume (mL/kg) | Vehicle | Bioavailability (%) |
| olcegepant | 1 | 5 | 10% DMAC + 10% SolutolHS15 + 80% Saline | 48% |
| Example 11 | 1 | 2 | Acidified saline | 100% |
| Example 14 | 1 | 2 | Acidified saline | 96% |

| Rat IN pharmacokinetics | | | | |
|---|---|---|---|---|
| | Dose (mg/kg) | Dose concentration, Dose volume | Vehicle | Bioavailability (%) |
| olcegepant | 1.3 | 6 mg/mL, 50 µL | Acidified saline | 8 |
| Example 11 | 1 | 12 mg/mL, 25 µL | Acidified saline | 40 |
| Example 14 | 1 | 12 mg/mL, 25 µL | Acidified saline | 19 |

TABLE 6

| | Cynomolgus monkey iv pharmacokinetics | | | |
|---|---|---|---|---|
| | Dose (mg/kg) | Dose volume (mL/kg) | Vehicle | Clearance (mL/min/kg) |
| Example 11 | 0.5 | 1 | Acidified saline | 2 |
| Example 14 | 0.4 | 0.5 | Acidified saline | 3 |
| | Cynomolgus monkey sc pharmacokinetics | | | |
| | Dose (mg/kg) | Dose volume (mL/kg) | Vehicle | Bioavailability (%) |
| Example 11 | 0.5 | 1 | Acidified saline | 100 |
| Example 14 | Not tested | | | |

Thermodynamic Solubility Profiling.

A 50 mM DMSO stock solution of test compound was prepared, and from this, a working solution of 1 mM was prepared by dilution with DMSO. The UV absorbance of working solution was scanned from 220 nm to 1000 nm to identify the wavelength maxima of test compound. The 1 mM working solution was then serially diluted in DMSO to different concentrations to determine linearity/calibration curve. To ascertain the aqueous thermodynamic solubility of test compound, samples were added to a volume of PBS buffer (pH 7.4) or Sodium Phosphate Buffer (pH 6.0) which was appropriate to generate a final concentration of 1 mg/mL if all test compound dissolved. The resulting solution was then kept on a RotoSpin shaker at 50 rpm for 24 h at rt before the solution was filtered using 0.45 micron PVDF injector filters in order to remove the insoluble fraction of the compound. Subsequently, 150 uL of the filtrate is taken for quantification using a UV spectrophotometer, acquiring the optical density of standard solutions and test compound at the same wavelength maxima. From the optical density of test compound the thermodynamic solubility is calculated using the linearity/calibration curve and expressed as micromolar (μM). Solubility profiles of certain compounds of the invention are detailed in Table 7.

TABLE 7

| Reference Cpd/ Example | Thermodynamic solubility (μM) | |
|---|---|---|
| | pH 6 | pH 7.4 |
| olcegepant | 150 | 431 |
| Example 1 | 3387 | 3222 |
| Example 2 | Not tested | Not tested |
| Example 3 | 10 | 509 |
| Example 4 | Not tested | Not tested |
| Example 5 | 9 | 113 |
| Example 6 | Not tested | Not tested |
| Example 7 | Not tested | Not tested |
| Example 8 | 1029 | 890 |
| Example 9 | Not tested | Not tested |
| Example 10 | 1171 | 1205 |
| Example 11 | 1263 | 1426 |
| Example 12 | 1648 | 1955 |
| Example 13 | Not tested | Not tested |
| Example 14 | 1111 | 862 |

The invention claimed is:

1. A compound of formula (I)

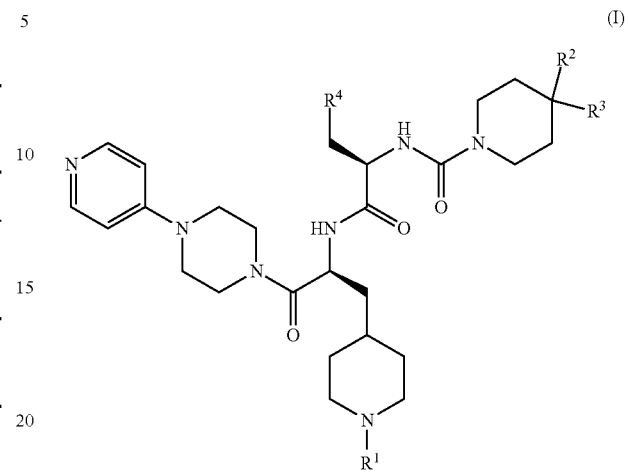

or a salt thereof or an optical isomer thereof, wherein $R^1$ is H or Q-$(C_1-C_6)$alkyl;
where Q is a bond, C(O) or C(O)O and where the $(C_1-C_6)$alkyl can be optionally substituted by $N(C_1-C_3\text{alkyl})_2$ or $CO_2H$;
$R^2$ is H or forms a spirocyclic heterocyclic ring with $R^3$;
$R^3$ forms a spirocyclic heterocyclic ring with $R^2$ or is a heterocyclic ring if $R^2$ is H; and
$R^4$ is an optionally substituted aryl group which may be monocyclic or fused to a further ring.

2. The compound according to claim 1, or a salt thereof or an optical isomer thereof, wherein $R^4$ is a substituted phenyl group wherein the substituents are selected from halo or hydroxy.

3. The compound according to claim 1, or a salt thereof or an optical isomer thereof, wherein $R^4$ is a moiety according to formula (II)

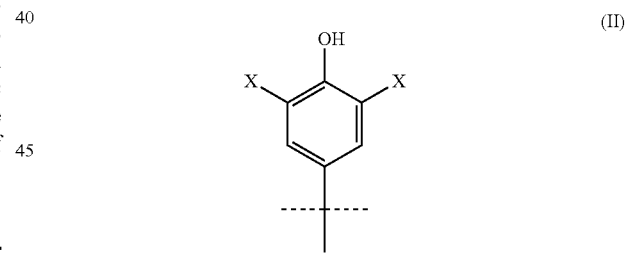

wherein X is halo.

4. The compound according to claim 3, or a salt thereof or an optical isomer thereof, wherein X is Br.

5. The compound according to claim 1, or a salt thereof or an optical isomer thereof, wherein $R^4$ is

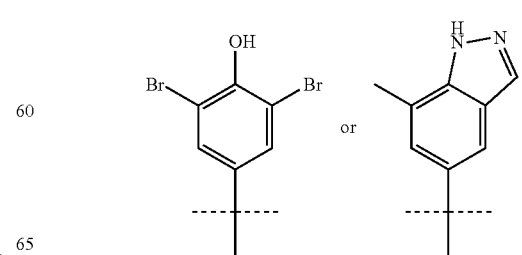

6. The compound according to claim 5, or a salt thereof or an optical isomer thereof, wherein $R^4$ is

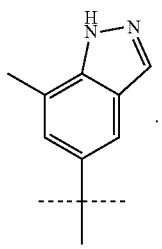

7. The compound according to claim 1, or a salt thereof or an optical isomer thereof, wherein $R^2$ is H and $R^3$ is:

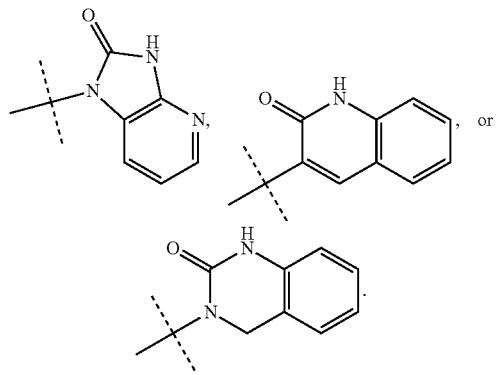

8. The compound according to claim 1, or a salt thereof or an optical isomer thereof, wherein $R^2$ forms a spirocyclic heterocyclic ring with $R^3$ to form:

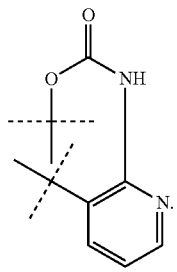

9. The compound according to claim 1, or a salt thereof or an optical isomer thereof, wherein $R^2$ is H or forms a spirocyclic heterocyclic ring with $R^3$ to form:

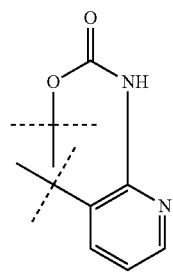

and wherein when $R^2$ is H, $R^3$ is:

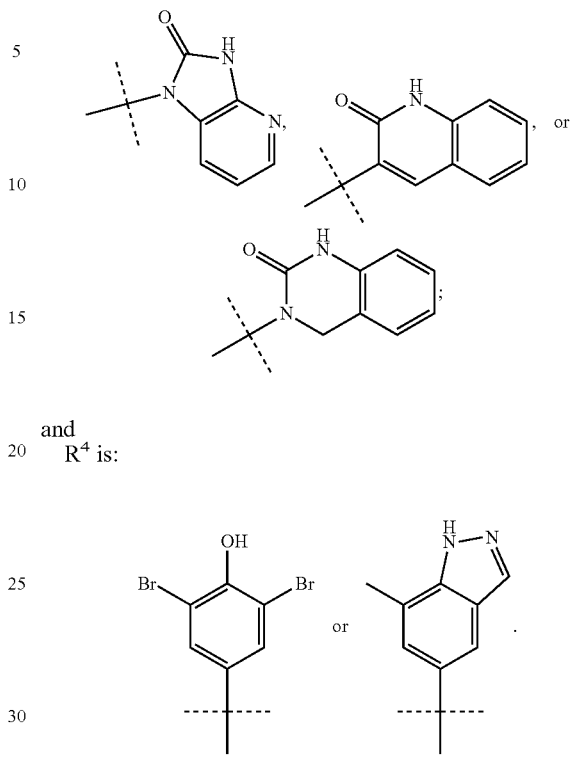

and
$R^4$ is:

10. The compound according to claim 1, or a salt thereof or an optical isomer thereof, wherein $R^1$ is H, $CO_2{}^tBu$, $CH_2CH_3$, $CH_2CH_2CH_3$, $COCH_2CH_2CH_2CH_3$, $CH_2CH_2N(CH_3)_2$, or $COCH_2CO_2H$.

11. The compound according to claim 10, or a salt thereof or an optical isomer thereof, wherein $R^1$ is H.

12. The compound according to claim 1, wherein the compound is selected from the group consisting of:
N-[(2R)-3-(7-methyl-1H-indazol-5-yl)-1-oxo-1-({(2S)-1-oxo-3-(piperidin-4-yl)-1-[4-(pyridin-4-yl)piperazin-1-yl]propan-2-yl}amino)propan-2-yl]-4-(2-oxo-2,3-dihydro-1H-imidazo[4,5-b]pyridin-1-yl)piperidine-1-carboxamide;
tert-butyl 4-{(2S)-2-{[(2R)-3-(7-methyl-1H-indazol-5-yl)-2-({[[4-(2-oxo-1,2-dihydroquinolin-3-yl)piperidin-1-yl]carbonyl}amino)propanoyl]amino}-3-oxo-3-[4-(pyridin-4-yl)piperazin-1-yl]propyl}piperidine-1-carboxylate;
N-[(2R)-3-(7-methyl-1H-indazol-5-yl)-1-oxo-1-({(2S)-1-oxo-3-(piperidin-4-yl)-1-[4-(pyridin-4-yl)piperazin-1-yl]propan-2-yl}amino)propan-2-yl]-4-(2-oxo-1,2-dihydroquinolin-3-yl)piperidine-1-carboxamide;
N-[(2R)-3-(7-methyl-1H-indazol-5-yl)-1-oxo-1-({(2S)-1-oxo-3-(1-propylpiperidin-4-yl)-1-[4-(pyridin-4-yl)piperazin-1-yl]propan-2-yl}amino)propan-2-yl]-4-(2-oxo-1,2-dihydroquinolin-3-yl)piperidine-1-carboxamide;
3,5-dibromo-Nα-{[4-(2-oxo-1,2-dihydroquinolin-3-yl)piperidin-1-yl]carbonyl}-N-{(2S)-1-oxo-3-(piperidin-4-yl)-1-[4-(pyridin-4-yl)piperazin-1-yl]propan-2-yl}-D-tyrosinamide;
N-[(2R)-3-(7-methyl-1H-indazol-5-yl)-1-oxo-1-({(2S)-1-oxo-3-(1-pentanoylpiperidin-4-yl)-1-[4-(pyridin-4-yl)piperazin-1-yl]propan-2-yl}amino)propan-2-yl]-4-(2-oxo-1,2-dihydroquinolin-3-yl)piperidine-1-carboxamide;

N-[(2R)-1-({(2S)-3-(1-ethylpiperidin-4-yl)-1-oxo-1-[4-(pyridin-4-yl)piperazin-1-yl]propan-2-yl}amino)-3-(7-methyl-1H-indazol-5-yl)-1-oxopropan-2-yl]-4-(2-oxo-1,2-dihydroquinolin-3-yl)piperidine-1-carboxamide;

3,5-dibromo-Nα-{[4-(2-oxo-2,3-dihydro-1H-imidazo[4,5-b]pyridin-1-yl)piperidin-1-yl]carbonyl}-N-{(2S)-1-oxo-3-(piperidin-4-yl)-1-[4-(pyridin-4-yl)piperazin-1-yl]propan-2-yl}-D-tyrosinamide;

3,5-dibromo-Nα-{[4-(2-oxo-1,4-dihydroquinazolin-3(2H)-yl)piperidin-1-yl]carbonyl}-N-{(2S)-1-oxo-3-(piperidin-4-yl)-1-[4-(pyridin-4-yl)piperazin-1-yl]propan-2-yl}-D-tyrosinamide;

N-[(2R)-3-(7-methyl-1H-indazol-5-yl)-1-oxo-1-({(2S)-1-oxo-3-(piperidin-4-yl)-1-[4-(pyridin-4-yl)piperazin-1-yl]propan-2-yl}amino)propan-2-yl]-4-(2-oxo-1,4-dihydroquinazolin-3(2H)-yl)piperidine-1-carboxamide;

N-[(2R)-3-(7-methyl-1H-indazol-5-yl)-1-oxo-1-({(2S)-1-oxo-3-(piperidin-4-yl)-1-[4-(pyridin-4-yl)piperazin-1-yl]propan-2-yl}amino)propan-2-yl]-2'-oxo-1',2'-dihydro-1H-spiro[piperidine-4,4'-pyrido[2,3-d][1,3]oxazine]-1-carboxamide;

N-[(2R)-1-({(2S)-3-{1-[2-(dimethylamino)ethyl]piperidin-4-yl}-1-oxo-1-[4-(pyridin-4-yl)piperazin-1-yl]propan-2-yl}amino)-3-(7-methyl-1H-indazol-5-yl)-1-oxopropan-2-yl]-4-(2-oxo-2,3-dihydro-1H-imidazo[4,5-b]pyridin-1-yl)piperidine-1-carboxamide;

3-(4-{(2S)-2-{[(2R)-3-(7-methyl-1H-indazol-5-yl)-2-({[4-(2-oxo-2,3-dihydro-1H-imidazo[4,5-b]pyridin-1-yl)piperidin-1-yl]carbonyl}amino)propanoyl]amino}-3-oxo-3-[4-(pyridin-4-yl)piperazin-1-yl]propyl}piperidin-1-yl)-3-oxopropanoic acid, ammonium salt; and 3, 5-dibromo-Nα-[(2'-oxo-1',2'-dihydro-1H-spiro[piperidine-4,4'-pyrido[2,3-d][1,3]oxazin]-1-yl)carbonyl]-N-{(2S)-1-oxo-3-(piperidin-4-yl)-1-[4-(pyridin-4-yl)piperazin-1-yl]propan-2-yl}-D-tyrosinamide;

or a salt thereof or an optical isomer thereof.

13. The compound according to claim 12, wherein the compound is:

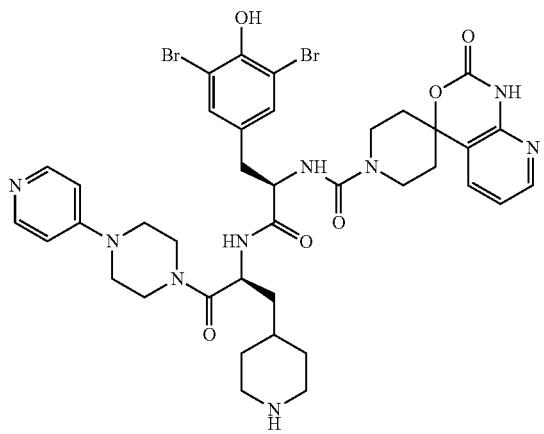 [SMILES: O=C1Nc2ncccc2C2(CCN(C(=O)N[C@H](Cc3cc(Br)c(O)c(Br)c3)C(=O)N[C@@H](CC3CCNCC3)C(=O)N3CCN(c4ccncc4)CC3)CC2)O1]

or a salt thereof or an optical isomer thereof.

14. The compound according to claim 12, wherein the compound is:

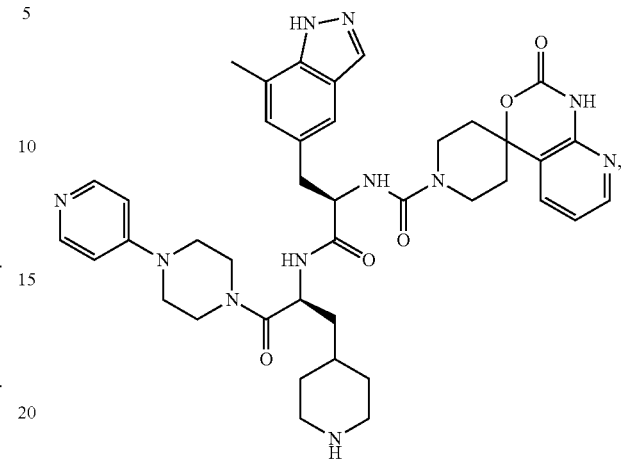

or a salt thereof or an optical isomer thereof.

15. The compound according to claim 1, wherein the compound is selected from the group consisting of:

N-[(2R)-3-(7-methyl-1H-indazol-5-yl)-1-oxo-1-({(2S)-1-oxo-3-(piperidin-4-yl)-1-[4-(pyridin-4-yl)piperazin-1-yl]propan-2-yl}amino)propan-2-yl]-4-(2-oxo-2,3-dihydro-1H-imidazo[4,5-b]pyridin-1-yl)piperidine-1-carboxamide;

tert-butyl 4-{(2S)-2-{[(2R)-3-(7-methyl-1H-indazol-5-yl)-2-({[4-(2-oxo-1,2-dihydroquinolin-3-yl)piperidin-1-yl]carbonyl}amino)propanoyl]amino}-3-oxo-3-[4-(pyridin-4-yl)piperazin-1-yl]propyl}piperidine-1-carboxylate;

N-[(2R)-3-(7-methyl-1H-indazol-5-yl)-1-oxo-1-({(2S)-1-oxo-3-(piperidin-4-yl)-1-[4-(pyridin-4-yl)piperazin-1-yl]propan-2-yl}amino)propan-2-yl]-4-(2-oxo-1,2-dihydroquinolin-3-yl)piperidine-1-carboxamide;

N-[(2R)-3-(7-methyl-1H-indazol-5-yl)-1-oxo-1-({(2S)-1-oxo-3-(1-propylpiperidin-4-yl)-1-[4-(pyridin-4-yl)piperazin-1-yl]propan-2-yl}amino)propan-2-yl]-4-(2-oxo-1,2-dihydroquinolin-3-yl)piperidine-1-carboxamide;

3,5-dibromo-Nα-{[4-(2-oxo-1,2-dihydroquinolin-3-yl)piperidin-1-yl]carbonyl}-N-{(2S)-1-oxo-3-(piperidin-4-yl)-1-[4-(pyridin-4-yl)piperazin-1-yl]propan-2-yl}-D-tyrosinamide;

N-[(2R)-3-(7-methyl-1H-indazol-5-yl)-1-oxo-1-({(2S)-1-oxo-3-(1-pentanoylpiperidin-4-yl)-1-[4-(pyridin-4-yl)piperazin-1-yl]propan-2-yl}amino)propan-2-yl]-4-(2-oxo-1,2-dihydroquinolin-3-yl)piperidine-1-carboxamide;

N-[(2R)-1-({(2S)-3-(1-ethylpiperidin-4-yl)-1-oxo-1-[4-(pyridin-4-yl)piperazin-1-yl]propan-2-yl}amino)-3-(7-methyl-1H-indazol-5-yl)-1-oxopropan-2-yl]-4-(2-oxo-1,2-dihydroquinolin-3-yl)piperidine-1-carboxamide;

3,5-dibromo-Nα-{[4-(2-oxo-2,3-dihydro-1H-imidazo[4,5-b]pyridin-1-yl)piperidin-1-yl]carbonyl}-N-{(2S)-1-oxo-3-(piperidin-4-yl)-1-[4-(pyridin-4-yl)piperazin-1-yl]propan-2-yl}-D-tyrosinamide;

3,5-dibromo-Nα-{[4-(2-oxo-1,4-dihydroquinazolin-3(2H)-yl)piperidin-1-yl]carbonyl}-N-{(2S)-1-oxo-3-(piperidin-4-yl)-1-[4-(pyridin-4-yl)piperazin-1-yl]propan-2-yl}-D-tyrosinamide;

N-[(2R)-3-(7-methyl-1H-indazol-5-yl)-1-oxo-1-({(2S)-1-oxo-3-(piperidin-4-yl)-1-[4-(pyridin-4-yl)piperazin-1-yl]propan-2-yl}amino)propan-2-yl]-4-(2-oxo-1,4-dihydroquinazolin-3(2H)-yl)piperidine-1-carboxamide;

N-[(2R)-3-(7-methyl-1H-indazol-5-yl)-1-oxo-1-({(2S)-1-oxo-3-(piperidin-4-yl)-1-[4-(pyridin-4-yl)piperazin-1-yl]propan-2-yl}amino)propan-2-yl]-2'-oxo-1',2'-dihydro-1H-spiro[piperidine-4,4'-pyrido[2,3-d][1,3]oxazine]-1-carboxamide;

N-[(2R)-1-({(2S)-3-{1-[2-(dimethylamino)ethyl]piperidin-4-yl}-1-oxo-1-[4-(pyridin-4-yl)piperazin-1-yl]propan-2-yl}amino)-3-(7-methyl-1H-indazol-5-yl)-1-oxopropan-2-yl]-4-(2-oxo-2,3-dihydro-1H-imidazo[4,5-b]pyridin-1-yl)piperidine-1-carboxamide;

3-(4-{(2S)-2-{[(2R)-3-(7-methyl-1H-indazol-5-yl)-2-({[4-(2-oxo-2,3-dihydro-1H-imidazo[4,5-b]pyridin-1-yl)piperidin-1-yl]carbonyl}amino)propanoyl]amino}-3-oxo-3-[4-(pyridin-4-yl)piperazin-1-yl]propyl}piperidin-1-yl)-3-oxopropanoic acid, ammonium salt; and 3,5-dibromo-Nα-[(2'-oxo-1',2'-dihydro-1H-spiro[piperidine-4,4'-pyrido[2,3-d][1,3]oxazin]-1-yl)carbonyl]-N-{(2S)-1-oxo-3-(piperidin-4-yl)-1-[4-(pyridin-4-yl)piperazin-1-yl]propan-2-yl}-D-tyrosinamide.

16. The compound according to claim 12, wherein the compound is:

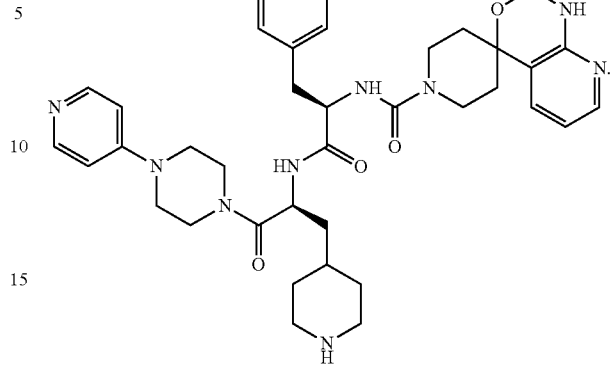

17. The compound according to claim 12, wherein the compound is:

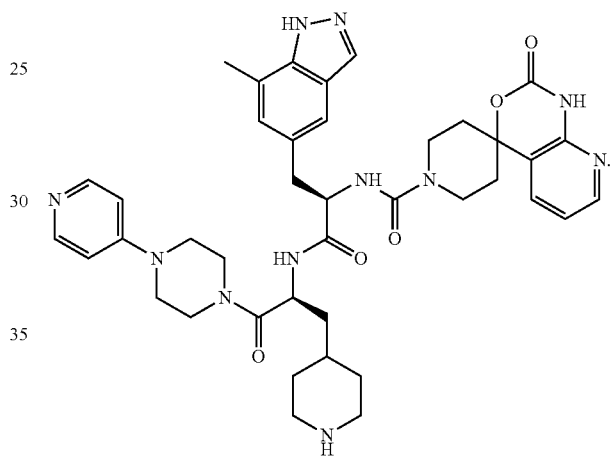

* * * * *